United States Patent
Toth et al.

(10) Patent No.: US 11,382,687 B2
(45) Date of Patent: Jul. 12, 2022

(54) SYSTEMS AND METHODS FOR TREATING CANCER AND/OR AUGMENTING ORGAN FUNCTION

(71) Applicant: Autonomix Medical, Inc., Excelsior, MN (US)

(72) Inventors: Landy Toth, Doylestown, PA (US); Robert S. Schwartz, Inver Grove Heights, MN (US)

(73) Assignee: Autonomix Medical, Inc., Ivyland, PA (US)

( * ) Notice: Subject to any disclaimer, the term of this patent is extended or adjusted under 35 U.S.C. 154(b) by 171 days.

(21) Appl. No.: 16/158,385

(22) Filed: Oct. 12, 2018

(65) Prior Publication Data
US 2019/0046264 A1 Feb. 14, 2019

Related U.S. Application Data

(63) Continuation of application No. 14/958,659, filed on Dec. 3, 2015, now Pat. No. 10,136,944, which is a
(Continued)

(51) Int. Cl.
*A61B 18/14* (2006.01)
*A61B 18/18* (2006.01)
(Continued)

(52) U.S. Cl.
CPC ...... *A61B 18/1492* (2013.01); *A61B 18/1815* (2013.01); *A61B 2018/0022* (2013.01); *A61B 2018/00267* (2013.01); *A61B 2018/00404* (2013.01); *A61B 2018/00434* (2013.01); *A61B 2018/00773* (2013.01);
(Continued)

(58) Field of Classification Search
CPC ..... A61B 5/685; A61B 5/6851; A61B 5/6852; A61B 5/6858; A61B 5/04001; A61B 5/4839
See application file for complete search history.

(56) References Cited

U.S. PATENT DOCUMENTS

| 5,105,165 A | 4/1992 | Bien |
| 6,504,429 B2 | 1/2003 | Kobayashi |

(Continued)

FOREIGN PATENT DOCUMENTS

| WO | 2013086461 A1 | 6/2013 |
| WO | 2013112844 A1 | 8/2013 |

(Continued)

OTHER PUBLICATIONS

Canadian Patent Application Serial No. 2,926,088; Examination Report, dated Jul. 30, 2020; 8 pages.
(Continued)

*Primary Examiner* — Thaddeus B Cox
(74) *Attorney, Agent, or Firm* — Ryan, Mason & Lewis, LLP

(57) ABSTRACT

Systems, methods and devices for controlled sympathectomy procedures for neuromodulation in the treatment of subjects having neoplastic conditions are disclosed. Systems, methods, and devices for interventionally treating a cancerous tumor and cancer related pain are disclosed.

20 Claims, 10 Drawing Sheets

Related U.S. Application Data continuation-in-part of application No. 14/895,744, filed as application No. PCT/US2014/060471 on Oct. 14, 2014, now Pat. No. 10,143,419.

(60) Provisional application No. 62/087,629, filed on Dec. 4, 2014, provisional application No. 62/010,699, filed on Jun. 11, 2014, provisional application No. 61/891,242, filed on Oct. 15, 2013.

(51) Int. Cl.
*A61B 18/00* (2006.01)
*A61B 18/02* (2006.01)

(52) U.S. Cl.
CPC .............. *A61B 2018/00839* (2013.01); *A61B 2018/0212* (2013.01); *A61M 2205/051* (2013.01); *A61M 2205/058* (2013.01)

(56) References Cited

U.S. PATENT DOCUMENTS

| | | |
|---|---|---|
| 6,781,467 B2 | 8/2004 | Sun |
| 6,828,857 B2 | 12/2004 | Paillet et al. |
| 6,864,751 B1 | 3/2005 | Schmidt et al. |
| 7,382,189 B2 | 6/2008 | Chen et al. |
| 7,714,663 B2 | 5/2010 | Gong et al. |
| 7,973,602 B2 | 7/2011 | Shivaram et al. |
| 8,362,836 B2 | 1/2013 | Gilbert et al. |
| 8,655,427 B1* | 2/2014 | Greenspan ............ A61B 5/0538 600/374 |
| 8,953,952 B2 | 2/2015 | Poesel et al. |
| 9,059,665 B2 | 6/2015 | Youssef et al. |
| 9,191,123 B2 | 11/2015 | Kalogerakis et al. |
| 9,608,568 B2 | 3/2017 | Ro et al. |
| 9,956,034 B2 | 5/2018 | Toth et al. |
| 2004/0215173 A1 | 10/2004 | Kunst |
| 2008/0065158 A1 | 3/2008 | Ben-Ezra et al. |
| 2009/0099551 A1* | 4/2009 | Tung ...................... A61B 5/103 604/530 |
| 2009/0306491 A1* | 12/2009 | Haggers ............. A61N 1/37229 600/373 |
| 2010/0143721 A1 | 6/2010 | Chen et al. |
| 2011/0270121 A1* | 11/2011 | Johnson .................. A61B 17/29 600/554 |
| 2011/0306851 A1 | 12/2011 | Wang |
| 2012/0065494 A1 | 3/2012 | Gertner et al. |
| 2012/0123303 A1 | 5/2012 | Sogard et al. |
| 2012/0191079 A1 | 7/2012 | Moll et al. |
| 2012/0296232 A1* | 11/2012 | NG .......................... A61B 5/24 600/554 |
| 2012/0310067 A1 | 12/2012 | Najafi et al. |
| 2013/0012938 A1* | 1/2013 | Asirvatham ......... A61B 5/0215 606/41 |
| 2013/0116737 A1 | 5/2013 | Edwards et al. |
| 2013/0131743 A1 | 5/2013 | Yamasaki et al. |
| 2013/0197555 A1 | 8/2013 | Schaer |
| 2014/0018792 A1 | 1/2014 | Gang et al. |
| 2014/0073903 A1 | 3/2014 | Weber et al. |
| 2014/0271717 A1 | 9/2014 | Goshayeshgar et al. |
| 2015/0011843 A1 | 1/2015 | Toth et al. |
| 2015/0065945 A1* | 3/2015 | Zarins .................. A61K 31/475 604/21 |
| 2015/0066007 A1 | 3/2015 | Srivastava |
| 2015/0297139 A1 | 10/2015 | Toth |
| 2016/0029960 A1 | 2/2016 | Toth et al. |

FOREIGN PATENT DOCUMENTS

| | | |
|---|---|---|
| WO | 2014089553 A1 | 6/2014 |
| WO | 2014160832 A2 | 10/2014 |
| WO | PCT/US2014/060471 | 1/2015 |

OTHER PUBLICATIONS

India Examination Report for Patent Application Serial No. 201647016243, dated Dec. 14, 2020, 10 pages.

European Examination Report for Patent Application Serial No. 14853826.7, dated Jun. 3, 2020, 4 pages.

Australia First Examiners Report for Patent Application Serial No. 2014337552, dated Jun. 27, 2018, 3 pages.

European Extended European Report for Patent Application Serial No. 14853826.7, dated May 17, 2017, 7 pages.

\* cited by examiner

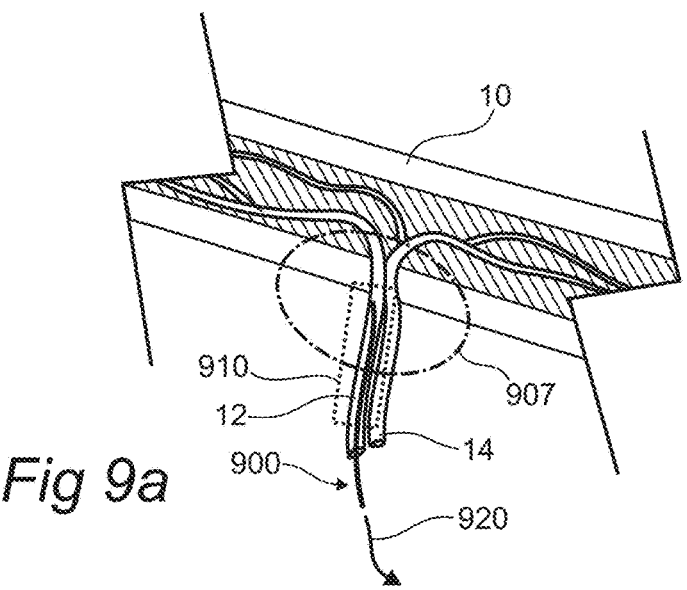
Fig 9a
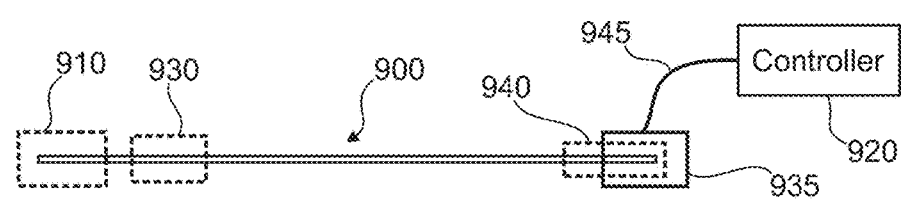
Fig 9b
Fig 9c
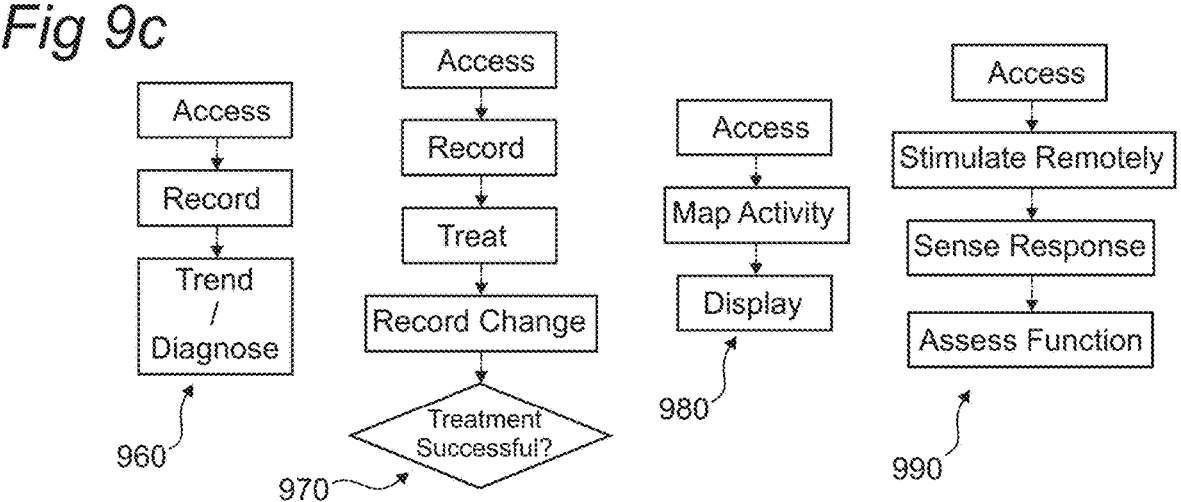
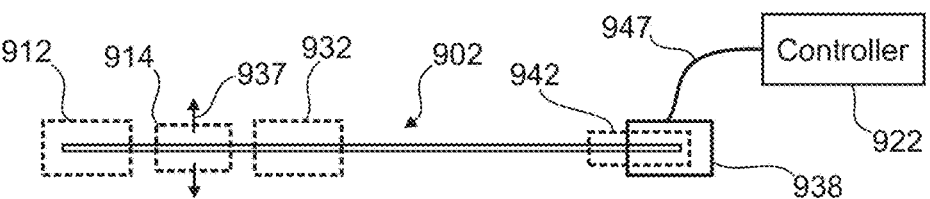
Fig 9d

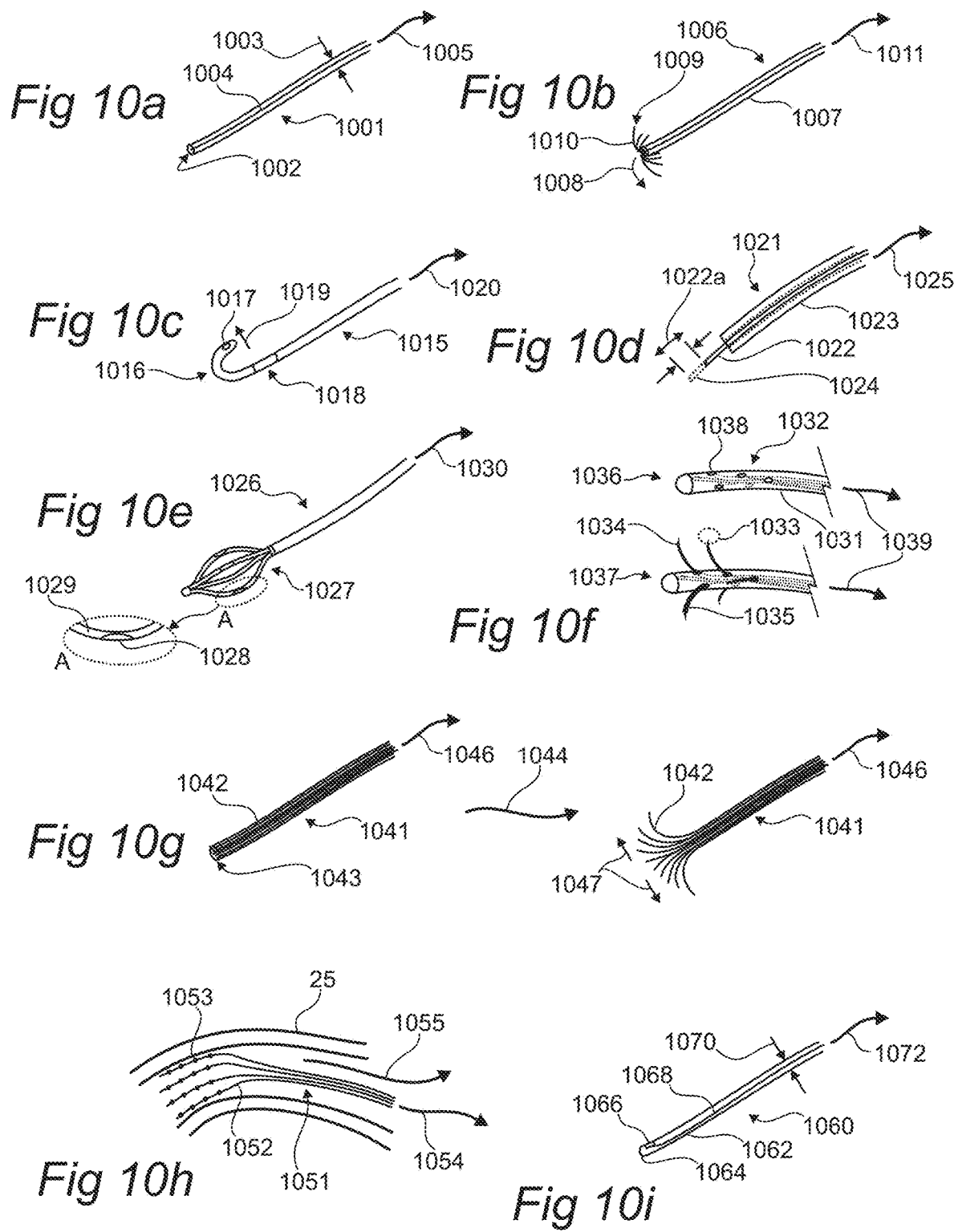

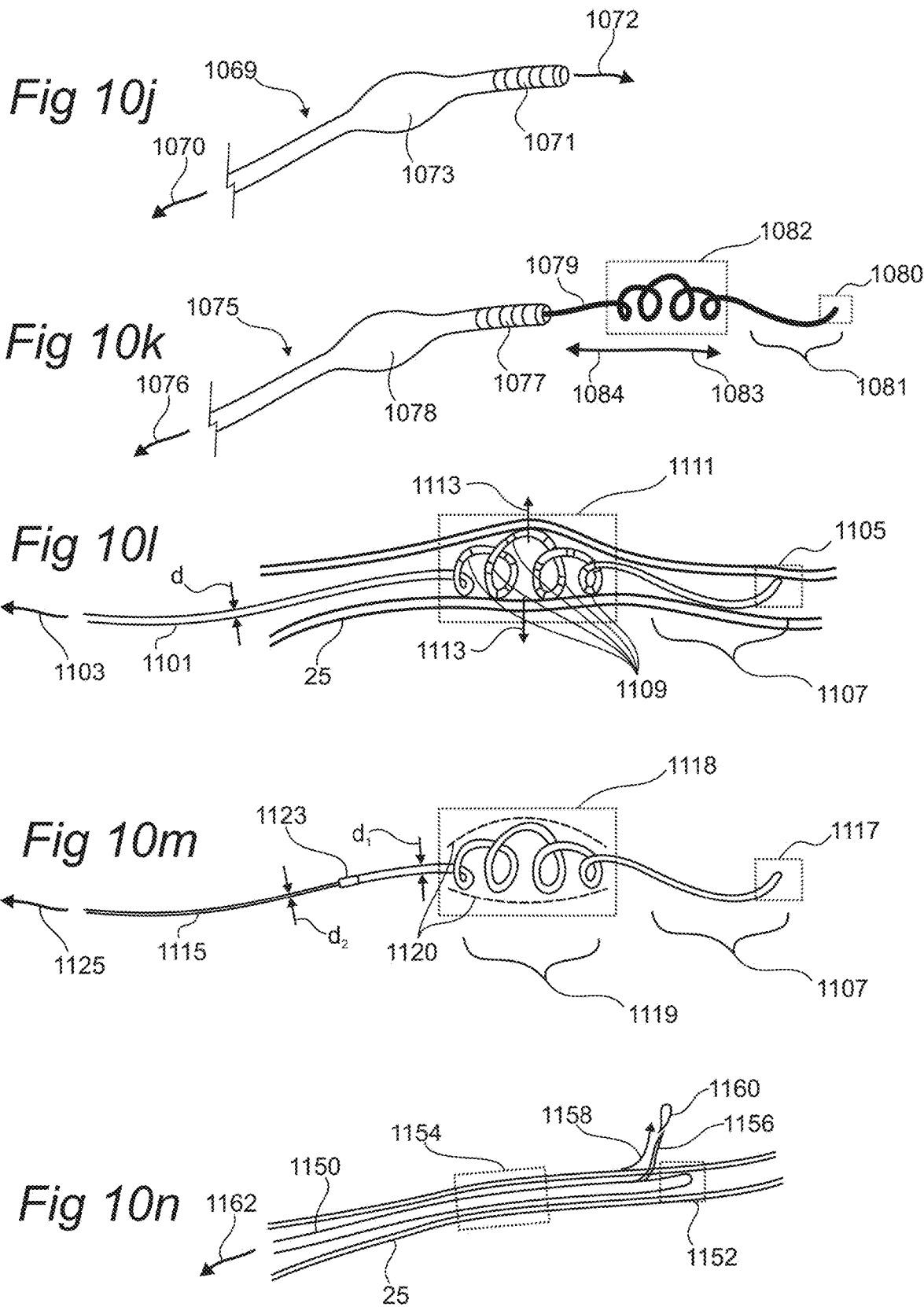

SYSTEMS AND METHODS FOR TREATING CANCER AND/OR AUGMENTING ORGAN FUNCTION

CROSS-REFERENCE TO RELATED APPLICATIONS

The present application is a continuation of U.S. patent application Ser. No. 14/958,659, filed on Dec. 3, 2015, now U.S. Pat. No. 10,136,944, entitled "Systems and Methods for Treating Cancer and/or Augmenting Organ Function," which claims benefit of and priority to U.S. Provisional Application Ser. No. 62/087,629, filed on Dec. 4, 2014, entitled "Systems and Methods for Treating Cancer and/or Augmenting Organ Function", and is a continuation-in-part application claiming the benefit of and priority to U.S. patent application Ser. No. 14/895,744, filed on Dec. 3, 2015, now U.S. Pat. No. 10,143,419, a national stage application of International Application No. PCT/US2014/060471, which claims benefit of and priority to U.S. Provisional Application Ser. No. 61/891,242 filed on Oct. 15, 2013, and Provisional Application Ser. No. 62/010,699 filed on Jun. 11, 2014, each entitled "Systems and Methods for Treating Cancer and/or Augmenting Organ Function", the entire contents of which are each incorporated by reference herein.

BACKGROUND

Background

Tumor growth, spread, and eventual invasion into surrounding tissues and structures in the body continues to be an unresolved disease state, having a profound impact on cancer patient outcomes.

Aggressive therapies are often ineffective at stemming growth of the tumors over the long term, and can often contribute to pain and suffering of treated patients.

Perineural invasion of cancerous tumors is a hallmark of many aggressive forms of cancer. Often, patient outcomes diminish dramatically once perineural invasion has begun. Furthermore, pain and patient discomfort may be associated with such perineural invasion, the direct effects of which can have negative impact on patient outlook, optimism, and outcome. Long term use of analgesic medications to counteract such pain can also have detrimental effects on patient outlook, optimism, and outcome.

There are several approaches available for treating cancer-related pain.

Opioids are often used as full agonists at the morphine receptor (e.g., morphine, oxycodone, hydromorphone), or partial agonist opioids (e.g., buprenorphine). Opioids hyperpolarize nociceptive cell membranes, shorten the duration of their action potentials, and inhibit the release of excitatory mediators. Chronic use can lead to neuropathic pain and generally is accompanied by many side effects.

Anti-inflammatory drugs, non-steroidal anti-inflammatory drugs (NSAIDS) decrease inflammation by inhibiting the synthesis of peripheral prostaglandins. NSAIDS are often effective at treating cancer pain that does not originate from nerve damage.

Neuropathic cancer pain is often treated with anticonvulsants, antidepressants, corticosteroids, capsaicin, opioids, and lidocaine patches.

Radiotherapy, radionuclide therapy, etc. employs ionizing radiation focused at cancer cells. Generally, this approach causes apoptotic death of tumor cells, and radiosensitive inflammatory cells.

Neurolytic celiac plexus block can be effective in the treatment of cancer pain but is accompanied by several risks and complications (including paraplegia). Often the celiac plexus is blocked with a 10% phenol solution or absolute alcohol solution. Celiac block can also lead to hypotension (complication of lumbar sympathetic block complications), or paraplegia due to volume spread of solution into the spinal cord. Thus, existing procedures are fraught with complications.

Intraspinal drug administration is an approach that is used to deliver pain medication directly into the spine, termed 'spinal analgesic chemotherapy' and can improve the effect of opioid, NSAIDS, and other drug treatments through localized delivery into the spine.

Bone cancer can be particularly painful. Pain progression of bone cancer pain is usually a dull, constant pain, which gradually increases in intensity over time. As the cancer progresses, a breakthrough or severe pain can emerge spontaneously or with movement or load bearing. Such breakthrough pain is often acute, severe, debilitating, and difficult to control.

SUMMARY

According to a first aspect, there is provided a system for treating a cancerous tumor and/or cancer pain coupled to a target organ, and/or altering the neural traffic in a microenvironment coupled to the target organ within a body, including a catheter (i.e., a balloon catheter, a needle catheter, a flexible catheter, etc.) or a guidewire sized and dimensioned for delivery into a lumen (i.e., an artery, vein, vessel, forma, or the like) serving the target organ and/or the tumor, the catheter or guidewire including a distal tip configured to interface with the walls of an artery, vein, vessel coupled to the target organ, the distal tip configured for delivery of energy and/or a substance to one or more nerves coupled to the target organ.

According to aspects, there is provided a system for altering a function of a target organ and/or altering the neural traffic in a microenvironment coupled to the target organ within a body, including a catheter (i.e., a balloon catheter, a needle catheter, a flexible catheter, etc.) or a guidewire sized and dimensioned for delivery into a lumen (i.e., an artery, vein, vessel, forma, or the like) serving the target organ, the catheter or guidewire including a distal tip configured to interface with the walls of an artery, vein, vessel coupled to the target organ, the distal tip configured for delivery of energy and/or a substance to one or more nerves coupled to the target organ.

In aspects, the distal tip may include a balloon, a basket, a deployable helix, a deployable microneedle, a combination thereof, or the like for interfacing with the wall.

The energy may be thermal energy, RF (radio frequency) current, MW (microwave) current, ultrasound, MR (magnetic resonance) guided HIFU (high intensity focused ultrasound), radiation, cryotherapy, combinations thereof, or the like.

In aspects, the substance may be a medicament, a denervating agent, a sympathetic nerve specific denervating agent, a parasympathetic nerve specific denervating agent, a neuroblocking agent, a highly specific neuroblocking agent (i.e., an agent specifically configured for blocking of a particular receptor, nerve family, etc.), or the like. In aspects, the denervating agent may be ethanol, phenol, botulinum toxin, or the like. In aspects, the highly specific denervating agent may be a neural targeting chemical, etc.

In aspects, the catheter or guidewire may include one or more sensing elements each in accordance with the present disclosure, located within the vicinity of the distal tip thereof, configured to interface with and/or monitor electrophysiological activity from one or more nerves coupled to the target organ upon placement (i.e., during a surgical procedure, etc.). One or more sensing elements may be configured and dimensioned to monitor local physiologic data, electrophysiological data, neural traffic, sympathetic neural traffic, parasympathetic neural traffic, afferent neural traffic, efferent neural traffic, smooth muscle response, or the like from the target organ and/or within the vicinity of the target organ. Such information may be advantageous for determining the extent of a treatment, a disease state of the organ, for predicting the response of the organ and/or a neural circuit connected thereto to a treatment, an ablation, a delivery of energy, or the like.

In aspects, the catheter or guidewire may be equipped with a substance eluting element, configured to deliver a substance, a medicament, a denervating substance, a combination thereof, or the like into the target organ, into a perivascular site surrounding the wall of the lumen, into the adventitia of the lumen, into a microenvironment of the tumor, into the lumen, into the tissues surrounding the wall of the lumen, a combination thereof, or the like.

In aspects, the energy and/or substance may be delivered and configured to interrupt, block, and/or augment neural traffic along one or more nerves coupled to the target organ. In aspects, the energy and/or substance may be provided so as to block nerve traffic to and/or from the organ along the lumen into which the distal tip has been inserted.

In aspects, the system may include a balloon coupled with the distal tip, the balloon coupled to a fluid source so as to be expand-ably deployed during a procedure so as to interface with the walls of lumen upon placement of the distal tip therein. The balloon may include one or more energy delivery elements, and/or sensing elements to interface with the wall of the lumen, one or more of the nerves, to brace the distal tip against the wall of the lumen, to alter blood flow past the distal tip, or the like.

In aspects, the system may be configured to direct energy through the energy delivery elements based upon the information collected by the sensing elements. The sensing elements may be sized, dimensioned, shaped, and configured to monitor and/or determine the signals relating to regions of abnormal electrophysiological activity, determine the direction of nerve traffic along nerves in the vicinity of the lumen, sympathetic neural activity in the vicinity of the lumen, determine the type of nerves situated near the sensing element, determine the effectiveness of the energy and/or substance delivery, determine the response of nerve traffic to a stress test performed on the body or the organ, combinations thereof, or the like. In aspects, the system may be configured to direct the energy delivery into one or more regions of the lumen wall, through the lumen wall, into the adventitia, into the target organ, adjacent to the lumen, into a microenvironment of the tumor, combinations thereof, or the like.

The system may include a stress testing element, configured to apply a local and/or systemic stress to the body, one or more of the sensing elements configured to monitor the response of the nerves to the stress. Such stressed response may be advantageous for assessing the type, proportion of, and/or properties of the nerves in the vicinity of the lumen wall, assess the neural response to the stress state, assess the functionality of the organ, or the like.

The distal tip may include a characteristic diameter of less than 1 mm (millimeter), less than 0.75 mm, less than 0.5 mm, or less than 0.3 mm so as to access the lumen near to or within a site within the target organ.

According to aspects, there is provided use of a system in accordance with the present disclosure to treat pain, e.g., pain associated with perineural invasion of a cancerous tumor, pain associated with neural receptor damage in the vicinity of inflammation and/or a tumor microenvironment, or the like.

According to aspects, there is provided use of a system in accordance with the present disclosure to treat and/or slow the progression of a cancerous tumor. Some non-limiting examples of such cancer that may be treated include cancer of the prostate, pancreas, breast, colon, cervix, liver, bone, and the like.

According to aspects, there is provided use of a system in accordance with the present disclosure to slow, hinder, and/or prevent perineural invasion of a cancerous tumor into a surrounding nerve structure.

According to aspects, there is provided use of a system in accordance with the present disclosure to interrupt, decrease, and/or stop neural communication to a cancerous tumor and/or the microenvironment surrounding the tumor (i.e., to interrupt nerve traffic to/from a cancerous tumor or the tissues thereby to the rest of the body).

According to aspects, there is provided use of a system in accordance with the present disclosure to destroy nerves in the vicinity of a tumor.

According to aspects, there is provided use of a system in accordance with the present disclosure to slow or even halt tumorigenesis of cancerous tissue.

According to aspects, there is provided use of a system in accordance with the present disclosure to treat local inflammation (such as for the treatment of pancreatitis, prostatitis, irritable bowel syndrome, etc.).

In aspects, the system may include a balloon coupled with the catheter, situated in the vicinity of the distal tip thereof, the balloon coupled to a fluid source so as to be expand-ably deployed during a procedure so as to interface with the walls of lumen into which the distal tip may be deployed.

In aspects, the balloon may include one or more energy delivery elements, and/or sensing elements each in accordance with the present disclosure configured to interface with tissues adjacent to the balloon during a procedure. In aspects, the sensing elements may be configured to monitor electrophysiological information associated with the adjacent tissues.

In aspects, the system may be configured to direct energy through the energy delivery elements based upon the information collected by the sensing elements. In aspects, the sensing elements may be used to determine regions of abnormal electrophysiological activity, determine the direction of nerve traffic along the lumen, determine the type of nerves situated near the sensing element, etc. In aspects, the energy delivery may be directed to one or more regions of the lumen wall, through the lumen wall, into the adventitia surrounding a lumen, into an organ (i.e., a pancreas, a liver, an intestinal wall, a cervix, a breast, a kidney, a bone, etc.) adjacent to the lumen, etc. as directed by data collected by the sensing elements during the procedure.

In aspects, relating to a treatment for bone cancer, the energy and/or chemical substance may be directed to one or more regions of a periosteal space surrounding a bone and/or into a foramen at a site of vessel entry into the bone, to neural tissues surrounding one or more artery or vein segments near to the bone surface, within the margin of the bone, along the artery or vein heading to the bone, but after break away from a larger, less specific vessel, near the foramen of the bone, and/or periosteal space of the bone.

In aspects, the energy delivery elements and/or sensing elements may be sized and arranged such that they may be placed within an artery, vein, and/or foramen of a bone. In aspects, the delivery elements and/or sensing elements may be sized and dimensioned such that a characteristic diameter thereof is less than 1 mm, less than 0.75 mm, less than 0.5 mm, less than 0.3 mm, or the like.

In aspects, the system may include a stress testing component, the stress testing component configured to apply a stress (i.e., local and/or systemic) to the body while monitoring the response to the stress via one or more of the sensing elements. In aspects, the stress testing component may be configured to deliver one or more substances into the organ, and/or artery coupled thereto. The substances may be selected so as to alter the functional state of the organ upon delivery thereto, the sensing elements configured to monitor a change in the electrophysiological activity in response to the change in functional state. In aspects, the system may be used to diagnose a disease state, determine a function of the adjacent tissues, and/or determine the type of adjacent tissues (i.e., a nerve fiber, a type of nerve fiber, etc.) based upon the data obtained by the one or more sensing elements during the stress.

In aspects, there is provided a method for treating a cancerous tumor, altering an organ function, and/or altering neural traffic in a microenvironment coupled to the tumor or a target organ within a body accessing a wall of a lumen in the vicinity of the target organ or the tumor, and delivering energy and/or a substance to at least a portion of the wall of the lumen, to a nerve coupled with the tumor and/or organ, through at least a portion of the wall of the lumen, and/or into the tissues surrounding the tumor and/or the organ.

In aspects, the method may include collecting physiologic data, electrophysiological data, neural traffic, sympathetic neural traffic, parasympathetic neural traffic, afferent neural traffic, efferent neural traffic, smooth muscle response, or the like from the target organ and/or within the vicinity of the target organ. Such information may be advantageous for determining the extent of a treatment, a disease state of the organ, for predicting the response of the organ and/or a neural circuit connected thereto to a treatment, an ablation, a delivery of energy, or the like.

In aspects, the method may include directing the energy and/or substance based upon the collected physiologic data.

In aspects, the method may include collecting further physiologic data after the delivery of energy to determine if the treatment was successful.

The method may include collecting further physiologic data after the delivery of the energy and/or the substance to determine if the delivery affected the microenvironment around the tumor, the nerve coupled to the tumor, and/or the perivasculature of the lumen.

The method may include applying a stress test to the subject during the collecting of physiologic data. Some non-limiting examples of a stress test include a valsalva maneuver, a tilt table test, elevating one or more legs, transient sitting to standing exercises, executing a change in posture, moving from a prone position to a sitting or standing position, a breath holding technique, or combinations thereof.

In aspects, the stress test may include injecting a vasodilator, a vasoconstrictor, a neuroblocker, a neurostimulant, a diuretic, insulin, glucose, a beta-adrenergic receptor antagonist, an angiotensin-11 converting enzyme inhibitor, a calcium channel blocker, an HMG-CoA (3-hydroxy-3-methyl-glutaryl-coenzyme A) reductase inhibitor, digoxin, an anticoagulant, a diuretic, a beta blocker, an ACE (angiotensin-converting enzyme) inhibitor, a steroid, or combination thereof to the organ and/or subject and monitoring the local response thereto. In aspects, the injection may be directed into the lumen, into the tumor, into the adventitia surrounding the lumen, and/or into an organ coupled thereto.

In aspects, one or more steps of a method in accordance with the present disclosure may be performed by a system in accordance with the present disclosure.

In aspects, the target organ may be a bone. The method may be used to treat bone pain, bone cancer pain, osteoporosis, etc. In aspects, the energy and/or substance delivery may be performed in a vessel, a periosteal space, a foramen, a medullary cavity, a combination thereof, or the like of the bone. A non-limiting example of the bone may be a long bone (e.g., a femur), and the lumen may be a nutrient, epiphyseal, or metaphyseal artery, vein or forma.

In aspects, the substance may include an antibody drug conjugate (ADC), a chemotherapeutic agent, etc. In aspects, the ADC substance may be configured to affect the function of a region or tissue type within the vicinity of the organ alternatively to the other tissues within the vicinity thereof. In aspects, the substance may include a sugar attached to a therapeutic agent to mask the therapeutic agent, such that it is to be taken up by the region of tissue (i.e., appear as a sugar, a friendly protein, etc.). Such a configuration provides a method for delivering a highly potent medicament directly to a tissue of interest (i.e., directly into a tumor), so as to enhance the bioavailability thereof, and to minimize the systemic dosage required in order to achieve significant therapeutic concentrations thereof within the region of tissue.

In aspects, the substance may be delivered at a rate of less than 1 mg/hr (milligrams/hour), less than 0.01 mg/hr, less than 1 µg/hr (micrograms/hour), or the like. Such a configuration may be important so as to minimize local stress and damage caused by the introduction of the substance into the microenvironment of the tissue of interest.

In aspects, a system in accordance with the present disclosure may include a catheter and/or a guidewire configured for percutaneous access to the arteries, veins, or lumens, of a body, for delivery through one or more arteries of the body to the vicinity of the target organ. An associated method in accordance with the present disclosure may include inserting a tip of the catheter and/or guidewire into the artery or vein to access the neural structures near to or within the target organ.

Aspects of the invention include treatment of subjects suffering from neoplastic disease conditions, i.e., disease conditions characterized by the occurrence of unwanted cellular proliferation, e.g., as manifested by the appearance/ growth of one or more solid tumors. By treatment is meant at least an amelioration of the symptoms associated with the disease condition afflicting the subject (i.e., host), where amelioration is used in a broad sense to refer to at least a reduction in the magnitude of a parameter, e.g., symptom, associated with the pathological condition being treated, such as size of tumor, rate of growth of tumor, spread of tumor, pain, etc. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. Where the symptom being treated is pain, treatment in accordance with methods of the invention results in some instances in a decrease in the National Initiative on Pain Control (NIPC) numerical scale of 1 point or more, such as 2 points or more, 3 points or more, 4 points or more, 5 points or more, 6 points or more, 7 points or more, 8 points or more, including 9 points or more. As such, treatment includes both curing and managing a pain condition. Where the symptom being treated is tumor growth, treatment in accordance with methods of the invention results in some instances in a decrease in the rate of tumor growth, e.g., as compared to a suitable control, where the magnitude of the decrease in rate may be 5% or greater, such as 10% or greater, including 20% or greater. In some instances, treatment in accordance with methods of the invention results in a reduction in tumor size, where the reduction may be 5% or more, including 10% or more, such as 15% or more, e.g., 25% or more, 50% or more, 75% or more, v/v.

A variety of subjects are treatable according to the methods of the invention. Subjects treatable as described herein include "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is human.

Aspects of the invention include treatment of subjects suffering from a tumor. Examples of tumors including carcinomas, adenocarcinomas, lympohomas, sarcomas, and other solid tumors, as described in U.S. Pat. No. 5,945,403, solid tumors; benign tumors, for example hemangiomas, acoustic neuromas, neurofibromas, trachomas, and pyogenic granulomas. In some cases, methods and compositions described herein are employed for the treatment of subjects having, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V. T. et al. eds 1997) for additional cancers), etc.

Where the methods are directed to treatment of subjects having one or more solid tumors, aspects of such embodiments may include methods where tumor tissue itself is not modulated as described herein. Instead, only nerve(s) operatively coupled to the tumor is modulated, e.g., ablated. As such, in these embodiments the tumor itself is not ablated. Such may be done following an assessment of which nerve (s) are suitable for modulation to achieve the desired treatment goal, e.g., using evaluation protocols as described herein.

According to aspects, there is provided a method for treating a tumor including neuromodulating electrophysiological activity of one or more nerves coupled to the tumor and/or a perineural microenvironment surrounding the tumor. The neuromodulation may include stimulating, stressing, and/or ablating the nerves in accordance with the present disclosure.

In aspects, the method may include stimulating the neural circuit with a stimulation frequency suitable to provide a neural block there along.

In aspects, the method may include providing energy and/or a bolus of a chemical agent in an amount sufficient to provide a neural block to one or more regions of the neural circuit, and/or ablate one or more regions of the neural circuit.

The method may include decoupling a neurological connection between the tumor and a neural circuit in the body and/or a brain in the body, monitoring the electrophysiological activity before, during, and/or after the step of neuromodulating, determining the effectiveness of the step of neuromodulating based upon the monitoring, and/or determining the type and/or location for the step of neuromodulating based upon the monitoring.

According to aspects, there is provided use of a system and/or method in accordance with the present disclosure to treat pancreatic cancer, prostate cancer, breast cancer, colon cancer, liver cancer, cervical cancer, ovarian cancer, bladder cancer, bone cancer, combinations thereof, and the like.

According to aspects, there is provided use of a system or method in accordance with the present disclosure for preventing or slowing the growth rate and/or tumorigenesis of a tumor, modulating neural communication between a tumor and one or more neural circuits coupled to the target organ, augmenting/treating/ablating the perineural microenvironment in the vicinity of a tumor or along a neural circuit coupled thereto, and/or preventing or slowing the process of perineural invasion of a tumor into surrounding tissues According to aspects, there is provided use of a system or method in accordance with the present disclosure to treat osteoporosis, augment bone density, adjust the rate of bone remodeling, alter the formation of osteoblasts, or the like.

In aspects, a method in accordance with the present disclosure may include inserting the distal tip of a device in accordance with the present disclosure into a vessel coupled to the tumor. In aspects, the method may include advancing the tip of the device along the vessel such that the tip may interact with a wall of the vessel sufficiently near to the tumor so as to selectively interact with the neural structures coupled specifically to the tumor. Such positioning may be advantageous so as to minimally influence other neural structures in the body while interacting with those coupled to the tumor. In one non-limiting example related to the treatment and/or pain reduction of a bone cancer tumor located in the diaphysis region of a femur, the method may include advancing the tip of the device along an artery or vein within the body so as to reach the nutrient artery and/or vein near to the femur (i.e., sufficiently near such that the nerves running alongside the artery and/or vein are primarily coupled with the femur as opposed to nearby muscles, skin, peroneal nerves, or the like). In aspects, the tip may be advanced along the nutrient artery so as to enter a branch dedicated to the femur, so as to interact with the vessels near to the periosteum of the femur, near to the foramen where the nutrient artery or vein enters the femur, to pass within the medullary cavity of the femur, or the like. In aspects a method to treat a tumor and/or pain associated therewith in the epiphysis and/or metaphysis of a femur may include accessing an epiphyseal and/or metaphyseal artery with a tip of a device in accordance with the present disclosure.

In aspects, a method in accordance with the present disclosure may include applying energy and/or a chemical agent into an adventitia of the vessel.

In aspects, a method in accordance with the present disclosure may include monitoring electrophysiological activity along a wall of the vessel. The method may include monitoring neural activity, nerve traffic, sympathetic neural activity, parasympathetic neural activity, afferent neural traffic, efferent neural traffic, differentiating between one or more of the types of traffic, monitoring traffic during a stress test, before and/or after stimulation and/or treatment of the tissues, or the like.

In aspects, the method may include using the monitoring to determine the extent of a treatment, to alter a bolus of energy or chemical agent delivered, or the like. In aspects, such determination may be made by monitoring one or more changes in the electrophysiological signals, changes in the neural traffic, changes in a proportion of afferent and/or efferent traffic in the vicinity of the vessel wall, changes in the response of traffic to a stress test, to a stimulation, or the like.

According to aspects, there is provided a method for treating a tumor including inducing apoptosis within neural tissues within the vicinity of the tumor, within a neural circuit coupled with the tumor, or the like. Such treatment may be provided by a system and/or method in accordance with the present disclosure.

According to aspects, there is provided a method for treating a tumor including inducing necrosis within neural tissues within a neural circuit coupled with the tumor.

In aspects, the method may include ablating one or more nerves coupled to the tumor, while substantially limiting damage to the tissues surrounding the nerves, substantially limiting damage to an organ coupled to the tumor, substantially limiting local inflammation, or the like.

In aspects, induced necrosis will typically cause the corresponding cells to exhibit rapid swelling, lose membrane integrity, shut down metabolism, and release their contents into the environment. Cells that undergo rapid necrosis in vitro do not often have sufficient time or energy to activate apoptotic machinery and thus will often not express apoptotic markers. Rather, induced apoptosis typically causes the corresponding cells to exhibit cytological and molecular events such as a change in the refractive index of the cell, cytoplasmic shrinkage, nuclear condensation, and cleavage of DNA into regularly sized fragments.

In aspects, the chemical agent may be selected so as to induce apoptosis in one or more neural tissues (i.e., axon, dendrite, cell body, myelin sheath, synapse, etc.).

According to aspects, there is provided use of one or more systems, methods, and devices each in accordance with the present disclosure for interventionally altering one or more homeostatic processes within a body.

Some non-limiting examples of homeostatic processes include production/release of renin, insulin, cholesterol, bile salts, testosterone, progesterone, prion, serotonin, endorphins, dopamine, monoamine neurotransmitters, histamines, noradrenaline, glucose, and the like, adjustment of blood pressure, anti-inflammatory activity, testosterone, estrogen, "uterine hemorrhaging", hunger, bowel movement, nutritional uptake in the bowel, bone density, a rate of bone remodeling, formation of osteoblasts and the like.

In aspects, a system in accordance with the present disclosure may include a substance delivery aspect, configured for elution of a substance into the vicinity of the target.

In aspects, the system may include one or more sensing elements configured for monitoring of one or more physiologic parameters associated with the target, the homeostatic process in question, a stress response, or the like.

In aspects, the system may include one or more energy delivery elements configured to deliver a bolus of energy to the target in order to alter the homeostatic process.

Aspects of the invention further include combining the disclosed neuromodulatory protocols with one or more neoplastic disease therapeutic and/or palliative therapies. For example, the present devices and methods may be used in combination with the use of one or more anti-cancer agents. As used herein, anti-cancer agents (used interchangeably with "anti-tumor or anti-neoplastic" agent) include any anti-cancer therapies, such as radiation therapy, surgery, hyperthermia or hyperthermia therapy, or anti-cancer compounds useful in the treatment of cancer. These include any agents, when used alone or in combination with another agent, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Exemplary anti-cancer compounds include, but are not limited to, cytokines, chemokines, growth factors, photosensitizing agents, toxins, anti-cancer antibiotics, chemotherapeutic compounds, radionuclides, angiogenesis inhibitors, signaling modulators, anti-metabolites, anti-cancer vaccines, anti-cancer oligopeptides, mitosis inhibitor proteins, antimitotic oligopeptides, anti-cancer antibodies (e.g., single-chain antibodies), anti-cancer antibiotics, immunotherapeutic agents, bacteria and any combinations thereof. Exemplary cytokines and growth factors include, but are not limited to, interleukins, such as, for example, interleukin-1, interleukin-2, interleukin-6 and interleukin-12, tumor necrosis factors, such as tumor necrosis factor alpha (TNF-$\alpha$), interferons such as interferon gamma (IFN-$\gamma$) granulocyte macrophage colony stimulating factors (GM-CSF), angiogenins, and tissue factors. Photosensitizing agents include, but are not limited to, for example, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides or cationic dyes. Radionuclides, which depending upon the radionuclide, amount and application can be used for diagnosis and/or for treatment. They include, but are not limited to, for example, a compound or molecule containing 11 Carbon, 11 Fluorine, 13 Carbon, 15 Nitrogen, 18 Fluorine, 19 Fluorine, 32 Phosphate, 60 Cobalt, 90 Yttirum, 99 Technetium, 103 Palladium, 106 Ruthenium, 111 Indium, 117 Lutetium, 125 Iodine, 131 Iodine, 137 Cesium, 153 Samarium, 186 Rhenium, 188 Rhenium, 192 Iridium, 198 Gold, 211 Astatine, 212 Bismuth or 213 Bismuth. Toxins include, but are not limited to, chemotherapeutic compounds such as, but not limited to, 5-fluorouridine, calicheamicin, maytansine, double-chain ricin, ricin A chain, abrin, abrin A chain, saporin, modeccin, modeccin A chain, *Pseudomonas aeruginosa* exotoxin, Cholera toxin, Shigella toxin, *E. coli* heat labile toxin and Diptheria toxin, doxorubicin, daunomycin, methotrexate, taxol, ricin A, colchicine, cytochasins, monensin, ouabain, mitoxanthrone, vindesine, vinblastine, vincristine and enterotoxin. Anti-metabolites include, but are not limited to, methotrexate, 5-fluorouracil, 6-mercaptopurine, cytosine arabinoside, hydroxyurea and 20-chlorodeoxyadenosine. Signaling modulators include, but are not limited to, for example, inhibitors of macrophage inhibitory factor, toll-like receptor agonists and stat 3 inhibitors. Anti-cancer antibiotics include, but are not limited to, anthracyclines such as doxorubicin hydrochloride (adriamycin), idarubicin hydrochloride, daunorubicin hydrochloride, aclarubicin Hydrochloride, epirubicin hydrochloride and purarubicin hydrochloride, enomycin, phenomycin, pleomycins such as pleomycin and peplomycin sulfate, mitomycins such as mitomycin C, actinomycins such as actinomycin D, zinostatinstimalamer and polypeptides such as neocarzinostatin. Anti-cancer antibodies include, but are not limited to, Rituximab (RITUXAN), ADEPT, Trastuzumab (HERCEPTIN), Tositumomab (BEXXAR), Cetuximab (ERBITUX), Ibritumomab (90 Y-Ibritumomab tiuexetan; ZEVALIN), Alemtuzumab (Campath-1H), Epratuzumab (Lymphocide), Gemtuzumab ozogamicin (MYLOTARG), Bevacimab (AVASTIN), and Edrecolomab (PANOREX). Angiogenesis inhibitors include, but are not limited to, collagenase inhibitors such as metalloproteinases and tetracyclines such as minocycline, naturally occurring peptides such as endostatin and angiostatin, fungal and bacterial derivatives, such as fumagillin derivatives like TNP-470, aptamer antagonist of VEGF, batimastat, Captopril, cartilage derived inhibitor (CDI), genistein, interleukin 12, Lavendustin A, medroxyprogesterone acetate, recombinant human platelet factor 4 (rPF4), taxol, D-gluco-D-galactan sulfate (Tecogalan(=SP-PG, DS-4152)), thalidomide, thrombospondin. Chemotherapeutic compounds include, but are not limited to platinum; platinum analogs (e.g., platinum coordination complexes) such as cisplatin, carboplatin, oxaliplatin, DWA2114R, NK121, IS 3 295, and 254-S; anthracenediones; vinblastine; alkylating agents such as thiotepa and cyclosphosphamide; alkyl sulfonates such as busulfan, improsulfan and piposulfan; aziridines such as benzodopa, carboquone, meturedopa and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; substituted ureas; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; anti-cancer polysaccharides; polysaccharide-K; razoxane; sizofiran; spirogermanium; tenuazonic acid; triaziquone; 2,2',2''-trichlorotriethylamine; urethan; vindesine; dacarbazine; mannomustine; mitobronitol; mitolactol;

pipobroman; gacytosine; cytosine arabinoside; cyclophosphamide; thiotepa; taxoids, such as paclitaxel and doxetaxel; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; XELODA; ibandronate; CPT11; topoisomerase inhibitor RFS 2000; difluoromethylornithine (DMFO); retinoic acid; esperamicins; capecitabine; methylhydrazine derivatives; Erlotinib (TARCEVA); sunitinib malate (SUTENT); and pharmaceutically acceptable salts, acids or derivatives of any of the above. Also included in this definition are anti-hormonal agents that act to regulate or inhibit hormone action on tumors such as anti-estrogens including, for example, tamoxifen, raloxifene, aromatase inhibiting 4 (5)-imidazoles, 4-hydroxytamoxifen, trioxifene, keoxifene, LY117018, onapristone and toremifene (FARESTON); adrenocortical suppressants; and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods. As used herein, an anti-cancer oligopeptide or an anti-tumor oligopeptide is short polypeptide that has the ability to slow or inhibit tumor growth and/or metastasis. Anti-cancer oligopeptide typically have high affinity for and specificity to tumors enabling them to target tumors. Such oligopeptides include receptor-interacting compounds, inhibitors of protein-protein interactions, enzyme inhibitors, and nucleic acid-interacting compounds. As used herein an antimitotic oligopeptide is an oligopeptide that inhibits cell division. An antimitotic oligopeptide is an exemplary anti-cancer oligopeptide. Exemplary antimitotic oligopeptides include, but are not limited to, tubulysin, phomopsin, hemiasterlin, taltobulin (HTI-286, 3), and cryptophycin.

According to aspects, there is provided a method for blocking at least one of one or more nerves and one or more lymphatic ducts coupled to at least one of a tumor and a metastatic cell within a body. In aspects, the blocking step isolates at least one of the tumor and the metastatic cell within the body. In aspects, the blocking step alters growth rates of at least one of the tumor and metastatic cell within the body. In aspects, the blocking step is performed by injecting a neurolytic agent into at least one of the nerves, the lymphatic ducts and nearby tissue. In aspects, the blocking step includes injecting a mild inflammatory agent into at least one of the nerves and the lymphatic ducts. In aspects, at least one of the one or more nerves and at least one of the one or more lymphatic ducts being blocked is at least 10 mm, 20 mm, or 25 mm in length.

In aspects, the method may include accessing at least one of the nerves and the lymphatic ducts via one of a nearby artery, a vein and a duct.

In aspects, the method provides that the blocking step further comprises altering the structure of a perineural sheath of one or more nerves. In aspects, the blocking step further comprises performing architectural destruction of at least one of nerve tissue and lymphatic ductal tissue via inflammation. In aspects, the blocking step further comprises forming scar tissue along at least one of the nerves and the lymphatic ducts.

In aspects, the method provides that the blocking step further comprises using a single therapeutic compound. In aspects, the compound comprises one of an ablative agent, a migration limiting agent, and an inflammatory accelerating agent. In aspects, the blocking step treats at least one of a tumor, a metastasis migration and cancer pain.

In aspects, the method may include confirming completion of the blocking step. In aspects, confirmation is performed at least in part by at least one of a system, a device, and a sensor positioned within at least one of a nearby tissue site, an artery, a vein, and a duct.

In aspects, the method includes sensing neural traffic along the nerves at least one of before, during, and after the blocking step to at least one of locate the nerves and confirm completion of the block.

In aspects, the method provides that the blocking step, the confirmation step and the sensing step may be performed at least in part by a device in accordance with the present disclosure. In aspects, the device may include a balloon, a basket, a deployable helix, a deployable microneedle, or a combination thereof inserted into at least one of a nearby artery, a vein, and a duct arranged so as to interface with the nerves upon deployment.

According to aspects, a method is provided for blocking at least one of one or more nerves and one or more lymphatic ducts traveling along a lumen coupling a first organ to at least a second organ in a body. In aspects, the blocking step prevents metastasis of a tumor from the first organ to the second organ in the body. In aspects, the first organ is a pancreas and the second organ is one of a spleen, a stomach, a gall bladder, a liver and a duodenum.

In aspects, the method provides that the blocking step further comprises applying energy to at least one of the nerves and lymphatic ducts. In aspects, the energy is thermal energy, radio frequency current, microwave current, ultrasound, radiation, cryotherapy, or a combination thereof.

In aspects, the method provides that the blocking step is performed at least in part by a substance. In aspects, the substance is a medicament, a denervating agent, a sympathetic nerve specific denervating agent, a parasympathetic nerve specific denervating agent, a neuroblocking agent, a highly specific neuroblocking agent, or a combination thereof.

According to aspects, a method is provided for treating neurogenic pathways associated with cancer progression.

BRIEF DESCRIPTION OF THE DRAWINGS

Several aspects of the disclosure can be better understood with reference to the following drawings. In the drawings, like reference numerals designate corresponding parts throughout the several views.

FIGS. 9a-9d show aspects of a device in accordance with the present disclosure.

FIGS. 10a-10n show aspects of distal tips associated with a device (e.g., guidewire, catheter, micro-tool, etc.) in accordance with the present disclosure.

DETAILED DESCRIPTION

Figure 1:
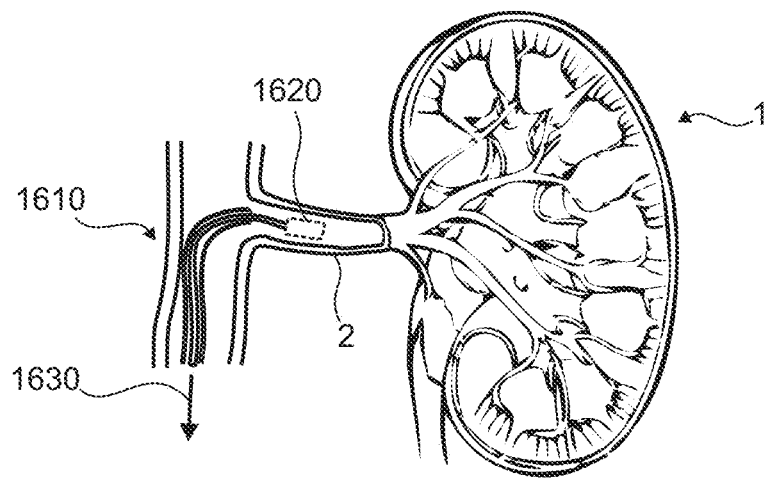
FIG. 1 shows aspects of a device in accordance with the present disclosure inserted into a lumen within a body coupled with a target organ.

Particular embodiments of the present disclosure are described herein with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes.

In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

According to a first aspect there is provided a controlled nerve ablation/neuromodulation system, which is configured for use in methods as described herein and may include the capability to sense one or more physiologic parameters at one or more points in the vicinity of a surgical site or within an affected/target organ, as well as include the capability to stimulate, deliver a chemical agent to, deliver energy to, and/or ablate tissues at one or more of the same points and/or an alternative point in the vicinity of a surgical site. The nerve ablation system may be configured so as to access vessels and/or surgical sites in the body. The non-limiting examples disclosed herein may be directed towards such configurations (e.g., to controllably provide neuromodulation procedures to an organ within a body, so as to controllably ablate renal nerves along a renal artery via an endoscopic or percutaneous procedure, to treat a cancerous tumor, to limit perineural invasion of cancerous cells into a nearby nerve, to alter a tumor microenvironment, etc.).

In aspects, a system/surgical tool in accordance with the present disclosure may be used to access, monitor, and/or to treat one or more neurological pathways, ganglia, and/or sensory receptors within a body: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. Such receptors may be associated with one or more organs and/or physiologic processes within the body (i.e., a regulatory process, etc.).

In aspects, a surgical tool in accordance with the present disclosure may take the form of a guidewire. The guidewire may be dimensioned and configured for placement within a lumen of a body at and/or beyond a surgical site and/or anatomical site of interest, so as to monitor one or more physiologic signals near the tip thereof. In aspects, the guidewire may provide a pathway for delivery of a second surgical device to the surgical site.

In aspects, a guidewire in accordance with the present disclosure may include one or more energy delivery means for delivering energy to an anatomical site within and/or beyond the wall of a lumen into which the guidewire tip has been placed.

In aspects, a guidewire in accordance with the present disclosure may include one or more sensors (e.g., as located on a micro-tool-tip, a clamp, a hook, a wire element, an electrode in a matrix, etc.) near to the tip thereof. One or more sensors may include a pressure sensor, a tonal sensor, a temperature sensor, an electrode (e.g., sized, oriented, and configured to interact with a local tissue site, provide a stimulus thereto, measure a potential therefrom, monitor current to/from the tissues, to measure, dependent on configuration and design, a bioimpedance, measure an evoked potential, an electromyographic signal [EMG], an electrocardiographic signal [ECG], an extracellular potential form a nearby neural structure, a mechanomyographic signal [MMG], local neural traffic, local sympathetic nerve traffic, local parasympathetic nerve traffic, afferent nerve traffic, efferent nerve traffic, etc.), an acoustic sensor, an oxygen saturation sensor, or the like.

In aspects, such sensing may be used in combination with a stress test, before/during/after an ablation, stimulation, administration of a chemical, or the like to assess the effect of the procedure on the neural traffic, tissue viability, or the like. Additional details relating to the sensing can be found in U.S. patent application Ser. No. 14/374,466, entitled "Controlled Sympathectomy and Micro-Ablation Systems and Methods," which is incorporated by reference herein.

In aspects, a guidewire in accordance with the present disclosure may include one or more analyte sensors, configured to measure one or more analyte concentrations or concentration trend before, during, and/or after a procedure within a body. Such analyte sensors may be provided in an electrochemical form, a fluorescent form, an electro-optical form, a swelling responsive gel, etc.

A sensing guidewire in accordance with the present disclosure may be advantageous for accessing very small anatomical sites within a body, accessing adjunct arteries and/or arteriole pathways along a blood supply to a target organ, accessing a plurality of vessels coupled to an organ, accessing the parenchyma of an organ, for highly localized interaction with a tissue site, for accessing otherwise challenging lumens (i.e., a lumen with substantially small diameter, with substantially tortuous shape, etc.). In aspects, a guidewire in accordance with the present disclosure may provide a means for directing one or more additional tools to a surgical site within a body. In aspects, a guidewire in accordance with the present disclosure may be configured to sense physiologic parameters from and/or to treat tissues within such miniature lumens as part of a procedure (i.e., a surgical procedure, a diagnostic procedure, an ablation procedure, etc.). Such a configuration may be particularly advantageous for accessing a vessel within a small organ or microvascular region of an organ, such as with a bone, near to a foramen of a bone, or the like.

In aspects, a system for treating a cancerous tumor coupled to a target organ within a body in accordance with the present disclosure may include a catheter (i.e., a balloon catheter, a needle catheter, a flexible catheter, etc.), or a guidewire, sized and dimensioned for delivery into a lumen (i.e., an artery, vein, vessel, or the like) serving the target organ, the catheter or guidewire including a distal tip configured to interface with the walls of an artery, vein, vessel coupled to the target organ, the distal tip configured for delivery of energy and/or a substance to one or more nerves coupled to the target organ.

In aspects, a system for augmenting function of a target organ within a body in accordance with the present disclosure may include a catheter (i.e., a balloon catheter, a needle catheter, a flexible catheter, etc.) or a guidewire, sized and dimensioned for delivery into a lumen (i.e., an artery, vein, vessel, or the like) serving the target organ, the catheter or guidewire including a distal tip configured to interface with the walls of an artery, vein, vessel coupled to the target organ, the distal tip configured for delivery of energy and/or a substance to one or more nerves coupled to the target organ. In aspects, the energy may be thermal energy, RF current, MW current, ultrasound, radiation, cryotherapy, or the like.

In aspects, the substance may be a neurolytic agent, a mild inflammatory agent, a medicament, a denervating agent, a sympathetic nerve specific denervating agent, a parasympathetic nerve specific denervating agent, a neuroblocking agent, a highly specific neuroblocking agent (i.e., an agent specifically configured for blocking of a particular receptor, nerve family, etc.), or the like. In aspects, the denervating agent may be ethanol, botulinum toxin, or the like. In aspects, the highly specific denervating agent may be a neural targeting chemical such as a poison, a toxin, or the like. In aspects, the neurolytic agent may be ethanol. In aspects, the mild inflammatory agent may be ethanol, poly (lactic-ω-glycolic acid) (PLGA), polysaccharides, collagen, silica particles, carbon micro or nanoparticles, microbeads, etc.

In aspects, the catheter or guidewire may include one or more sensing elements each in accordance with the present disclosure, located within the vicinity of the distal tip thereof, configured to interface and record physiologic information associated with one or more nerves coupled to the target organ upon placement (i.e., during a surgical or interventional procedure, during a diagnostic procedure, a stress test, etc.). In aspects, the catheter or guidewire may be equipped with a substance eluting element, configured to deliver a substance, a medicament, a denervating substance, or the like into the target organ, into the tissues surrounding the wall of the lumen, etc. In aspects, the energy and/or substance is delivered to interrupt and/or augment neural traffic along one or more nerves coupled to the target organ. In aspects, the energy and/or substance is provided so as to block nerve traffic to and/or from the organ along the lumen into which the distal tip has been inserted. In aspects, a system a system in accordance with the present disclosure may be used to treat pain, pain associated with perineural invasion of a cancerous tumor, or the like.

Some non-limiting examples of systems, devices, and methods which may be suitable for performing one or more aspects of a surgery, interventional procedure, diagnostic, and/or treatment in accordance with the present disclosure are generally detailed in co-pending international patent applications including International Publication Nos. WO 2014/070999, WO 2013/181137, WO 2013/112844, WO 2013/042847, WO 2013/067726, and WO 2014/031962, the disclosures of which are expressly incorporated herein by reference.

In aspects, a system, device, and/or method in accordance with the present disclosure may be used to treat and/or slow the progression of a cancerous tumor. Some non-limiting examples of such cancer that may be treated include cancer of the prostate, pancreas, breast, colon, skin, liver, esophagus, cervix, bone, urogenitals, lung, and the like.

In aspects, a system, device, and/or method in accordance with the present disclosure may be used to slow, hinder, and/or prevent perineural invasion of a cancerous tumor into a surrounding nerve structure. In aspects, a system, device, and/or method in accordance with the present disclosure may be used to interrupt, decrease, and/or stop neural communication to a cancerous tumor and/or the microenvironment surrounding the tumor (i.e., to interrupt nerve traffic to/from a cancerous tumor or the tissues thereby to the rest of the body). In aspects, a system, device, and/or method in accordance with the present disclosure may be used to decrease pain signals communicated by nerves in the vicinity of the organ and/or tumor to one or more neural circuits, ganglia, etc. In aspects, a system, device, and/or method in accordance with the present disclosure may be used to block, deaden, and/or to destroy nerves in the vicinity of a tumor and/or surrounding tissues.

In aspects, a system, device, and/or method in accordance with the present disclosure may be used to slow or even halt tumorigenesis of cancerous tissue.

In aspects, a system, device, and/or method in accordance with the present disclosure may be configured to form a physical barrier (i.e., lesion, a collagen block, etc.). In aspects, a system, device, and/or method in accordance with the present disclosure may be used to treat local inflammation (such as for the treatment of pancreatitis, prostatitis, irritable bowel syndrome, etc.).

In aspects, the system may include a balloon coupled with the catheter, situated in the vicinity of the distal tip thereof, the balloon coupled to a fluid source so as to be expand-ably deployed during a procedure so as to interface with the walls of lumen into which the distal tip has been placed. In aspects, the balloon may include one or more energy delivery elements, and/or sensing elements each in accordance with the present disclosure configured to interface with tissues adjacent to the balloon during a procedure. In aspects, the sensing elements may be configured to monitor electrophysiological information associated with the adjacent tissues.

In aspects, the system may be configured to direct energy through the energy delivery elements based upon the information collected by the sensing elements. In aspects, the sensing elements may be used to determine regions of abnormal electrophysiological activity, determine the direction of nerve traffic along the lumen, determine the type of nerves situated near the sensing element, etc. In aspects, the energy delivery may be directed to one or more regions of the lumen wall, through the lumen wall, into the adventitia in the vicinity of the lumen, into an organ (i.e., a pancreas, a liver, an intestinal wall, a kidney, a bone, etc.) adjacent to the lumen, etc. as directed by data collected by the sensing elements during the procedure.

In aspects, the system may include a stress testing aspect, configured to apply a stress (i.e., local and/or systemic) to the body while monitoring the response to the stress via one or more of the sensing elements. In aspects, the system may be used to diagnose a disease state, determine a function of the adjacent tissues, and/or determine the type of adjacent tissues (i.e., a nerve fiber, a type of nerve fiber, etc.) based upon the data obtained by the one or more sensing elements during the stress.

In aspects, a method in accordance with the present disclosure for treating a cancerous tumor, may include inserting at least a portion of a system in accordance with the present disclosure into a lumen with a wall in the vicinity of a target organ, and delivering energy and/or a substance to at least a portion of the wall of the lumen, through at least a portion of the wall of the lumen, into the target organ, and/or into the tissues surrounding the target organ. The method may include treating one or more nerves in the vicinity of the target organ.

In aspects, the method may include collecting physiologic data from the target organ and/or within the vicinity of the target organ, collecting data from one or more neural structures coupled to the organ, or the like. The method may include making a diagnostic decision, determining the state of the local neural structures, determining the extent of a surgical procedure, etc. based at least in part from the recorded data. In aspects, the method may include directing the energy and/or substance based upon the collected physiologic data. In aspects, the method may include collecting further physiologic data after the delivery of energy to determine if the desired effect has been achieved. In aspects, the method may include comparing a neural activity associated with the procedure, treatment, and/or target organ before and after a procedure, to determine the extent of the procedure, to confirm that the procedure positively affected the functionality of the nerves, etc.

In aspects, the substance may include an antibody drug conjugate (ADC), a chemotherapeutic agent, a toxin, a neurotoxin, etc. In aspects, the ADC substance may be configured to affect the function of a region or tissue type within the vicinity of the organ alternatively to the other tissues within the vicinity thereof. In aspects, the substance may include a sugar attached to a therapeutic agent to mask the therapeutic agent, such that it is to be taken up by the region of tissue (i.e., appear as a sugar, a friendly protein, etc.). Such a configuration provides a method for delivering a highly potent medicament directly to a tissue of interest (i.e., directly into a tumor), so as to enhance the bioavailability thereof, and to minimize the systemic dosage required in order to achieve significant therapeutic concentrations thereof within the region of tissue.

In aspects, the substance may be delivered at a rate of less than 1 mg/sec (milligrams/second), 1 mg/min (milligrams/minute), 1 mg/hr, 0.01 mg/hr, 1 µg/hr, or the like. Such a configuration may be important so as to minimize local stress and damage caused by the introduction of the substance into the microenvironment of the tissue of interest.

In aspects, a system in accordance with the present disclosure may include a catheter and/or a guidewire configured for percutaneous access to the arteries, veins, or lumens, of a body, for delivery through one or more arteries of the body to the vicinity of the target organ.

In aspects, one or more energy delivery elements, sensing elements, a diameter of the catheter, guidewire, or the like may be sized and arranged such that it may be placed within an artery, vein in a region near the target organ, within the parenchyma of the target organ, into a vessel in the periosteal space of a bone, and/or through a foramen of a bone. In aspects, the delivery elements and/or sensing elements, catheter, guidewire, etc. may be sized and dimensioned such that a characteristic diameter thereof is less than 1 mm, less than 0.75 mm, less than 0.5 mm, less than 0.3 mm, or the like.

According to aspects, there is provided a method for treating a tumor including stimulating, blocking, and/or ablating one or more regions of a neural circuit coupled to the tumor and/or perineural microenvironment surrounding a tumor. In aspects, the method may include performing the treatment without substantially increasing inflammation, necrotizing tissues, or the like in the vicinity of the tumor.

In aspects, the method may include stimulating the neural circuit with a stimulation frequency suitable to provide a neural block there along. In aspects, the method may include providing energy and/or a bolus of a chemical agent in an amount sufficient to provide a neural block to one or more regions of the neural circuit, and/or ablate one or more regions of the neural circuit.

In aspects, a system, device, and/or method in accordance with the present disclosure may be used to prevent or slow the growth rate and/or tumorigenesis of a cancerous tissue, modulating neural communication between a tumor and one or more neural circuits coupled to the target organ, augmenting/treating/ablating the perineural microenvironment in the vicinity of a tumor or along a neural circuit coupled thereto, and/or preventing or slowing the process of perineural invasion of a tumor into surrounding tissues In aspects, a method in accordance with the present disclosure for treating a tumor within a body may include neuromodulating one or more nerves coupled to the tumor. In aspects, a method in accordance with the present disclosure for treating a tumor within a body may include neuromodulating a perineural microenvironment in the vicinity of the tumor. In aspects, a method in accordance with the present disclosure for treating a tumor within a body coupled with a neural circuit within the body may include decoupling the neurological connection between the tumor and the neural circuit. In aspects, a method in accordance with the present disclosure may be used to treat prostate cancer, pancreatic cancer, breast cancer, colon cancer, cervical cancer, ovarian cancer, bladder cancer, or the like.

In aspects, a method in accordance with the present disclosure may include inserting the distal tip of a device in accordance with the present disclosure into a vessel coupled to the tumor. In aspects, the method may include placing the distal tip of a device into a vessel, such as an artery, which supplies blood to the tumor, and/or uniquely supplies blood to the organ coupled with the tumor.

In aspects, a method in accordance with the present disclosure may include applying energy and/or a chemical agent into an adventitia surrounding the vessel. In aspects, a method in accordance with the present disclosure may include monitoring electrophysiological activity along a wall of the vessel. In aspects, the method may include using the monitoring to determine the extent of a treatment, to alter a bolus of energy or chemical agent delivered, or the like.

In aspects, a method in accordance with the present disclosure for treating a tumor may include inducing apoptosis within neural tissues within the vicinity of the tumor, within a neural circuit coupled with the tumor, or the like.

In aspects, a method in accordance with the present disclosure may include inducing necrosis, and/or apoptosis within neural tissues within a neural circuit coupled with the tumor. In aspects, induced necrosis will typically cause the corresponding cells to exhibit rapid swelling, lose membrane integrity, shut down metabolism, and release their contents into the environment. Cells that undergo rapid necrosis in vitro do not often have sufficient time or energy to activate apoptotic machinery and thus will often not express apoptotic markers. Rather, induced apoptosis typically causes the corresponding cells to exhibit cytological and molecular events such as a change in the refractive index of the cell, cytoplasmic shrinkage, nuclear condensation, and cleavage of DNA into regularly sized fragments. In aspects, the chemical agent may be selected so as to induce apoptosis in one or more neural tissues (i.e., axon, dendrite, cell body, myelin sheath, synapse, etc.).

In aspects, one or more systems, methods, and devices each in accordance with the present disclosure may be used to interventionally alter one or more homeostatic processes within a body. Some non-limiting examples of homeostatic processes include production/release of renin, insulin, cholesterol, bile salts, testosterone, progesterone, prion, serotonin, endorphins, dopamine, monoamine neurotransmitters, histamines, noradrenaline, glucose, and the like, adjustment of blood pressure, anti-inflammatory activity, testosterone, estrogen, "uterine hemorrhaging", hunger, bowel movement, nutritional uptake in the bowel, and the like.

In aspects, a system in accordance with the present disclosure may include a substance delivery aspect, configured for elution of a substance into the vicinity of the target. In aspects, the system may include one or more sensing elements configured for monitoring of one or more physiologic parameters associated with the target, the homeostatic process in question, a stress response, or the like. In aspects, the system may include one or more energy delivery elements configured to deliver a bolus of energy to the target in order to alter the homeostatic process.

According to aspects, there is provided a method for blocking at least one of one or more nerves and one or more lymphatic ducts coupled to at least one of a tumor and a metastatic cell within a body. In aspects, the blocking step isolates at least one of the tumor and the metastatic cell within the body. In aspects, the blocking step alters growth rates of at least one of the tumor and metastatic cell within the body. In aspects, the blocking step is performed by injecting a neurolytic agent into at least one of the nerves, the lymphatic ducts and nearby tissue. In aspects, the blocking step includes injecting a mild inflammatory agent into at least one of the nerves and the lymphatic ducts. In aspects, at least one of the one or more nerves and at least one of the one or more lymphatic ducts being blocked is at least 10 mm, 20 mm, or 25 mm in length.

In aspects, injection of the mild inflammatory agent may be performed through the wall of the artery to minimize collateral damage to the surrounding tissues. In aspects, microneedles, either with or without sensing capability, may be inserted through the wall of the vessel. In aspects, the mild inflammatory agent may be delivered into the adventitia around the vessel, where the nerves are situated. In aspects, neural traffic may be sensed with sensing enabled microneedles (or other means if the microneedles do not have sensing capability). In aspects, the method includes determining whether the microneedles are close to the nerves, releasing the mild inflammatory agent when the microneedles are close to the nerves, monitoring the nerves (e.g., via changes in traffic), and pulling out the microneedles to finish the procedure.

In aspects, blocking may refer to the blocking of neural traffic along a nerve (such as via disrupting the function of the nerve at one or more sites thereupon, over stimulating the nerve so as to functionally block traffic thereupon, changing the electrical potentials around the nerve, altering the ionic concentrations in and/or around the nerve, and/or destroying one or more functional features of the nerve at one or more sites thereupon). In aspects, blocking may refer to physically blocking the channel taken up by the nerve (i.e. the physical space taken up by the nerves, which form channels through an associated tissue volume). Such physical blocking may be useful to limit axonal regrowth of the nerve after the procedure, to disrupt channel pathways, which may facilitate cell migration, or the like. For example, inflammation may be induced to close off the channels and limit or hinder nerve regrowth after the procedure.

In aspects, the method may include accessing at least one of the nerves and the lymphatic ducts via one of a nearby artery, a vein and a duct.

In aspects, the method provides that the blocking step further comprises altering the structure of a perineural sheath of one or more nerves. In aspects, the blocking step further comprises performing architectural destruction of at least one of nerve tissue and lymphatic ductal tissue via inflammation. In aspects, the blocking step further comprises forming scar tissue along at least one of the nerves and the lymphatic ducts.

In aspects, architectural destruction of at least one of nerve tissue and lymphatic ductal tissue may be effected by a mild inflammatory agent. In aspects, architectural destruction of at least one of nerve tissue and lymphatic ductal tissue may be effected by a dedicated ingredient in a substance, such as, but not limited to, silica and PLGA beads.

In aspects, the method provides that the blocking step further comprises using a single therapeutic compound. In aspects, the compound comprises one of an ablative agent, a migration limiting agent, and an inflammatory accelerating agent. In aspects, the blocking step treats at least one of a tumor, a metastasis migration and cancer pain.

In aspects, the method may include confirming completion of the blocking step. In aspects, confirmation is performed at least in part by at least one of a system, a device, and a sensor positioned within at least one of a nearby tissue site, an artery, a vein, and a duct.

In aspects, the method includes sensing neural traffic along the nerves at least one of before, during, and after the blocking step to at least one of locate the nerves and confirm completion of the block.

According to aspects, a method is provided for blocking at least one of one or more nerves and one or more lymphatic ducts traveling along a lumen coupling a first organ to at least a second organ in a body. In aspects, the blocking step prevents metastasis of a tumor from the first organ to the second organ in the body. In aspects, the first organ is a pancreas and the second organ is one of a spleen, a stomach, a gall bladder, a liver and a duodenum.

In aspects, the method provides that the blocking step further comprises applying energy to at least one of the nerves and lymphatic ducts. In aspects, the energy is thermal energy, radio frequency current, microwave current, ultrasound, radiation, cryotherapy, or a combination thereof.

In aspects, the method provides that the blocking step is performed at least in part by a substance. In aspects, the substance is a medicament, a denervating agent, a sympathetic nerve specific denervating agent, a parasympathetic nerve specific denervating agent, a neuroblocking agent, a highly specific neuroblocking agent, or a combination thereof.

According to aspects, a method is provided for treating neurogenic pathways associated with cancer progression.

FIG. 1 shows aspects of a device in accordance with the present disclosure inserted into a lumen within a body coupled with a target organ. A micro surgical tool 1610 in accordance with the present disclosure is shown as placed into the renal artery 2 of a subject as coupled to a target organ 1 (i.e., here shown as a kidney) in accordance with the present disclosure. In aspects, the microsurgical tool 1610 may include one or more distal tips 1620 each including one or more sensing tips in accordance with the present disclosure to selectively sense, stimulate, and/or treat target anatomy based on the determined locations thereof. In aspects, the sensing tips may be configured to acquire positional and/or physiologic information related to the target anatomy, placement of the micro surgical tool 1610 within the renal artery 2, the parenchyma of the target organ 1, and/or monitoring of the surgical procedure (i.e., ablation procedure, chemical denervation, chemical deployment, etc.), or the like. Such a feedback mechanism may be used to precisely guide the micro surgical tool 1610 during a surgical procedure (i.e., ablation procedure, etc.), to determine the extent of a surgical procedure, or the like. In aspects, the distal tip 1620 may be coupled with a controller 1630 in accordance with the present disclosure for performing one or more of the procedures.

Figure 2:
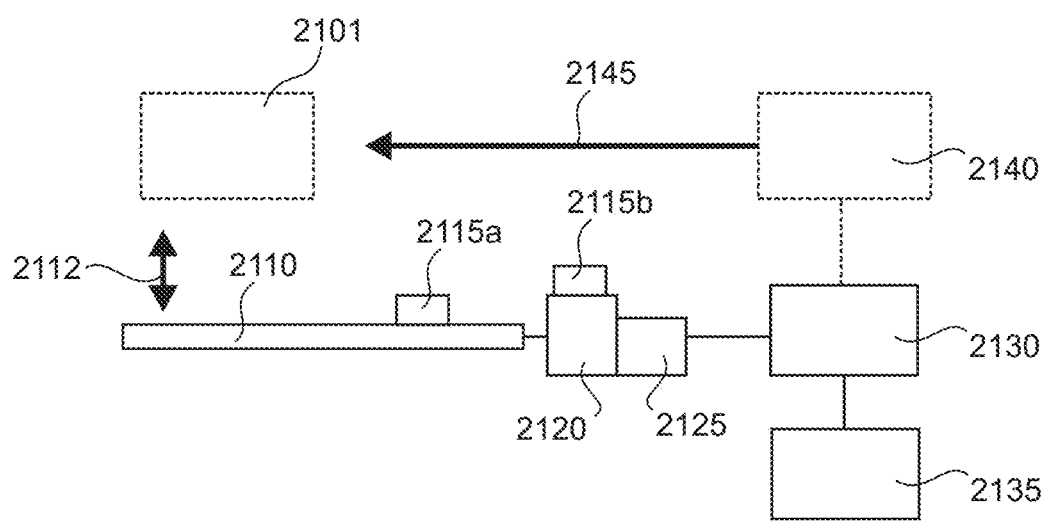
FIG. 2 shows a schematic of aspects of a system in accordance with the present disclosure.

FIG. 2 shows a schematic of aspects of a system for performing a surgical procedure in accordance with the present disclosure. The system is shown interfacing with a surgical site 2101 within a body, a subject, a patient, etc. The system may include a microsurgical tool 2110 in accordance with the present disclosure. During use, the microsurgical tool 2110 may be configured to interact 2112 with the surgical site 2101 in accordance with the present disclosure. In aspects, the microsurgical tool 2110 may be coupled to a connector 2120, the connector providing a mechanical and/or electrical interface between the microsurgical tool 2110 and/or one or more other modules of the system. In aspects, the microsurgical tool 2110 may include an embedded local control circuit 2115a (e.g., a microcircuit, a switch network, a signal conditioning circuit, etc.) in accordance with the present disclosure. In aspects, the connector 2120 may include a local control circuit 2115b in accordance with the present disclosure. In aspects, the connector 2120 may be coupled to an operator input device 2125 (i.e., a foot pedal, an advancing slider, a torqueing mechanism, a recording button, an ablation button, etc.). In aspects, the connector 2120 may be coupled to a control unit 2130 configured to accept one or more signals from the microsurgical tool 2110, communicate one or more control signals thereto, send one or more pulsatile and/or radio frequency signals to the microcontroller, record one or more electrophysiological signals from the microsurgical tool, or the like.

In aspects, the control unit 2130 may be connected to a display 2135 configured to present one or more aspects of the recorded signals from the microsurgical tool 2110 to an operator, to present a map, at least partially dependent on the recorded signals, to present one or more metrics relating to a physiologic parameter, a surgical procedure, surgical outcome efficacy, etc. In aspects, the control unit 2130 may be coupled to a surgical subsystem 2140, the surgical subsystem 2140 configured to perform a surgical procedure 2145 to the surgical site 2101. Some non-limiting examples of suitable surgical procedures include an ablation, an excision, stimulation, a cut, a burn, a radio frequency ablation, radiosurgery, an ultrasonic ablation, an abrasion, a biopsy, and delivery of a substance. The control unit 2130 may be configured to influence, direct, control, and/or provide feedback for one or more aspects of the surgical procedure 2145, based upon one or more of the electrophysiological signals conveyed by the microsurgical tool 2110.

Figure 3A:
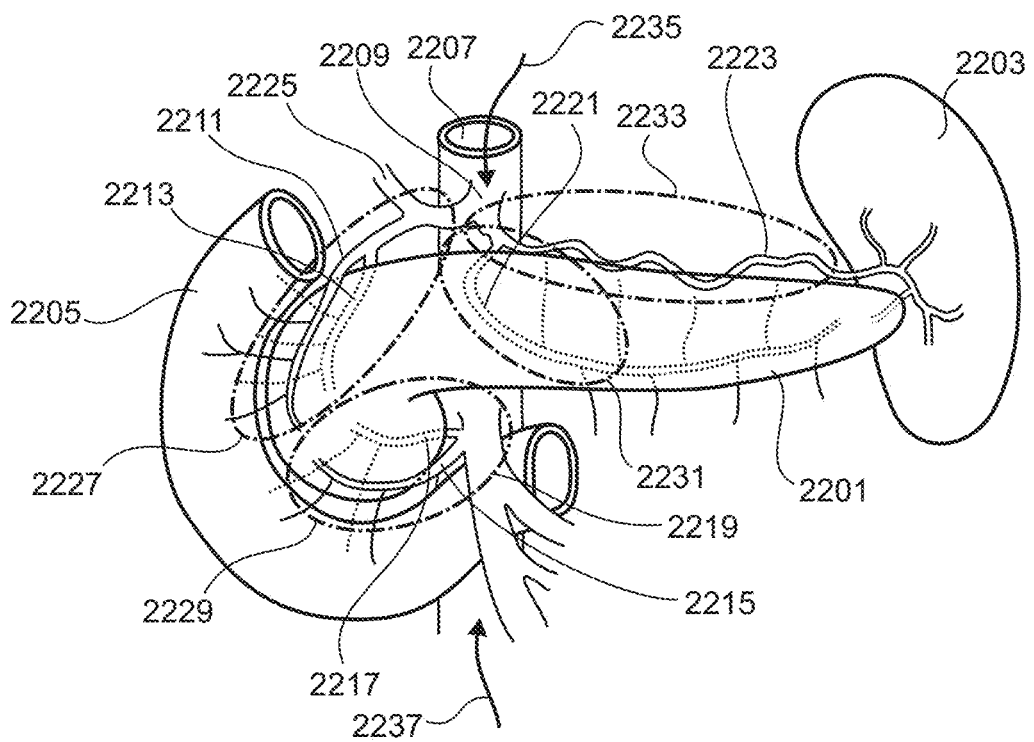
FIGS. 3a-3c show aspects of access and treatment regions for a target organ in accordance with the present disclosure.
Figure 3B:
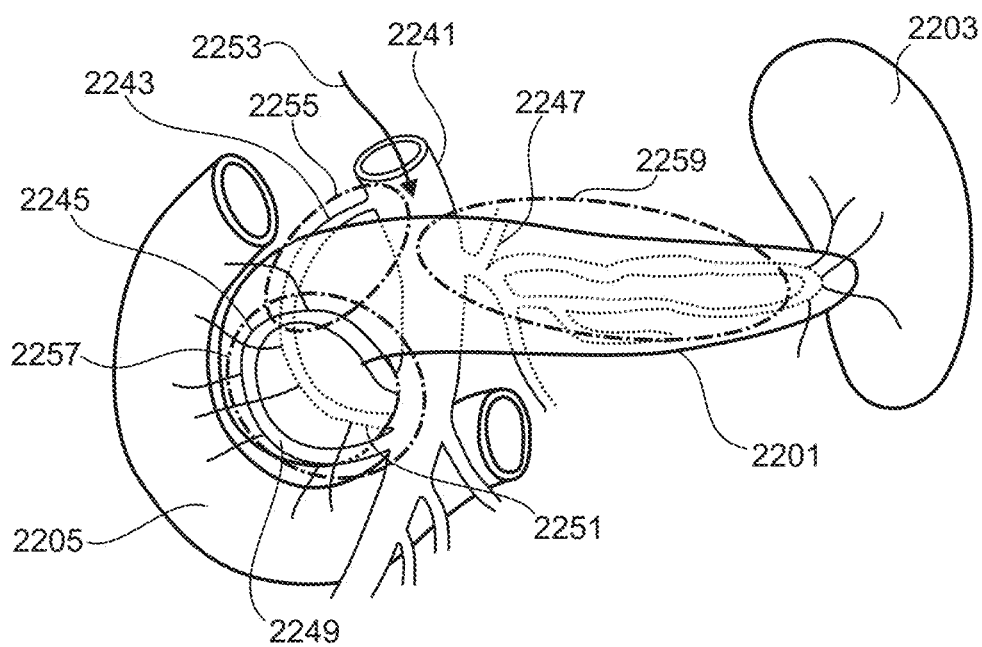
Figure 3C:
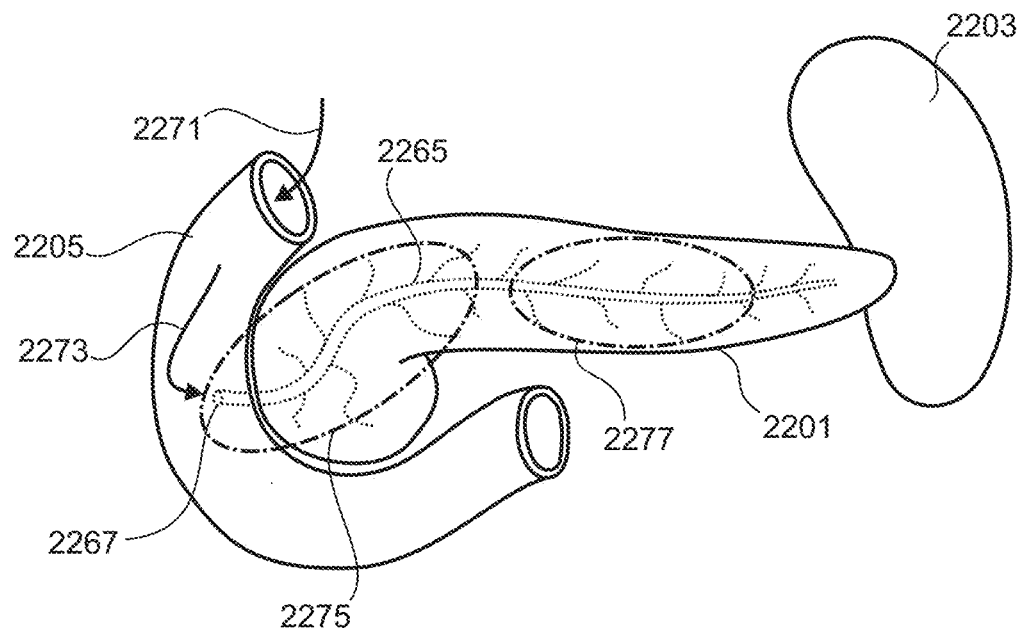

FIGS. 3a-3c show aspects of access and treatment regions for a target organ in accordance with the present disclosure. Each of FIGS. 3a-3c show a pancreas 2201 (i.e., a target organ in accordance with the present disclosure), a spleen 2203 (i.e., optionally a target organ in accordance with the present disclosure), and a duodenum 2205. FIG. 3a illustrates aspects of a vascular supply to the pancreas 2201, spleen 2203, and duodenum 2205, including the aorta 2207, the celiac trunk 2209, the anterior superior pancreaticoduodenal artery 2211, the posterior superior pancreaticoduodenal artery 2213, the anterior inferior pancreaticoduodenal artery 2215, the posterior inferior pancreaticoduodenal artery 2217, the superior mesenteric artery 2219, the dorsal pancreatic artery 2221, and the splenic artery 2223. As part of a treatment, monitoring session, etc. in accordance with the present disclosure, one or more microsurgical tools each in accordance with the present disclosure may be inserted into and/or interfaced with one or more of the vascular supply vessels to the pancreas 2201, spleen 2203, and/or duodenum 2205. In aspects, one or more of the microsurgical tool tips may be delivered through the aorta 2207, the celiac trunk 2209, and/or the superior mesenteric artery 2219, or branches thereof, etc. In aspects, one or more microsurgical tools in accordance with the present disclosure may be configured to treat the perivasculature in the vicinity of one or more of the vascular supply lumens in accordance with the present disclosure.

In aspects, a pancreatic tumor may be present within or coupled with the pancreas 2201. In such aspects, a microsurgical tool in accordance with the present disclosure may be interfaced with one or more of the vascular supply lumens in order to treat the pancreatic tumor in accordance with the present disclosure.

In aspects, the treatment may be applied to one or more neurological structure in the vicinity of the vascular supply. In aspects, a procedure (i.e., a treatment, biopsy, sensing, stimulation, etc.) may be applied to a first zone 2227 located in the vicinity of the posterior and/or anterior superior pancreaticoduodenal arteries 2211, 2213. In aspects, such a zone may be located along the posterior and/or anterior pancreaticoduodenal arteries 2211, 2213 distally to the hepatic artery 2225. In aspects, a procedure in accordance with the present disclosure may be performed on a second zone 2229 located in the vicinity of the anterior and/or posterior inferior pancreaticoduodenal arteries 2215, 2217 in accordance with the present disclosure. In aspects, the second zone 2229 may include tissues in the vicinity and/or wall of the superior mesenteric artery 2219. In aspects, a procedure in accordance with the present disclosure may be performed on a third zone 2231, located in the vicinity of the dorsal pancreatic artery 2221 or tributaries formed therefrom. In aspects, a procedure in accordance with the present disclosure may be performed on a fourth zone 2233, located in the vicinity of the splenic artery 2223 or tributaries formed therefrom. In aspects, one or more zones 2227, 2231, 2233 may include regions of the celiac trunk 2209. In aspects, a surgical procedure may be applied simultaneously within one or more zones 2227, 2229, 2231, 2233, and/or vascular supply lumens, etc. In aspects, one or more distal tips of one or more surgical tools may be inserted into a zone 2227, 2229, 2231, 2233 as part of a procedure in accordance with the present disclosure.

In aspects, a plurality of distal tips may be simultaneously located within one or more zones. Energy provided via one or more of the distal tips may be communicated between zones 2227, 2229, 2231, 2233, and/or to an externally coupled component (i.e., an electrode). In aspects, the distal tips may be configured to perform a first procedure (i.e., a sensing procedure) within a first zone 2227, 2229, 2231, 2233 and to perform a second procedure (i.e., a stimulation, ablation, chemical delivery, etc.) within a second zone 2227, 2229, 2231, 2233, or the like.

In aspects, such procedures may be performed to augment and/or plastically change neural communication to/from one or more regions of a target organ 2201 to the brain, a ganglion, etc. so as to influence the physiologic function thereof, to augment the afferent traffic to the brain, to augment the efferent traffic reaching the target organ, etc.

In aspects, a procedure may be applied to the celiac trunk 2209, the third zone 2231, and/or the fourth zone 2233 in order to affect function of the spleen 2203.

In aspects, coordination of two or more procedures applied within one or more zones 2227, 2229, 2231, 2233 may be provided to treat one or more regions of the target organ 2201 (i.e., in this case so as to selectively treat one or more regions of the pancreas 2201 while maintaining regular function of one or more other regions of the pancreas 2201, etc.). In aspects, the zones 2227, 2229, 2231, 2233 to be treated may be selected based upon an image of the target organ 2201 (i.e., to determine the location and coupling of an anomaly, a tumor, etc. within the target organ 2201). In aspects, a first procedure, such as sensing and/or stimulation, applied within one or more of the zones 2227, 2229, 2231, 2233 may be provided to determine where within the target organ to provide a second procedure (i.e., sensing, ablation, etc.), or to determine the extent of a previously applied procedure (i.e., an ablation procedure, a neuromodulation procedure, etc.).

In aspects, the zones and/or anatomical features shown in FIG. 3a may be accessed through the aorta 2207, such as from a descending approach 2235 or an ascending approach 2237 as preferred by a surgeon or surgical planner.

FIG. 3b shows aspects of a pancreas 2201, a spleen 2203, and a duodenum 2205 along with the vascular supply thereto. Aspects of the vascular supply shown include the portal vein 2241, the posterior superior pancreaticoduodenal vein 2243, the anterior superior pancreaticoduodenal vein 2245, the splenic vein 2247, the anterior inferior pancreaticoduodenal vein 2249, and the posterior inferior pancreaticoduodenal vein 2251. Aspects of the tributaries that serve the vascular supply are shown as line segments interconnecting the larger vessels with the pancreas 2201, the spleen 2203, and the duodenum 2205.

In aspects, one or more zones 2255, 2257, 2259 may be accessed as part of a procedure and monitored, stimulated, treated, etc. in accordance with the present disclosure. In aspects as part of a method in accordance with the present disclosure, one or more of the zones 2255, 2257, 2259 may be accessed via a portal vein approach 2253 (i.e., via a catheter, guidewire, surgical tool, etc. placed into the portal vein). In aspects, one or more zones 2255, 2257, 2259 may be accessed via direct needle stick into the body as part of a procedure.

In aspects, one or more treatments may be applied to one or more of the zones 2255, 2257, 2259 as part of a procedure. Such treatments may be provided so as to affect the perineural microenvironment surrounding a tumor within the target organ, to affect one or more receptors, sensory nerves, or the like within the target organ, to affect one or more physiologic functions of the organ, etc.

FIG. 3c illustrates a pancreas 2201, spleen 2203, and a duodenum 2205, and a pancreatic duct 2265 running through the length of the pancreas 2201. The pancreatic duct 2265 supplies pancreatic fluids into the duodenum via the duodenal papilla 2267. In aspects, a system and/or method in accordance with the present disclosure may be used to treat one or more zones 2275, 2277 within the vicinity of the pancreatic duct 2265. In aspects, a surgical tool in accordance with the present disclosure may be introduced 2273 into the pancreatic duct 2265 via the duodenal papilla 2267, from a descending approach 2271 through the esophagus, stomach, and duodenum 2205.

In aspects, one or more of the zones 2275, 2277 may be monitored, and/or treated in accordance with the present disclosure. In aspects, such treatment may be used to affect secretion of pancreatic fluid into the duodenum 2205, affect cell function within the vicinity of the pancreatic duct 2265, affect the microenvironment of a tumor located within the pancreas 2201, to disconnect one or more neural pathways between a tumor and another neural circuit within the body, etc. In aspects, one or more of the treatments may be provided as part of a surgical procedure coupled with a pancreas resection, as part of a surgical intervention to treat pancreatic cancer, etc. In aspects, one or more treatments (i.e., stimulations, ablations, chemical agent delivery, neural blocks, etc.) may be configured to influence one or more functions of the target organ. In the case of the pancreas 2201, the treatments may be employed to affect one or more functions such as production of insulin, glucagon, somatostatin, and/or pancreatic polypeptide, production/secretion of pancreatic juice containing digestive enzymes, glucose metabolism, and/or control of blood glucose concentration.

Generally speaking, the part of the pancreas with endocrine function is made up of approximately a million cell clusters called islets of Langerhans. Four main cell types exist in the islets: α cells secrete glucagon (increase glucose in blood), β cells secrete insulin (decrease glucose in blood), delta cells secrete somatostatin (regulates/stops α and β cells) and PP cells, or gamma cells, secrete pancreatic polypeptide.

Secretion of hormones into the blood may be affected and/or regulated by the effect of hormones in the blood on the islets of Langerhans, and through the effect of the autonomic nervous system on the blood flow and cell function. In aspects, augmentation of sympathetic and/or parasympathetic activity may affect secretion from beta cells, and alpha cells within the pancreas.

Figure 4:
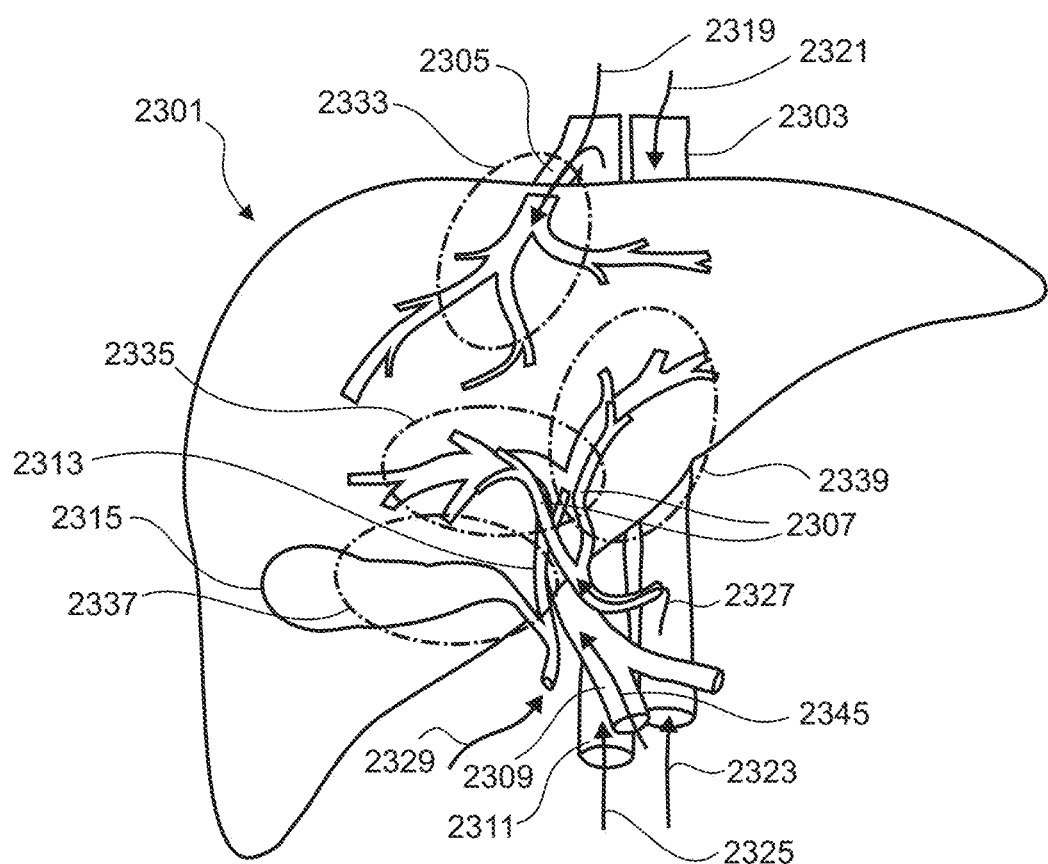
FIG. 4 shows aspects of access and treatment regions for a target organ in accordance with the present disclosure.

FIG. 4 shows aspects of access and treatment regions for a target organ in accordance with the present disclosure. A schematic diagram of a liver 2301, along with coupled vasculature including an aorta 2303, a hepatic vein 2305, hepatic arteries 2307, a portal vein 2309, and ducts including hepatic ducts 2313. A gallbladder 2315 is also shown, and may serve as a target organ for a procedure in accordance with the present disclosure. A plurality of zones 2333, 2335, 2337, 2339 may be accessed via the vasculature and/or ducts, and may be monitored and/or treated as part of a procedure in accordance with the present disclosure. In aspects, different neural circuits (sympathetic, parasympathetic, and/or afferent circuits), may travel through the various zones 2333, 2335, 2337, 2339. A monitoring procedure, optionally combined with a stress test, may be used to elucidate the type and/or function of neural circuits within the vicinity of one or more zones 2333, 2335, 2337, 2339, within a sub-region of a zone 2333, 2335, 2337, 2339, or the like.

In aspects, one or more neural circuits coupled with the liver 2301 may be selectively treated in accordance with the present disclosure. In aspects, one or more neural circuits passing along a hepatic duct 2313 may be monitored and/or treated in accordance with the present disclosure. In aspects, a hepatic duct 2313 situated zone 2337, or a zone 2335, 2339 situated in the vicinity of the hepatic arteries 2307 may be accessed through a hepatic duct 2313 approach 2329, and/or via an ascending approach 2323 through the aorta 2303, a descending approach 2321 through the aorta 2303, an ascending approach 2345 through the portal vein 2309, an ascending approach 2325 through the inferior vena cava 2311, and potentially a descending approach 2319 through the inferior vena cava 2311.

In aspects, one or more procedures in accordance with the present disclosure may be applied to the liver 2301, the parenchyma of the liver 2301, hepatocytes of the liver 2301, to disruption and/or augmentation of signals that can be relayed electrically to individual cells by structures such as cell-to-cell connecting gap junctions, to gap junctions within cells of the parenchyma (i.e., via modulation of electrotonic coupling, to compensate for the sparse direct inputs to the hepatocytes, especially with respect to sympathetic signal transduction), one or more zones 2333, 2335, 2337, 2339, within regions of receptors within the liver 2301 so as to modulate hormone release into the organ, one or more vessels and/or perivascular regions coupled with the liver 2301, and/or the gallbladder 2315 to treat a disease state, to augment organ function, or the like.

Some aspects of liver function that may be augmented by a treatment and/or monitored in accordance with the present disclosure include glucose storage/release, metabolic sensing (and related signal traffic to the brain related thereto), glucoregulatory function, afferent vagal activity reaching the brain, chemoreceptor function (or related signal traffic associated therewith), lipid sensing/synthesis, regulation of hepatic insulin sensitizing substance, afferent traffic augmentation associated with glucosensors (i.e., primarily in the region of the portal vein 2309, etc.), protein sensing, GLP-1, leptin, CCK, FFA, PPAR alpha and gamma, glycogenolysis, gluconeogenesis, VLDL secretion, ketogenesis, hypoglucemia sensing, or the like.

In aspects, one or more procedures (i.e., sensing, a treatment, stimulation, ablation, etc.) may be applied to one or more vagal branches including the hepatic branch, the gastroduodenal branch, the common hepatic branch, coupled with the left vagal and right vagal nerve branches. In aspects, such procedures may be performed along the associated vasculature serving the liver 2301 and/or within the parenchyma of the liver 2301 in the vicinity of the corresponding neural structures of the vagal branch in question. In aspects, monitoring of the vagal branch at a first location (i.e., along an artery supplying the liver 2301) and at a second location (i.e., at a site within the parenchyma of the liver 2301) may be used to confirm proper placement of a surgical tool at a treatment site, confirm efficacy of a treatment, confirm proper targeting of the associated neural structures related to the vagal branch, etc.

In aspects, one or more sympathetic procedures in accordance with the present disclosure may be applied to one or more sympathetic and/or afferent nerves in the vicinity of the liver 2301, the gallbladder 2315, along a vessel or duct serving the organs, etc.

In aspects, one or more surgical tools in accordance with the present disclosure may be used to provide a physical and/or functional mapping of one or more neural circuits within one or more regions of the liver neuronal network, such as to determine location and/or function of parasympathetic postganglionic cell bodies, response to stress tests, distinguish between sensory and motor neuron nerves, or the like.

Figure 5:
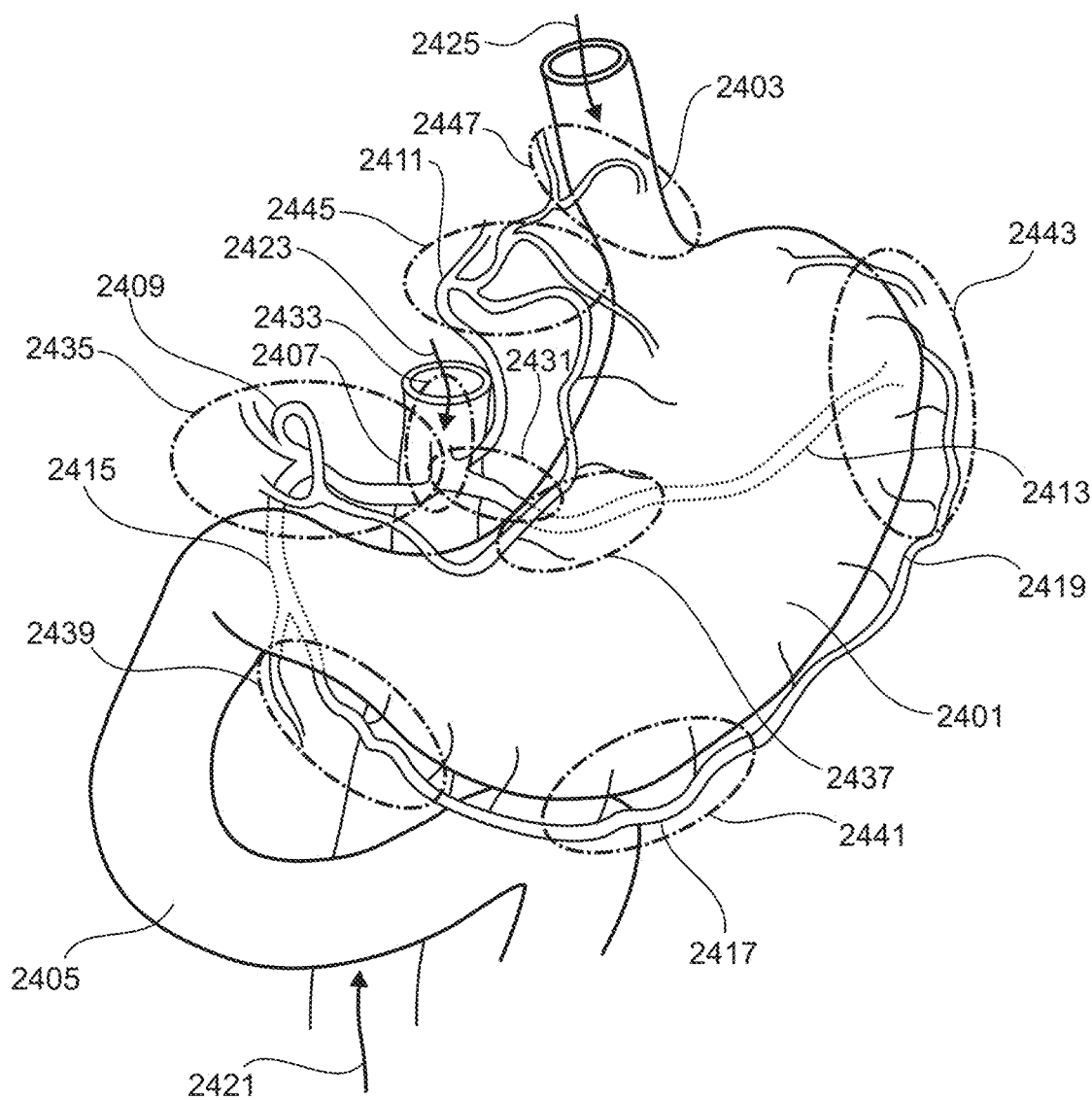
FIG. 5 shows aspects of access and treatment regions for a target organ in accordance with the present disclosure.

FIG. 5 shows aspects of access and treatment regions for a target organ in accordance with the present disclosure. The target organ is a stomach 2401. Also shown is the esophagus 2403, duodenum 2405, aorta 2407, the right gastric artery 2409, the left gastric artery 2411, the splenic artery 2413, the gastric duodenal artery 2415, the right gastroepiploic artery 2417, and the left gastroepiploic artery 2419. Access to one or more vessels coupled with the stomach may be provided via an ascending approach 2421 in the aorta 2407, via a descending approach 2423 in the aorta 2407, or via a descending approach 2425 in the esophagus 2403.

In aspects, one or more neural structures may be monitored and/or treated on the wall of the stomach 2401, the esophagus 2403, the duodenum 2405, and/or one or more of the vessels coupled thereto. In aspects, a procedure may be applied in the vicinity of one or more zones 2431, 2435, 2437, 2439, 2441, 2443, 2445, 2447 so as to treat a neurological disorder, function, etc. associated with the target organ 2401.

In aspects, a procedure and/or selective treatment may be applied to a neural structure, an afferent nerve, an efferent nerve, one or more sympathetic nerves (SNS), or the like in the vicinity of zones 2431, 2433, 2435, 2437, 2439, 2441, 2443, 2445, 2447 and/or parasympathetic nerves (PNS) in the vicinity of zones 2433, 2437, 2445, 2447. In aspects, a treatment may be applied selectively to SNS or PNS in order to balance a regulatory imbalance in the activity there between, or to create an imbalance in activity there between in order to augment function of the target organ, etc.

Figure 6:
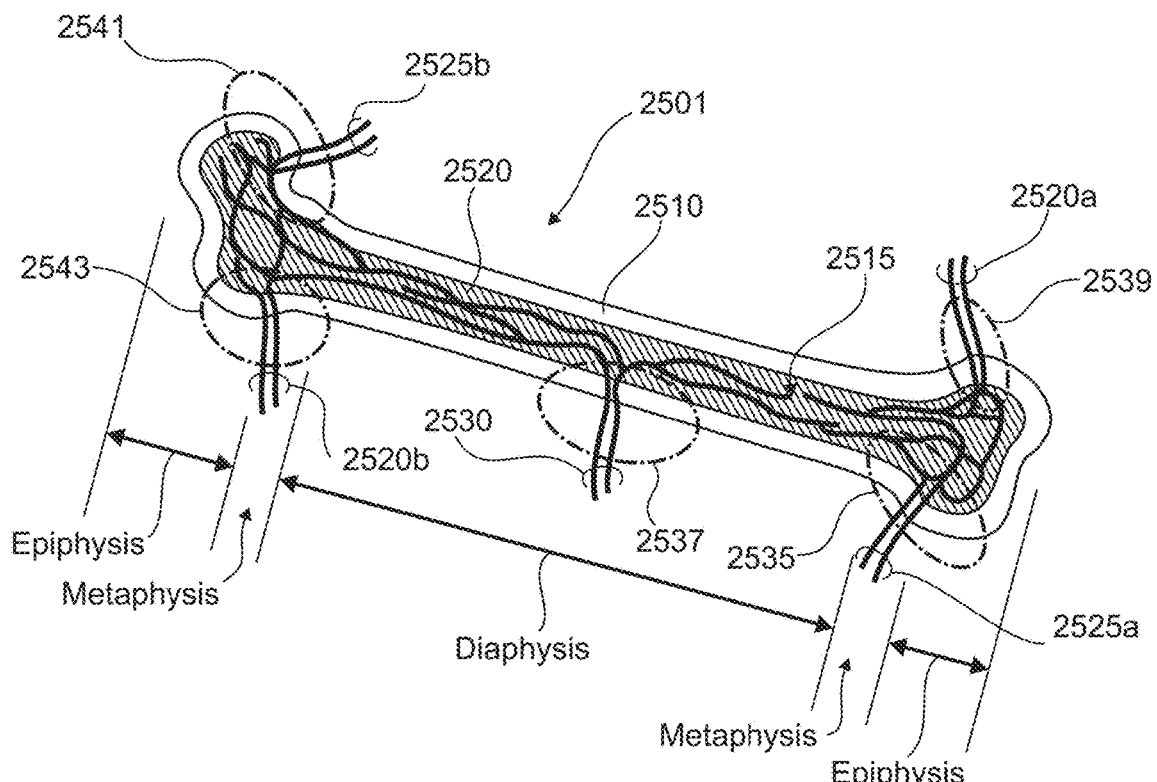
FIG. 6 shows aspects of access and treatment regions for a target organ in accordance with the present disclosure.

FIG. 6 shows aspects of access and treatment regions for a target organ in accordance with the present disclosure. The target organ shown is a femur bone 2501 (i.e., a representative non-limiting example of a long bone). The femur 2501 generally includes a diaphysis, metaphysis, and epiphysis regions. The treatment may be directed towards a bone related homeostatic function (e.g., osteoblast production), and/or one or more neural structures coupled with a tumor within one or more of the regions. The femur 2501 includes regions of compact bone 2510, spongy bone 2520, and a medullary cavity 2515 in which spongy bone 2520 is innervated with nerves, and vascularized with associated blood vessels. Exemplary epiphyseal arteries and veins 2520a, 2520b, metaphyseal arteries and veins 2525a, 2525b, and a nutrient artery and vein 2530 are highlighted. A system in accordance with the present disclosure may be sized and dimensioned such that a distal tip thereof may be advanced along an access point into one or more of the epiphyseal, metaphyseal, or nutrient arteries or veins 2520a, 2520b, 2525a, 2525b, 2530 to treat one or more regions of the femur 2501.

In aspects, one or more neural structures may be monitored and/or treated on one or more walls of the epiphyseal artery/vein 2520a, 2520b, metaphyseal artery/vein 2525a, 2525b, and/or the nutrient artery/vein 2530, within the medullary cavity 2515, within one or more sites of the spongy bone 2520, near to the foramen of the femur 2501, within the periosteal space of the femur 2501, and/or one or more of the vessels coupled thereto. In aspects, a procedure may be applied in the vicinity of one or more zones 2535, 2537, 2539, 2541, 2543 so as to treat a neurological disorder, a tumor, pain signals sent between the target organ 2501 and the body, treatment of neural receptors, a homeostatic function, etc. associated with the femur 2501.

In aspects, a procedure and/or selective treatment may be applied to a neural structure, an afferent nerve, an efferent nerve, one or more sympathetic nerves (SNS), parasympathetic nerves (PNS), motor nerves, receptors, and/or the like in the vicinity of zones 2535, 2537, 2539, 2541, 2543. In aspects, a treatment may be applied selectively to SNS or PNS in order to balance a regulatory imbalance in the activity there between, or to create an imbalance in activity there between in order to augment one or more functions of the femur, etc. In aspects, the procedure may be used to treat pain associated with bone cancer, to augment the microenvironment around a bone cancer tumor so as to alter the growth rate thereof, to adjust the production rate of osteoblasts, to alter the bone density, or the like.

Figure 7A:
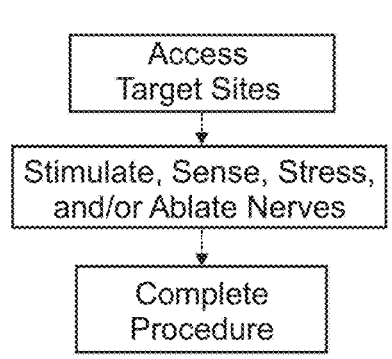
FIGS. 7a-7c show aspects of methods for treating and/or assessing function of a neural structure in accordance with the present disclosure.
Figure 7B:
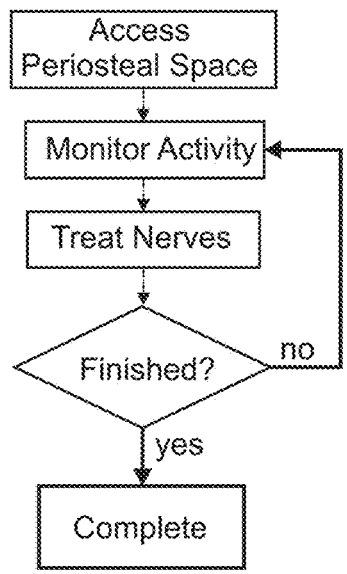
Figure 7C:
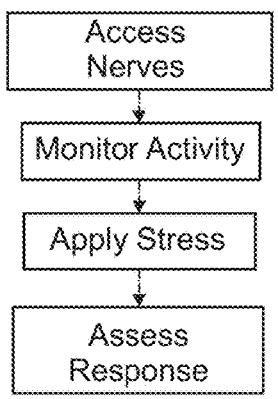

FIGS. 7a-7c show aspects of methods for treating and/or assessing function of a neural structure in accordance with the present disclosure. FIG. 7a illustrates aspects of a method for modulating or assessing neural traffic in accordance with the present disclosure. The method includes accessing one or more target sites within a body, stimulating, sensing, or ablating the nerves, augmenting neural activity, treating the afferent nerves and/or receptors, and optionally evaluating the afferent nerve activity post treatment to determine if the traffic has been modulated. In aspects, the evaluation may be performed by comparing a nerve activity metric before and after treatment (e.g., a change in integrated activity level, a change in phasic response such as a shift from a biphasic polarity to a monophasic polarity, a change in action potential firing rate, a change in the spectral content of the firing, etc. associated with the local neural tissues). In aspects, the method may include varying a pressure applied to the afferent nerves and/or receptors and monitoring afferent nerve activity during such changes in applied pressure (i.e., monitoring activity during a variable pressure compression block).

Additionally, alternatively, or in combination with the monitoring of electrophysiological activity, the method may include monitoring one or more physiologic parameters in accordance with the present disclosure and assessing changes in the parameters before, during, or for a period of time following application of a procedure to the target tissues.

One or more of the steps may be completed with a guidewire or surgical tool in accordance with the present disclosure.

FIG. 7b shows aspects of a method for treating one or more neural structures in a periosteal space in a bone in a subject. The method including accessing the periosteal space of the bone (e.g., via one or more vessels coupled thereto), optionally monitoring activity in one or more regions around the periosteal space, treating the nerves, and assessing based on a change in the activity if the treatment was successful. In aspects, the assessment may be determined based on a change in activity level (e.g., pulses per unit of time, drop out of pulses associated with a particular nerve type, changes in traffic associated with a neural circuit biorhythm, etc.), a shift in the polarity of the signals (i.e., a transition from a biphasic signal related to multi-directional traffic near the vessel, to a monophasic signal related to changes more representative of a uni-directional traffic near the vessel), a drop off in periodic behavior in the captured signals, or the like. In aspects, the, assessment may be determined by combining and/or comparing activity measured at multiple sites around the periosteal space, associated vessels, or the like. Such comparison may include assessing a change in coherence between two signals collected from different nearby sites, a change in one signal with respect to the other signal collected from nearby sites, a change in a representative transfer function representative of a correlation between the traffic at one site and the other site, etc.

The assessment may include determining if a change in one or more homeostatic functions of the organ have changed in a desired direction, if the response of the neural traffic to a stress test has changed as desired by the therapy, assessing if the subject feels the same, increased, or decreased pain compared with an assessment made before the procedure. If the treatment has been finished, complete the procedure, pull out any system component in the subject, etc. otherwise, monitor activity, continue with treatment, and/or move to a new treatment site in the vicinity of the bone (i.e., exemplary organ).

FIG. 7c illustrates a method for assessing the neural structures in the vicinity of a target organ. The method includes accessing (i.e., such as communicating with) the nerves associated with the target organ, disease state to be treated, etc. The method may include monitoring an initial activity level, signal character, periodic element to a signal, afferent or efferent traffic proportion of the neural traffic, etc. The method may include monitoring such activity or metrics associated there with during a stress test as applied to the organ, or subject as a whole. The method may include generating and/or analyzing a metric associated with the change in the monitored activity and determining a suitability of the subject for performing a surgical procedure, determining a proportion of nerve types amongst the captured responses, determining if the nerves require treatment, determining the influence of the stressor on the locally measured electrophysiological activity, or the like.

The method may include modulating a functionality of, neural activity from, afferent activity from, or the like of the target organ of a subject, the method may include selectively stimulating and/or stressing one or more regions of the target organ and monitoring the physiologic response at one or more sites nearby and/or systemically to the stimulus/stress. In aspects, the stimulus/stress response may be used to identify regions of the target organ that are suitable for neuromodulation to treat a particular condition. In aspects, the method may include selectively treating one or more sites within or in the vicinity of the target organ. In aspects, the method may include monitoring activity and/or local physiologic response to the treatment at one or more of the sites to determine the extent of the procedure, to evaluate when the procedure has been completed, to decide whether or not to continue with the procedure, etc. The method may include ablating a portion of the organ, or a neurological structure coupled thereto, in accordance with the present disclosure. In aspects, the method may include using a guidewire and/or surgical device in accordance with the present disclosure to perform one or more of the above steps.

In aspects, an ablation may be performed so as to minimize damage to surrounding tissues. The ablation may include delivering energy to the local tissues in an amount just sufficient to induce irreversible damage to one or more adjacent nerves, but not in an amount sufficient to irreversibly damage other surrounding tissues.

In aspects, the method may include dragging one or more electrode arrays in accordance with the present disclosure along a lumen in the vicinity of the target organ in order to locate neurological features of interest associated with the organ, locate one or more baroreceptors, map activity thereof, map functional changes thereof due to application of a treatment or stress thereto, evaluate the function thereof, and/or treat one or more such structures.

Figure 8A:
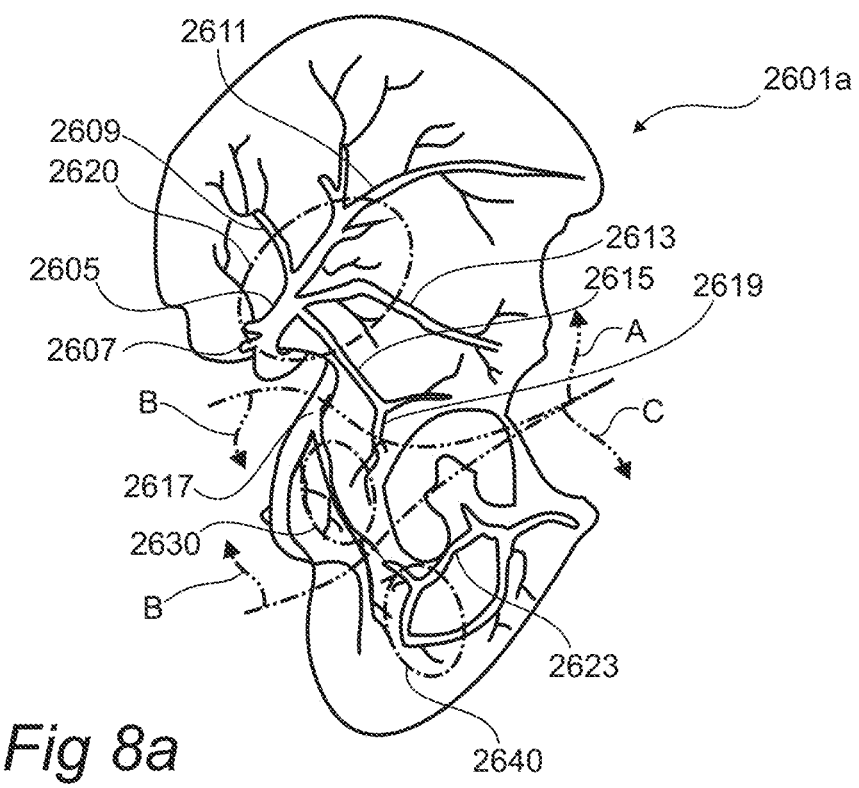
FIGS. 8a and 8b show aspects of access and treatment regions for a target organ in accordance with the present disclosure.
Figure 8B:
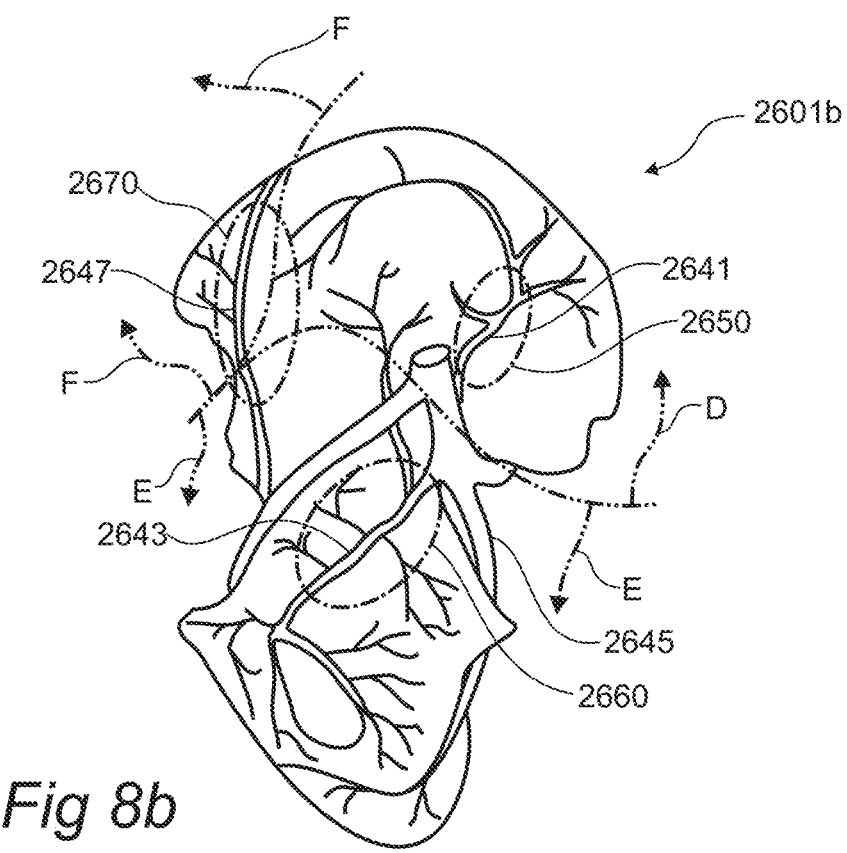

FIGS. 8a and 8b show aspects of access and treatment regions for a target organ in accordance with the present disclosure. The target organ shown is a coxal bone 2601a (i.e., a representative non-limiting example of a complex bone structure). FIG. 8a illustrates an exopelvic view of half of a coxal bone 2601a and the vasculature providing blood to the coxal bone 2601a. Also illustrated are sections A, B, C of the coxal bone 2601a (roughly corresponding to the illium, acetabulum, and ischium), which may be accessed by different vasculature respectively. Section A may be accessed via the superior gluteal artery 2605, the superficial branch of the superior gluteal artery 2607, the deep branch of the superior gluteal artery 2609, the deep superior gluteal artery 2611, deep inferior gluteal artery 2613, and/or the artery of the acetabulum 2615. The nerves associated with sites in section A may be treated by applying a system or method in accordance with the present disclosure to zone 2620 or a site in the vicinity thereof. Section B may be accessed via the pudendal artery 2617 or a branch thereof, or the artery of the ischium 2619. The nerves associated with section B may be treated by applying use of a system or method in accordance with the present disclosure to zone 2630 or a site in the vicinity thereof. Section C may be accessed via the obturator artery 2623 and a treatment therefor applied in the region of zone 2640.

In general, it can be seen from FIG. 8a that the treatment may be provided along any of the indicated arteries, but that an improved therapy in terms of maximizing localization of the treatment, while minimizing collateral involvement of other nerves in the body may be performed near enough or in a deep enough branch, such that the branch under consideration provides only the region of the organ to be treated, while not getting so close to the organ, or within the organ, such that a high proportion of nerves are no longer within the reach of the treatment for a given site along the selected vessel.

FIG. 8b illustrates an endopelvic view of half of a coxal bone 2601b and the vasculature providing blood to the coxal bone 2601b. Also illustrated are sections D, E, F of the coxal bone 2601b (roughly corresponding to the ischium/pubic body/acetabulum, the posterior iliac spine, and the iliac crest), which may be accessed by different vasculature respectively. Section D may be accessed via the illiolumbar artery 2641. The nerves associated with sites in section D may be treated by applying or using a system or method in accordance with the present disclosure to zone 2650 or a site in the vicinity thereof. Section E may be accessed via the obturator artery 2643 or a branch thereof, or the pudendal artery 2645. The nerves associated with section E may be treated by applying or using a system or method in accordance with the present disclosure to zone 2660 or a site in the vicinity thereof. Section F may be accessed via the deep circumflex iliac artery 2647 and a treatment therefor applied to one or more nerves in the region of zone 2670 or a site in the vicinity thereof.

In aspects, one or more neural structures may be monitored and/or treated on one or more walls of the arteries or veins 2605, 2607, 2609, 2611, 2613, 2615, 2617, 2619, 2623, 2641, 2643, 2645, 2647, within the medullary cavity of the coxal bone 2601a, 2601b, within one or more sites of the spongy bone, near to the foramen of one or more of the arteries/veins 2605, 2607, 2609, 2611, 2613, 2615, 2617, 2619, 2623, 2641, 2643, 2645, 2647 into the coxal bone 2601a, 2601b, within the periosteal space of the coxal bone 2601a, 2601b, one of more of the sections A, B, C, D, E, F, and/or one or more of the vessels coupled thereto. In aspects, a procedure may be applied in the vicinity of one or more zones 2620, 2630, 2640, 2650, 2660, 2670 so as to treat a neurological disorder, a tumor, pain signals sent between one or more regions of the coxal bone 2601a, 2601b and the body, treatment of neural receptors, a homeostatic function, etc. associated with the coxal bone 2601a, 260b.

In aspects, a procedure and/or selective treatment may be applied to a neural structure, an afferent nerve, an efferent nerve, one or more sympathetic nerves (SNS), parasympathetic nerves (PNS), motor nerves, receptors, and/or the like in the vicinity of zones 2620, 2630, 2640, 2650, 2660, 2670. In aspects, a treatment may be applied selectively to SNS or PNS in order to balance a regulatory imbalance in the activity there between, or to create an imbalance in activity there between in order to augment one or more functions of the femur, etc. In aspects, the procedure may be used to treat pain associated with bone cancer, to augment the microenvironment around a bone cancer tumor so as to alter the growth rate thereof, to adjust the production rate of osteoblasts, to alter the bone density, or the like.

In aspects, a method in accordance with the present disclosure may include inserting the distal tip of a device in accordance with the present disclosure into a vessel coupled to the tumor. In aspects, the method may include advancing the tip of the device along the vessel such that the tip may interact with a wall of the vessel sufficiently near to the tumor so as to selectively interact with the neural structures coupled specifically to the tumor. Such positioning may be advantageous to so as to minimally influence other neural structures in the body while interacting with those coupled to the tumor. In one non-limiting example related to the treatment and/or pain reduction of a bone cancer tumor located in the diaphysis region of a femur, the method may include advancing the tip of the device along an artery or vein within the body so as to reach the nutrient artery and/or vein near to the femur (i.e., sufficiently near such that the nerves running alongside the artery and/or vein are primarily coupled with the femur as opposed to nearby muscles, skin, peroneal nerves, or the like). In aspects, the tip may be advanced along the nutrient artery so as to enter a branch dedicated to the femur, so as to interact with the vessels near to the periosteum of the femur, near to the foramen where the nutrient artery or vein enters the femur, to pass within the medullary cavity of the femur, or the like. In aspects, a method to treat a tumor and/or pain associated therewith in the epiphysis and/or metaphysis of a femur may include accessing an epiphyseal and/or metaphyseal artery with a tip of a device in accordance with the present disclosure.

According to aspects there is provided a system for treating nerves coupled to a bone of a subject, the system including a micro-tool in accordance with the present disclosure, the micro-tool including a tip sized and dimensioned for placement within a nutrient, epiphyseal, and/or periosteal vessel, artery, or vein coupled to the bone, the micro-tool tip including means for ablating tissues in the vicinity of the vessel in accordance with the present disclosure.

In aspects, the micro-tool tip may include a sensing tip in accordance with the present disclosure, the sensing tip configured to measure one or more of an electrophysiological signal, a neural activity, an afferent neural signal, or the like associated with one or more nerves in the vicinity of the vessel to produce a sensory signal related thereto. In aspects, the micro-tool tip may be configured to provide a controlled ablation to one or more of the nerves, while substantially preserving tissues surrounding the nerves. In aspects, the micro-tool tip may include a substance delivery needle for providing a drug substance to one or more of the nerves to perform the ablation. In aspects, the micro-tool tip may include an energy delivery means, for providing an ablating current, ultrasound energy, high intensity focused ultrasound (HIFU), MR guided HIFU, thermal energy, cryogenic change, etc. to one or more of the nerves. In aspects, the system may include a signal conditioning circuit and a processor for identifying the presence and/or characterizing one or more of the nerves, to generate a feedback signal therefrom, and to coordinate the energy or substance delivery based upon the feedback signal.

In aspects, the micro-tool tip may have a characteristic diameter of less than 1 mm, less than 0.5 mm, less than 0.25 mm, or the like to facilitate placement into the vessel.

In aspects, the micro-tool tip may include one or more electrodes in accordance with the present disclosure. One or more of the electrodes may be sized and dimensioned to measure the signal, and/or one or more of the electrodes may be sized and dimensioned to stimulate and/or ablate one or more of the nerves. In aspects, the micro-tool tip may include a plurality of electrodes, each electrode configured for sensing an electrophysiological signal in accordance with the present disclosure in the vicinity thereof, the electrodes electrically isolated from each other such that the collection of locally collected signals may be used to determine activity over region of tissues in the vicinity of the vessel. In aspects, a plurality of electrodes configured for sensing may be coupled to a source, the source configured to deliver a stimulatory or ablation current collectively through the electrodes into the adjacent tissues for interacting with one or more of the nerves. In aspects, the source may be configured such that a current may be substantially directed radially, circumferentially, and/or axially along the vessel wall to interact with one or more of the nerves. In aspects, the micro-tool tip may include a plurality of electrodes configured for sensing, the electrodes situated along the micro-tool tip so as to monitor local activity axially along the vessel.

In aspects, the micro-tool tip may include a reference electrode configured for sensing electrophysiological activity over a larger area than the other sensing electrodes, one or more of the sensing electrodes compared against the reference electrode to form one or more of the signals. In aspects, the source may be configured to ablate the nerves in concert with the sensing, such that the ablation stops in response to a change in one or more of the sensory signals.

In aspects, there is provided, a method for treating nerves coupled to a bone in a subject, the method including ablating, and/or defunctionalizing one or more nerves coupled to the bone in the vicinity of the periosteal space of the bone, and/or in the vicinity of a nutrient, epiphyseal, and/or periosteal artery or vein coupled to the bone.

In aspects, the method may include delivering a micro-tool in accordance with the present disclosure through the nutrient, epiphyseal, and/or periosteal artery or vein to interface with the nerves, at least a portion of the ablating and/or defunctionalizing performed by the micro-tool. In aspects, the method may include determining the location of a tumor in the skeleton of the subject and planning a surgical approach to reach one or more vessels coupled to the tumor, or coupled to a region of the bone in which the tumor is located. In aspects, the method may include determining the afferent and/or the efferent neural traffic from the electrophysiological signals via an algorithm in accordance with the present disclosure.

In aspects, the method may include monitoring the polarity of one or more signals to determine if the signals predominantly include predominantly afferent or efferent neural traffic. In aspects the method may include counting positive facing action potentials per unit time associated with monitored neural traffic, counting the negative facing action potentials per unit time associated with the monitored neural traffic, and determining a proportion of positive facing action potentials per unit time from the total number of action potentials. The method may include deriving a metric to determine whether the overall traffic is predominantly efferent or afferent in nature, the metric related to the proportion. In aspects, the method may include monitoring the electrophysiological signals during a stress test in accordance with the present disclosure to determine the type and/or function of one or more of the nerves.

In aspects, a system and/or method in accordance with the present disclosure may be used to treat bone cancer, to reduce, stop, or reverse a rate of tumor growth, and/or to reduce or stop cancer related pain. In aspects, a system and/or method in accordance with the present disclosure may be used to treat osteoporosis, and/or to augment bone density of one or more bones in a subject. By bone is meant one or more bones of the skeleton of a subject. Some non-limiting examples of bones include femur, coxal, sacrum, vertebrae, ribs, humerous, ulna, radius, and tibia.

Depending on the location of the tumor within the bone, the approach for treating the nerves may be directed along an artery or vein feeding the epiphysis region of the bone, the joint, cartilage in the joint, the diaphysis of the bone, the periosteal region of the bone, or the like. In aspects, the micro-tool may be inserted along the artery or vein to within the margin of the bone, and ablation may be performed along the vessel walls to treat the nerves at these sites.

In aspects, a micro-tool in accordance with the present disclosure may be inserted along the artery or vein in the periosteal region of the bone and may be used to treat the nerves as they approach the bone along such vessels.

A treatment for increasing bone density within one or more bones in a subject may include ablating the afferent and/or sympathetic nerves innervating a bone in a subject. The method may include ablating one or more nerves in the vicinity of the epiphyseal, nutrient, and/or metaphyseal forma or vessel (artery/vein) near to the bone. The method may include ablating the nerves at one or more sites along the path between the nerves and/or nutrient vessels separating from the parent plexus and the branches serving substantially just the bone in question. Some non-limiting examples of parent plexuses (dependent on the particular bone under treatment) include the peroneal nerve plexus, ulnar nerve plexus, a lumbar plexus, obturator plexus, superior gluteal nerve plexus, inferior gluteal nerve plexus, tibial nerve plexus, accessory obturator plexus, pudental nerve plexus, or the like. The treatment site may be selected such that the branch from the parent plexus is near to or into a region of marrow in the bone.

In a method in accordance with the present disclosure, a stress test may be applied to determine if the distal tip is properly placed for treatment of the nerves substantially innervating only the target bone/organ. In aspects, the stress test may include applying a touch, heat, etc. to a lower extremity, stimulation to a muscle, etc. while monitoring neural traffic along the wall of a target vessel. If a strong response is seen at the sensing site, advance the distal tip further along towards the bone/organ before testing again. If the distal tip does not register a response from the seemingly unrelated stimulus or stress, treat the nerves at that site.

In accordance with the present disclosure, there is described use of a method and/or system in accordance with the present disclosure to alter bone pain (i.e., associated with a recurring injury, osteoporosis, bone cancer, etc.), bone density, bone tumor progression, and/or fertility in a subject. In aspects, ablation of one or more nerves through the wall of a nutrient artery or vein in a subject may be used to treat bone pain, alter bone tumor growth, alter bone density, and/or alter a fertility state of a subject.

Generally speaking, the broad distribution of innervation to bones may explain why pain originating from the joint presents in many ways, with variable and complex referral patterns for individual patients. The coxal bone and the medullary cavity of the coxal bone are innervated with nerves that travel along with the arteries and veins serving various regions of the bone (e.g., the ilium, pubis, and acetabulum). Such innervation travels alongside the femoral artery, the superior and inferior gluteal arteries, the artery of the acetabulum, pudendal artery, artery of the ischium, obturator artery, and branches thereof. The innervation to the various regions of the coxal bone stems from the femoral nerve, obturator nerve, sciatic nerve, etc.

In aspects, a system or method in accordance with the present disclosure may be configured to provide therapy to one or more neural structures in the vicinity of one or more such arteries, generally in the vicinity of the periosteum of the coxal bone. In aspects, the location of a tumor within the coxal bone may be identified (i.e., via a sensing system or method in accordance with the present disclosure, via an imaging modality, etc.). Once the location is identified, a strategy to reach the nerves coupled to that region of the coxal bone may be formulated, as outlined in the FIGS. 8a and 8b. As can be seen from the FIGS. 8a and 8b, target regions for treatment of the nerves coupled to the bone are generally coupled to branches of the parent arteries. In aspects, the treatment may be performed on a branch of an artery or vein that is entirely coupled with the intended bone (i.e., as opposed to treating the parent vessel, which may include a plurality of additional neural structures, not related to the target region of the target bone). Such an approach may be used to provide an effective and highly selective treatment with a minimum of treatment volume, and while minimizing side effects, affecting other nearby neural circuits, etc.

FIGS. 9a-9c show aspects of a device 900 in accordance with the present disclosure. FIG. 9a shows the device 900, shaped and dimensioned for placement into an organ, a vessel, a foramen, etc. each in accordance with the present disclosure. The device 900 includes a sensing tip 910 which is positioned within a region 907 (i.e., in this along a nutrient artery 12 near the foramen of a long bone 10) for purposes of treatment, monitoring, diagnostics, etc. A region 907 defined in the vicinity of the sensing tip 910 may be coupled with the sensing tip 910 during a procedure (e.g., for purposes of monitoring, stimulating, treating, ablating, delivering a substance to, etc. tissues in the vicinity of the region 907). The device 900 has been inserted endovascularly, percutaneously, etc. into a lumen in the body in accordance with the present disclosure and directed to the monitoring site near the long bone 10. In the example shown, the device 900 has been directed along the nutrient artery 12 (alternatively along a nutrient vein 14, epiphyseal artery/vein, metaphyseal artery/vein, or the like, etc.) such that the tip 910 of the device 900 is placed in intimate contact with one or more electroactive anatomical sites there within. In aspects, the device 900 may be placed such that the tip 910 is oriented within the lumen of a vessel (e.g., an artery, a vein, nearby or into the bone, etc.) for obtaining physiologic information therefrom.

As shown in FIG. 9a, the tip 910 is placed such that the sensing/treatment elements associated therewith are positioned so as to treat the targeted nerves without causing extensive damage to the target organ (e.g., in this case a femur bone). In aspects, the tip 910 may be positioned near the foramen of the bone, near to the foramen but outside of the bone perimeter, etc. In aspects, the tip 910 may be positioned just within the bone, the energy/chemical delivering portion of the tip 910 positioned so as to interact with the nerves near the foramen, the periosteal space, a joint, an epiphyseal space, a metaphyseal space vesicular, etc.

In aspects, the device 900 (e.g., a guidewire, a microtool, a catheter, etc.), placed nearby and/or within the bone margin may be arranged so as to monitor electrophysiological activity during an associated stimulus event, surgical procedure/event, follow up procedure, stress test, etc. Such events may include a change in bone stress (e.g., as induced by a change in posture, introduction of bolus of fluid, altering blood pressure systemically, etc.), introduction of a vasodilator (e.g., bradykinin, etc.), inducing a thermal change (e.g., changing a room temperature, introducing a hand into cold or warm water, cooling or warming the blood, etc.), performance of a surgical procedure in accordance with the present disclosure, combinations thereof, or the like. The local electrophysiological response to such stimulus may be an indicator of the function of bone receptors, sensitivity to bone pain, traffic relating to bone pain, extent of cancer damage to the bone, may help to quantify the state of the sympathetic nervous system in the subject, may be used to determine or predict the extent that a subject may respond to a procedure, etc. In aspects, the stimulus may cause a change in afferent signal activity from nerves innervating a spongy bone, a periosteal space, a joint, an epiphyseal space, a metaphyseal space, etc. Such activity may be monitored at a second location near a neural plexus along the femoral artery, near to the spine, or elsewhere in the body. The presence, change in, or absence of such signals at the second location may be indicative of the health of the neurological interconnection there between (e.g., the state of the nerves located between the two sites, the extent of a neuromodulation procedure, etc.).

The device 900 may be connected to a controller 920 (not explicitly shown) for purposes of capturing signals from the tip 910 thereof. The sensing tip 910 may include one or more sensors and/or electrodes, each in accordance with the present disclosure. The device 900 may include one or more electrical interconnects (not explicitly shown) at the proximal end for interfacing with the controller 920.

Such a configuration may be advantageous for monitoring key physiologic information relating to a neuromodulation stimulus, a stress test, a surgical outcome, disease state, a surgical follow up, a neuroendocrine diagnostic, a neurological response to one or more of the above, etc. In aspects, such information may be used for purposes of diagnosing a disease within a subject, for determining the outcome of a stimulus or surgical procedure, for predicting the outlook of a subject after a surgery or a procedure, for predicting a subject's response to or suitability for a neuromodulation therapy, etc.

FIG. 9b shows a schematic of a sensing guidewire 900 in accordance with the present disclosure. The guidewire 900 includes a sensing tip 910 at the distal end thereof. The sensing tip 910 may include one or more sensors and/or electrodes each in accordance with the present disclosure. The guidewire 910 may also include one or more connectors 940 located at the proximal end thereof. The connectors 940 may be dimensioned and configured to interface with an interconnection module 935 or a controller 920. Although shown separately, the interconnection module 935 and the controller 920 may be integrated into a single unit. In aspects, a system in accordance with the present disclosure may include both an interconnection module 935 and a controller 920 coupled together by a cable 945.

The guidewire 900 may include one or more leadwires and/or fibers to connect elements in the sensory tip 910 to the connectors 940 thereof. In aspects, such leadwires may be constructed from one or more materials known in the art. In aspects, the leadwires and/or fibers may be constructed from MRI compatible materials (e.g., resistive wires, carbon fibers, etc.) so as to minimize heating during use in MRI guided surgical procedures.

In aspects, the optional interconnection module 935 may include one or more preamplifiers, multiplexers, switching networks, etc. each in accordance with the present disclosure. Such a configuration may be advantageous to minimize the length of leadwires between the sensing tip 910 and the first signal amplification stage (i.e., a preamplifier in the interconnection module 935).

In aspects, the guidewire 900 may include one or more microcircuits 930 embedded therein. The microcircuits 930 may be coupled with one or more elements within the sensing tip 910 as well as coupled to the connectors 940. The microcircuits 930 may be dimensioned and configured to provide suitable preamplifier functionality, multiplexing operations, digital communication hardware, etc. in order to improve signal integrity from one or more elements within the sensing tip 910, to reduce lead wire count, etc. In aspects, the microcircuits 930 may be coupled to elements of the sensing tip 910 using an ultra-high density interconnect technology as known in the art and in accordance with the present disclosure.

In aspects, the microcircuit 930 may be implemented in an application specific integrated circuit, as one or more bare die chipsets, flip chips, ultrafine pitch ball grid array mounted chipsets, chip scale packages, ultra-fine blind via attachment, flexible HDI interconnects, wire bonded bare die, combinations thereof, or the like. In aspects, the microcircuit 930 may be formed from a thinned silicon die, thinned to a thickness of less than 100 µm, less than 50 µm, less than 10 µm, less than 5 µm. In aspects, the microcircuit 930 may be provided in an ultra-low profile flip-chip, chip scale package, with pitch scaling in the range of 10-50 µm.

In aspects, an array of microcircuits 930 may be arranged upon a substrate in accordance with the present disclosure to facilitate interconnection with the sensing tip 910. The array of microcircuits 930 may be arranged along the substrate and dimensioned so as to maintain the small diameter aspects of the guidewire 900 (i.e., arranged in a single file linear pattern along a predetermined length of the guidewire 900). In aspects, the microcircuit 930 may be encapsulated in a polymer bead, inserted into a protective tube, inserted into the core of a guidewire spring shank, etc.

In aspects, the microcircuit 930 may be coupled with one or more strengthening members so as to minimize the risk of damage to the coupling between the microcircuit 930 and the sensing tip 910 or the connectors 940. In aspects, the strengthening members may be configured to as to allow for compression, tension, and/or torque transfer through the region of the guidewire 900 that includes the microcircuit 930.

In aspects, the controller 920 may include one or more user inputs (e.g., buttons, foot pedals, sliding mechanisms, touch screen displays, etc.) for providing the controller with user guided input so as to adjust signal gain, deploy an aspect of a surgical tool, adjust a stimulation parameter, apply a stimulation, combinations thereof, or the like. In aspects, the controller 920 may include a display for providing a user with information relating to the physiologic signals, outcome of a procedure, an electrophysiological map, combinations thereof, or the like.

FIG. 9c shows aspects of methods for using a device 900 (e.g., a microtool, a catheter, a guidewire, etc.) in accordance with the present disclosure. Although the methods describe accessing the parenchyma of an organ, foramen, organ margin, etc. they could be equally adapted to measuring electrophysiological activity in vessels within a body (e.g., within arteries, veins, etc.), for accessing a miniature lumen within the body, etc. A first method 960 for diagnosing a medical condition is described that includes accessing the parenchyma of an organ. By accessing the small vessels accessing or within the parenchyma of an organ is meant coupling a sensor or electrode in accordance with the present disclosure with one or more anatomical sites within the parenchyma of an organ, so as to measure, stimulate, and/or treat one or more sites therefrom. The first method 960 further includes recording physiologic activity from the parenchyma of the organ (e.g., with a sensor or electrode, a guidewire, a surgical tool, etc. each in accordance with the present disclosure), and monitoring a trend in the physiologic signal (e.g., during a stimulation event, during a stress test, etc.), and/or making a diagnosis or prognosis based upon the recorded signal (e.g., a diagnosis of a disease state associated with local physiologic activity in the parenchyma of the organ, making a prognosis relating to an outcome of a disease state associated with activity in the parenchyma of the organ, etc.).

In aspects, the first method 960 may include one or more additional steps in accordance with the present disclosure. In aspects, the first method 960 may include placing an additional tool including one or more sensors and/or electrodes at a remote location (with respect to the organ) in the body and stimulating the local anatomy at either the remote site or within the parenchyma of the organ and monitoring an evoked response within the parenchyma of the organ or at the remote site respectively. Such a configuration may be advantageous for elucidating information about the connectivity between the two sites (i.e., relevant to determining if a neuromodulation procedure applied there between has been successful, etc.).

A second method 970 is shown including accessing the parenchyma of an organ in accordance with the present disclosure. The second method 970 may further include recording physiologic activity from the parenchyma of the organ, performing a treatment on the body, recording a change in physiologic activity, and determining if the treatment was successfully applied. In aspects, the second method 970 may include one or more additional steps in accordance with the present disclosure.

A third method 980 is shown including accessing the parenchyma of an organ (alternatively an anatomical site of interest, a vessel, an artery, a vein, an arteriole, a venule, a foramen of a bone, into a spongy bone, into a joint, into a epiphyseal space, a metaphyseal space, etc.), and mapping the electrophysiological activity in the vicinity of the anatomical site of interest. The mapping may be provided by sweeping a sensory tip in accordance with the present disclosure over the anatomical site of interest, inserting and then withdrawing the sensory tip, deploying the sensory tip and then dragging and/or rotating the deployed tip along/ around the lumen wall, combinations thereof, and the like. In aspects, the third method 980 may include displaying the mapped physiologic information for a user, constructing an anatomical model therefrom, directing a surgical robot to perform a treatment therefrom, comparing the map with a previously determined map (e.g., as a means for monitoring the outcome of a procedure, tracking a therapy, etc.), combinations thereof, or the like. In aspects, the method may include providing one or more directions to a surgeon and/or a surgical robot to access one or more regions of the mapped anatomy, overlaying the present map with previously generated maps (so as to evaluate changes in functionality, activity, etc.), combinations thereof, and the like.

A fourth method 990 is described including accessing an anatomical site of interest within the parenchyma of an organ, stimulating one or more physiologic systems in the body, and monitoring the evoked response at the anatomical site of interest. The fourth method 990 may include assessing the functionality of the anatomical site of interest, the site of stimulation (i.e., if the stimulation is of a localized type), or an anatomical site there between. In aspects, the method may include ablating one or more anatomical sites within the body. A device 2110, 900 in accordance with the present disclosure may include one or more electrodes, chemical delivery elements, etc. configured to performing a treatment on the surrounding tissues, etc. In aspects, one or more methods in accordance with the present disclosure may be completed, at least in part, with a device 900 in accordance with the present disclosure.

FIG. 9d shows a schematic of a sensing guidewire 902 in accordance with the present disclosure. The guidewire 902 may include one or more zones such as a sensing tip 912, a sensing/ablation/stimulation zone 914, and/or a second sensing zone 932 each located towards the distal end thereof. One or more of the zones may include aspects for sensing, ablating, stimulating, biasing against adjacent tissues, etc. In aspects, the sensing tip 912 may include one or more sensors and/or electrodes each in accordance with the present disclosure. In aspects, a second zone 914 may be configured to bias 937 one or more aspects of the guidewire 902 against an adjacent lumen wall for purposes of coupling thereto (such as to perform a procedure in accordance with the present disclosure, etc.). In aspects, a third zone 932 is shown, configured so as to interface with an adjacent lumen wall for purposes of sensing, ablation, stimulation, combinations thereof, or the like.

In aspects, the guidewire 902 may also include one or more connectors 942 in accordance with the present disclosure located at the proximal end thereof. The connectors 942 may be dimensioned and configured to interface with an interconnection module 938 or a controller 922. Although shown separately, the interconnection module 938 and the controller 922 may be integrated into a single unit. In aspects, a system in accordance with the present disclosure may include both an interconnection module 938 and a controller 922 coupled together by a cable 947.

In aspects, the optional interconnection module 938 may include one or more preamplifiers, multiplexers, switching networks, etc. each in accordance with the present disclosure. Such a configuration may be advantageous to minimize the length of leadwires between the sensing tip 912 and the first signal amplification stage (e.g., a preamplifier in the device 900, the vicinity of the sensing tip 912, the interconnection module 938).

In aspects, the guidewire 902 may include one or more microcircuits embedded therein (herein embedded within one or more of the zones 912, 914, 932). The microcircuits may be coupled with one or more elements within the sensing tip zone 912 as well as coupled to the connectors 942. The microcircuits may be dimensioned and configured to provide suitable preamplifier functionality, multiplexing operations, digital communication hardware, etc. in order to improve signal integrity from one or more elements within the sensing tip zone 912, to reduce lead wire count, etc. In aspects, the microcircuits may be coupled to elements of the sensing tip zone 912 using an ultra-high density interconnect technology as known in the art and/or in accordance with the present disclosure. In aspects, one or more of the zones 912, 914, 932 may be configured so as to interface with an adjacent anatomical feature along which a treatment is desired. Information and/or treatment provided by each zone may be used to determine effective delivery of treatment to a region along the anatomical feature (i.e., physiologic sensing and/or stimulation provided at sites within zones 912 and 932 may be used to determine the effectiveness of a neuromodulation therapy provided to the adjacent tissues in the vicinity of zone 914). In aspects, a therapeutic, stimulatory, and/or sensing configuration may be coupled between zones 912, 914, 932. In aspects, one or more steps of a method in accordance with the present disclosure may be performed with one or more zones 912, 914, 932 of a guidewire 902 in accordance with the present disclosure.

The connectors 942 may be dimensioned and configured to interface with an interconnection module 938 or a controller 922. Although shown separately, the interconnection module 938 and the controller 922 may be integrated into a single unit. In aspects, a system in accordance with the present disclosure may include both an interconnection module 938 and a controller 922 coupled together by a cable 947. In aspects, the optional interconnection module 938 may include one or more preamplifiers, multiplexers, switching networks, etc. each in accordance with the present disclosure. Such a configuration may be advantageous to minimize the length of leadwires between the sensing tip 912 and the first signal amplification stage (i.e., a preamplifier in the interconnection module 938).

FIGS. 10a-10n show aspects of sensing tips 910, and/or zones 912, 914, 932 associated with a device 900, 902 (a device, a catheter, a guidewire, etc.) each in accordance with the present disclosure. FIG. 10a shows aspects of a device 1001 including one or more sensors or electrodes 1002 located at the distal tip thereof. In aspects, the electrodes 1002 may be arranged in patterns around the circumference of the tip so as to contact a lumen wall if the guidewire 1001 is introduced deep enough into the lumen so as to bottom out (i.e., as the lumen diameter shrinks distally heading into the organ). The electrodes 1002 may be connected to a controller 1005, a preamp, a microcircuit, a connector, or the like in accordance with the present disclosure. Such interconnection may be provided by one or more leadwires 1004 arranged along the length of the device 1001. In aspects, one or more of the leadwires 1004 may be integrated into the walls or jacket of the device 1001. In such configurations, the leadwires 1004 may be helically integrated, and/or braided into the walls or jacket, or equivalently threaded, coextruded, plated, shrink wrapped, or pultruded within the walls of the device 1001 (i.e., or equivalently threaded through one or more microlumen within the wall of the device 1001). In aspects, the device 1001 may have a distal tip diameter 1003 of less than 3 mm, less than 2 mm, less than 1 mm, less than 0.5 mm, less than 0.25 mm, or the like to facilitate placement into the vessel.

The electrodes 1002 may be formed in accordance with the present disclosure. In aspects, the electrodes 1002 may be formed directly from the tips of the one or more leadwires 1004. The tips of the leadwires 1004 may be formed into microelectrode elements, with predetermined exposed areas and tip profiles, suitable for monitoring electrophysiological activity at the site of interest. In aspects, the predetermined exposed areas may be designed so as to lean towards single unit recordings (e.g., electrode area less than 250 square micrometer ($\mu m^2$), less than 150 $\mu m^2$, less than 100 $\mu m^2$), multi-unit recordings (e.g., electrode area of greater than 500 $\mu m^2$, greater than 1000 $\mu m^2$, greater than 2000$\mu m^2$), and large area or reference field recordings (e.g., electrode area greater than 10,000 $\mu m^2$, greater than 1,000,000 $\mu m^2$, or the like). In aspects, the electrodes 1002 may be treated so as to alter the impedance thereof, during use. In aspects, the electrodes may be processed so as to increase the capacity thereof such as via conversion to, plating of, or augmentation with an electric energy storage (EES) material, an intercalating material, surface area increasing process, a plating process, combinations thereof, or the like. In aspects, each electrode 1002 may be configured with a profile suited for accessing the anatomy of interest (e.g., a needle-like structure, an embossed structure, a whisker like structure, a dendritic structure, etc.).

FIG. 10*b* illustrates aspects of a sensing tip of a guidewire 1006 with a deployable tip array 1008 arranged near to or at the distal tip thereof. Optionally, the guidewire 1006 may include a jacket 1007 arranged along the length thereof. The jacket 1007 may be configured so as to slide along a core structure, the core structure supporting the deployable tip array 1008. Thus, retraction of the jacket (or equivalently protrusion of the core structure) may be used to deploy the elements of the deployable tip array 1008 once the tip of the guidewire 1006 has been delivered to an anatomical site of interest. The deployable tip array 1008 may include one or more microfingers 1010 in accordance with the present disclosure. Each microfinger 1010 may include one or more sensors or electrodes in accordance with the present disclosure. In FIG. 10*b*, a guidewire 1006 is shown with an array of microfingers 1010, each equipped with a microelectrode 1009 upon the distal tip thereof. The microelectrodes 1009 and microfingers 1010 may be configured so as to bias towards a lumen wall upon deployment, or configured so as to penetrate the lumen wall upon deployment or during a penetrating maneuver (e.g., pushing the deployed tip array 1008 forward along the lumen wall, etc.). In aspects, the microfingers 1010 may be actuated so as to facilitate deployment (e.g., via an electroactive, electrochemical, mechanical, and/or thermomechanical activation means). In aspects, the microfingers 1010 may be one-time deployable via a biodegradable mechanism (e.g., dissolution of an adhesive binding element, a thermally activated material, etc.).

In aspects, one or more of the microfingers 1010 may be shaped such that it forms the desired shape upon deployment (subject to the dimensions of the local anatomy). In aspects, the microfingers 1010 may be configured to form an umbrella like structure, a basket like structure, a helical structure, a star like structure, a porcupine like structure, etc.

One or more elements of the sensing tip may be interconnected with a controller 1011, preamp, microcircuit, circuit, a connector, or the like in accordance with the present disclosure.

FIG. 10*c* shows aspects of a sensing tip of a guidewire 1015 in accordance with the present disclosure. The sensing tip includes a j-curved segment 1016 which may be configured with a subminiature bend radius. In aspects, the j-curved segment 1016 may be formed with a radius of less than 4 mm, less than 3 mm, less than 1 mm. The sensing tip may include one or more electrodes 1017, 1018. As shown in FIG. 10*c*, the sensing tip may include one or more microelectrodes 1017 and one or more reference electrodes 1018 (optional). The microelectrode 1017 may be exposed to the surroundings over a subset of the overall tip area (e.g., over an area most likely to bias against a lumen wall during insertion, over a region facing away from the axis of the j-curve segment 1016, etc.). In aspects, the reference electrode 1018 may be formed by exposing and/or processing a segment of the guidewire 1015 (e.g., removing an insulating coating therefrom, plating a material thereto, swaging a tube onto the guidewire segment, etc.). The electrodes 1017, 1018 may be coupled to a connector and/or a controller 1020, preamp, microcircuit, circuit, a connector, or the like in accordance with the present disclosure.

The j-curved segment 1016 may be advantageous to maintain contact with the walls of a lumen during a placement procedure. In aspects, the j-curved segment 1016 may be dimensioned with a predetermined radius and configured with a predetermined stiffness such that the electrodes 1017, 1018 may consistently contact the walls of vessels with a characteristic diameter within a predetermined range (e.g., 2-8 mm, 1-4 mm, 0.5-2 mm, etc.). The j-curved segment 1016 may also be configured so as to bias 1019 the electrodes against the wall of a lumen during a study. In aspects, the j-curved segment 1016 may include one or more strain measuring elements (e.g., a strain gauge, a piezoresistive material, etc.) configured to measure the diameter of the lumen into which the guidewire 1015 has been placed.

FIG. 10*d* illustrates aspects of a sensing tip of a sensing guidewire 1021 in accordance with the present disclosure. The guidewire 1021 includes a pushable core 1022 or equivalently a retractable sheath 1023 configured so that the core can be deployed once the guidewire 1021 has been directed to an anatomical site of interest. In aspects, one or more of the tip configurations disclosed herein may be attached to the pushable core 1022 in order to construct a sensing guidewire 1021 with a deployable 1022*a* tip structure (e.g., with a deployable tip array, a basket arrangement, etc.).

In aspects, the core 1022 may be coupled with a controller 1025, preamp, microcircuit, circuit, a connector, or the like each in accordance with the present disclosure.

FIG. 10*e* shows aspects of a sensing tip of a guidewire 1026 in accordance with the present disclosure. The guidewire 1026 includes a microbasket electrode array 1027 including an array of microfingers 1029, each arranged in a bowed shape so as to extend out from the axis of the lumen into which the device is placed. Aspects of a single microfinger 1029 in the array is shown in the detailed view A. The microfinger 1029 includes one or more sensors or electrodes 1028, each in accordance with the present disclosure. In the example shown in FIG. 10*e*, the electrode 1028 is shown patterned so as to face radially outwards from the center of the lumen into which the sensing tip is deployed. The electrode 1028 may be formed in accordance with the present disclosure. One or more regions of the microfinger 1029 may be isolated from the surroundings with an insulating layer (e.g., a passivated layer, a dielectric layer, a polymer, PTFE, parylene, etc.). In aspects, the microfinger 1029 may be configured so as to deploy to reach the shape shown in FIG. 10*e* during a predetermined procedure (e.g., actuation, sheath retraction, core extension, biodegradation of a restraint, etc.). In aspects, the microbasket array 1027 may be deployed during use so as to interface with the walls of a lumen, in accordance with the present disclosure. One or more microfingers 1029 and/or sensors or electrodes 1028 may be coupled with a connector or a controller 1030, preamp, microcircuit, circuit, a connector, or the like each in accordance with the present disclosure.

FIG. 10f illustrates aspects of a sensing tip of a sensing guidewire 1031 in accordance with the present disclosure. The guidewire generally includes one or more lumens and a microporous tip 1032 which includes one or more ports 1038 through which one or more protruding microneedle elements 1034 may pass upon deployment. The guidewire 1031 is shown in a retracted state 1036 which may be suitable for accessing a target anatomical site in accordance with the present disclosure, as well as in a deployed state 1037 which is suitable for interfacing one or more sensors or electrodes with the target anatomical site as part of a procedure. One or more of the protruding microneedle elements 1034 may include a sensor or an electrode on the exposed tip 1033 thereof. One or more of the microneedle elements 1034 may include one or more features 1035 such as bumps, step changes in insulation, etc. configured so as to limit the penetration depth of such exposed tips 1033 into the adjacent tissues. One or more aspects of the guidewire 1031 or aspects of the exposed tips 1033 may be coupled to a controller 1039, preamp, microcircuit, circuit, a connector, or the like each in accordance with the present disclosure.

FIG. 10g shows aspects of a sensing tip of a sensing guidewire 1041 in accordance with the present disclosure. The sensing guidewire 1041 includes a plurality of deployable tines 1042, each tine 1042 including one or more sensors and/or electrodes each in accordance with the present disclosure. The deployable tines 1042 may be held together during storage and delivery to a surgical site of interest by a restraint mechanism 1043 (such as a biodegradable adhesive, a water soluble matrix, a thermally stabilized shape set, etc.). Upon delivery to the anatomical site, upon contact with a fluid, etc. the restraint mechanism 1043 may release the tines 1042 to as to deploy 1044 them to form a deployed state. In the deployed state, the tines 1042 may be significantly biased 1047 towards the walls of a lumen into which the sensing tip has been placed, etc. One or more aspects of the guidewire 1041 or aspects of the tines 1042 may be coupled to a controller 1046, preamp, microcircuit, circuit, a connector, or the like each in accordance with the present disclosure.

FIG. 10h shows aspects of a sensing tip of a sensing guidewire 1051 in accordance with the present disclosure. The sensing tip includes one or more microfingers 1052 in accordance with the present disclosure. The microfingers 1052 shown in FIG. 10h are equipped with a plurality of sensing points 1053, each including a sensor or electrode in accordance with the present disclosure. The sensing guidewire 1051 is shown placed within a lumen 25 within a body and the microfingers 1052 have been deployed such that the sensing points 1053 may interface with the walls of the lumen 25. One or more of the sensing points 1053 may be coupled with a controller 1054, preamp, microcircuit, circuit, a connector, or the like each in accordance with the present disclosure in order to record signals therefrom during a monitoring session. In aspects, the sensing guidewire 1051 may be retracted while in the position shown so as to drag 1055 the sensing points 1053 along the walls of the lumen 25, so as to map the physiologic signals there upon. In aspects, such a configuration may be advantageous for mapping electrophysiological information along the lumen wall, for generating an anatomical map, for evaluating the location of active neuromuscular sites, evaluating the type and/or direction of neurological traffic in the vicinity of each sensing point 1053, etc.

FIG. 10i illustrates aspects of a sensing tip of a sensing guidewire 1060 in accordance with the present disclosure. The sensing tip includes a jacket 1062 and a shaped tip 1064, the jacket 1062 dimensioned with a diameter 1070 sufficiently small so as to access an anatomical site of interest within a body. The sensing tip further includes one or more sensors 1066 each nested into an access port. The guidewire 1060 also includes one or more lead wires 1068 interconnected with the sensors 1066 and the proximal end of the guidewire 1060 (e.g., a connector, a microcircuit, a controller 1072, a preamp, microcircuit, circuit, a connector, etc.).

In aspects, one or more of the sensors may be configured to monitor a local analyte concentration (e.g., a hormone concentration, norepinephrine, catecholamine, renin, angiotensin II, an ion concentration, a water level, an oxygen level, etc.), a pH level, etc.

FIG. 10j illustrates aspects of a delivery catheter 1069 in accordance with the present disclosure. The delivery catheter 1069 may provide a sheath through which one or more additional elements may be guided 1072 to an anatomical site within the body and/or to interconnect a distal portion thereof with a controller 1070, preamp, microcircuit, circuit, a connector, or the like. The delivery catheter 1069 may include one or more electrodes 1071 configured for purposes of sensing, stimulation, stress test analysis, neuromodulation, surgical procedural outcome, changes in traffic associated therewith, as reference electrodes, or the like. In aspects, the delivery catheter 1069 may include a bulbous feature 1073 sized and dimensioned so as to provide a stop gap for entrance into a target lumen, for providing hemostasis within a target lumen, etc.

FIG. 10k illustrates aspects of a delivery catheter 1075 with a hollow lumen configured along the length thereof, including one or more sensors 1077, a bulbous feature 1078 each in accordance with the present disclosure. The delivery catheter 1075 is shown with an associated guidewire 1079, deployed from the tip thereof. The guidewire 1079 includes one or more zones 1080, 1082 each in accordance with the present disclosure. The guidewire 1079 includes a sensing tip 1080 attached to a soft guiding tip 1081 configured so as to measure one or more physiologic aspects of an adjacent tissue when positioned within a lumen of a body. The guidewire 1079 includes a biasing zone 1082 including one or more electrodes and/or sensors, each in accordance with the present disclosure. In aspects, the biasing zone 1082 may be configured to deploy upon protrusion of the guidewire 1079 tip beyond the delivery catheter 1075, upon retraction of the delivery catheter 1075, upon actuation of an element within the biasing zone 1082, upon adjustment of a repositionable core within the guidewire 1079, or the like. The guidewire 1079 may be configured so as to advance 1083 or retreat 1084 along the length of a lumen into which it is placed during a procedure.

In aspects, the guidewire 1079 may include a repositionable core in order to construct a sensing guidewire 1079 with a deployable tip structure (e.g., with a deployable tip array, a basket arrangement, helical biasing zone 1082, etc.).

In aspects, one or more sensors and/or electrodes (i.e., included within 1082, 1080) on the guidewire 1079 may be configured to communicate with one or more sensors and/or electrodes 1077 on the delivery catheter 1075.

FIG. 10l illustrates aspects of a guidewire 1101 in accordance with the present disclosure coupled with a lumen wall 25 into which it has been deployed (i.e., as part of a procedure). The guidewire 1101 may be coupled with a controller 1103 in accordance with the present disclosure. The guidewire 1101 may include one or more sensing tips 1105 for interfacing with the lumen wall 25. The guidewire 1101 may include a soft tip 1107 for assisting with delivery of the guidewire 1101 into the lumen. In aspects, the guidewire 1101 may include one or more electrodes 1109 positioned near to the distal tip of the guidewire 1101 within a biasing zone 1111 in accordance with the present disclosure. The biasing zone 1111 includes a helically shaped region (i.e., such as formed in a shape setting procedure, etc.), so as to bias the electrodes 1109 against the lumen wall 25 upon deployment.

In aspects, the guidewire 1101 may be configured with a characteristic diameter d, of less than 1.5 mm, less than 1 mm, less than 0.75 mm, less than 0.5 mm, less than 0.25 mm, or the like. The shape set aspects of the biased zone 1111 may be configured so as to transition from a disconnected region along the lumen wall 25 into a zone of contact, so as to provide consistent contact with the lumen wall 25 during a procedure. In aspects, the guidewire 1101 may be configured so as to transition from a substantially elongate shape to a deployed shape (e.g., a helical electrode arrangement, etc.), upon deployment into the lumen of a vessel within a body.

In aspects, the guidewire 1101 may be configured for placement within a vessel, for delivery to or within the parenchyma of an organ into which the vessel extends, or the like as part of a surgical procedure. In aspects, the guidewire 1101 may be configured for nerve monitoring, electrophysiological monitoring, stimulation, and/or ablation procedures in accordance with the present disclosure. In aspects, the guidewire 1101 may be configured to provide a path, over which a second surgical tool may be delivered to the vessel, the guidewire sensing tip 1105 configured to monitor one or more physiologic functions relevant to the operation and/or evaluation of a procedure performed by the surgical tool. In aspects, one or more of the zones 1105, 1111, etc. may be configured for sensing local electrophysiological activity, stimulating local neural anatomy, delivering a substance to local tissues, and/or neuromodulating local neural anatomy (e.g., ablating, denervating, etc.) in accordance with the present disclosure. In aspects, a guidewire in accordance with the present disclosure may include a sensing zone 1105 located at the distal tip thereof, an ablating/stimulating zone 1111 located along the length of the guidewire proximally to the distal tip, and a second sensing zone 932, as shown in FIG. 9d, located along the length of the guidewire proximally to the ablating/stimulating zone (not explicitly shown). In aspects, functions performed within each zone 912, 914, 932 of FIG. 9d, 1105, 1111 of FIG. 10l, etc. during a procedure may be coordinated by a controller in accordance with the present disclosure for purposes of diagnosis, determining the extent of a procedure, performing a neuromodulation procedure, denervating a neural structure, combinations thereof, or the like.

In aspects, the guidewire 1101 may be configured with a shape set region 1111, configured to bias 1113 one or more regions 1111 of the guidewire against a wall of a lumen 25 into which it has been placed. In aspects, the guidewire 1101 may include a wire basket, a helical region, a balloon, etc. in order to provide such bias 1113 against an adjacent lumen wall 25. In aspects, the shape set region 1111 may be retractably collapsible into a delivery sheath (i.e., a sheath provided over the guidewire sized and dimensioned for delivery thereof to an anatomical site of interest). In aspects, the shape set region 1111 may be deployed so as to bias against a wall of a lumen 25 into which it is placed by an actuation procedure, retraction of a delivery sheath, protrusion of the guidewire distal tip beyond the distal tip of a delivery sheath, etc.

In aspects, the biasing region 1111 may be deployed via actuation of an actuator element embedded therein. In aspects, such an actuator element may include an active material transducer in accordance with the present disclosure. In aspects, the actuation may be provided by a shape set shape memory alloy, such as may be introduced into the lumen at a temperature substantially below a threshold transition temperature, and undergo a deployment so as to bias against the lumen wall 25 upon increasing temperature to substantially above the threshold transition temperature (e.g., such as via natural heating from adjacent tissue structures, via active heating, via current flow associated with a stimulation and/or ablation procedure, etc.). In aspects, such deployment may be achieved by other forms of actuation such as but not limited to electroactive material expansion, retraction of a central core, pulling of a tendon core, retraction of a sheath, dissolution of a constraining element, etc.

In aspects, a guidewire in accordance with the present disclosure may include a bulbous feature located within the vicinity of the distal tip thereof. The bulbous feature may be configured to bottom out the guidewire within a lumen (e.g., when the lumen diameter approaches that of the bulbous feature, between a step between a feeding lumen and a treatment lumen, etc.) as it is advanced there along during a placement procedure. Such a feature may be advantageous to position the distal tip of the guidewire within a treatment lumen (e.g., a vessel, an artery, a vein, a tubule, etc.), to provide hemostasis to the treatment lumen, etc.

FIG. 10m illustrates aspects of a guidewire 1115 in accordance with the present disclosure. The guidewire 1115 may be coupled with a controller 1125 in accordance with the present disclosure. The guidewire 1115 may include one or more sensing tips 1117 for interfacing with a local anatomical site during a procedure. The guidewire 1115 may include a soft tip 1117 for assisting with delivery of the guidewire 1115 into a lumen within a body. In aspects, the guidewire 1115 may include one or more electrodes 1119 positioned near to the distal tip of the guidewire 1115 within a biasing zone 1118 in accordance with the present disclosure. The biasing zone 1118 shown in FIG. 10m includes a helically shaped region (e.g., such as formed in a shape setting procedure, etc.), so as to bias the electrodes 1119 against an adjacent wall during a procedure. In the biasing zone 1118 may take a deployed form 1120 during placement, or as part of a placement procedure. In aspects, the deployed form 1120 may take on a bulbous shape, an expanded region with tapered ends, a cylindrical profile, or the like.

In aspects, the biasing zone 1118 may include a shape set aspect, configured so as to transition from a first shape that is not sufficiently biased so as to contact an adjacent lumen wall, to a region over which the biasing is sufficient to provide consistent contact with an adjacent lumen wall during a procedure. In aspects, the biasing zone 1118 of the guidewire 1115 may be configured so as to transition from a substantially elongated shape to a deployed shape (e.g., a helical electrode arrangement, etc.), upon deployment into the lumen of a vessel within a body.

In aspects, the guidewire 1115 may be configured with one or more diameters along the length thereof. In aspects, a distal characteristic diameter $d_1$, for the guidewire 1115 may be arranged such that $d_1$ is less than 1.5 mm, less than 1 mm, less than 0.75 mm, less than 0.5 mm, less than 0.25 mm, or the like. In aspects, a proximal characteristic diameter $d_2$ may be arranged such that $d_2$ is less than 1.0 mm, less than 0.75 mm, less than 0.5 mm, less than 0.025 mm, or the like. In aspects, the proximal diameter $d_2$ may be sized so as to provide a sufficiently miniature profile over which an additional catheter and/or surgical tool may be deployed within the body. In aspects, the distal characteristic diameter $d_1$ may be configured so as to accommodate an embedded microcircuit 1123 and/or interconnections thereto.

In aspects, a guidewire 1115 in accordance with the present disclosure may include a microelectronic circuit 1123 embedded within or coupled to the distal tip 1117 thereof, as well as coupled to an interconnect and/or controller 1125 coupled to the proximal end thereof, configured to control signal flow to/from one or more zones 1118, 1117, etc. of the guidewire 1115 for purposes of performing a procedure in accordance with the present disclosure.

In aspects, a guidewire in accordance with the present disclosure may include one or more electrodes, each electrode configured to sense, stimulate, and/or ablate a local anatomical site within a body. In aspects, the guidewire may include a plurality of ablation electrodes configured to interface with a wall of a lumen into which the guidewire is placed, so as to provide coupling for delivery of radiofrequency, and/or microwave frequency energy into the wall of the lumen and/or tissues surrounding the lumen, as part of a procedure in accordance with the present disclosure. In aspects, the guidewire may be configured to monitor one or more physiologic aspects in conjunction with the energy delivery process (e.g., before, during, after, etc.).

In aspects, a system in accordance with the present disclosure may include a delivery catheter including one or more electrodes, and a guidewire including one or more electrodes, the system configured to pass energy between the catheter electrode(s) and the guidewire electrode(s) as part of a procedure. In aspects, the system may be configured to monitor electrophysiological activity between the guidewire electrode(s) and the catheter electrode(s) as part of a procedure.

In aspects, a guidewire in accordance with the present disclosure may include a drug eluting region (e.g., over an electrode, at the distal tip, etc.), configured so as to elute a drug into the vicinity of the region during a procedure (e.g., so as to minimize clotting, minimize damage to adjacent structures, etc.).

In aspects, a guidewire in accordance with the present disclosure may include a thrombus net coupled to the distal tip thereof. The thrombus net may be configured so as to bridge a cross section of a lumen into which the guidewire is placed during a procedure. The thrombus net may be configured to capture debris generated at a site along the system, guidewire, associated catheter, etc. during a procedure in accordance with the present disclosure. The thrombus net may be configured so as to withdraw any captured debris along with the guidewire during withdrawal from the body.

FIG. 10n illustrates aspects of a guidewire 1150 in accordance with the present disclosure placed within a lumen 25. The guidewire 1150 may include one or more zones 1154, 1152 in accordance with the present disclosure. The guidewire 1150 includes a sensing zone 1154 located along the length thereof for interfacing with the lumen wall proximally to a treatment site. The guidewire 1150 includes a sensing tip 1152 located at the distal tip thereof for interfacing with the lumen distally to a treatment site. The guidewire 1150 includes one or more microneedles 1156, which may be advanced from the body of the guidewire 1150 into the wall of the lumen 25 into which it has been placed as part of a procedure. Such needle advancement or retraction 1158 may be coordinated by an operator, a controller 1162, etc. In aspects, the microneedles 1156 may provide a means for delivering a chemical agent 1160 into the tissues surrounding the lumen 25. In aspects, the microneedles 1156 may include one or more electrodes to monitor and/or interface (e.g., stimulate, ablate, etc.) the local tissues upon deployment therein. In aspects, the guidewire 1150 may be configured so as to deliver the microneedles 1156 into the adventitia of the lumen 25, or optionally directly into the parenchyma of an organ to be treated. Such a configuration may be advantageous to provide a mild inflammatory agent, a neurolytic agent, a neurotoxin, a cancer treating agent, a neuroblocking agent, a neurostimulating agent, etc. into the target tissues as part of a treatment procedure in accordance with the present disclosure.

The methods, devices, and systems disclosed in the present disclosure will be better understood by reference to the following examples which are offered by way of illustration and which one of skill in the art will recognize are not meant to be limiting.

EXAMPLES

Example 1

The following non-limiting example is directed at the treatment of neurogenic pathways for tumor growth and metastasis of pancreatic ductal adenocarcinoma (PDAC). A control experiment was performed with 10 athymic nude mice. The 10 mice were surgically prepared under anesthesia, and the surgical site was cleaned with 75% ethanol solution. A dorsal incision was used to access the spleen, pancreas and associated arterial supply. Mia PaCa2 human pancreatic cancer cells were seeded into the pancreas of each mouse. In 5 of the mice, the celiac ganglion and surrounding nerves were ablated with ethanol. The surgical procedures were completed and the mice were returned to Plexiglass boxes for observation.

The animals were monitored for detectable sickness related behavior and tumor growth was monitored via in vivo bioluminescent imaging techniques (IVIS® imaging system). Animals were monitored for relative changes in the following criteria: detectable sickness-related behavior, hunching and postural changes, signs of tumor growth in the animals' back (visible lumps), increases in piloerection, changes in skin tone and character, and changes in voluntary movement levels and exploratory behavior. At 2 weeks post-surgery, the experimental mice demonstrated improved skin tone and movement versus the control mice. At 3 weeks, IVIS® imaging of the mice showed that the average tumor size in the experimental group was 55% the average tumor size in the control group (based upon in vivo luciferase subject ROI imaging of the mice). As the tumor growth continues the experimental group may continue to exhibit slowed growth of the pancreatic ductal adenocarcinoma, reduced pain levels, and reduced perineural invasion of the PDAC cells into surrounding parasympathetic nerves, and the like.

Example 2

The following, non-limiting example, is directed to the identification, evaluation, and subsequent treatment of nerves in a subject. Relating to the alteration of pancreatic neuroendocrine or sensory function, a catheter in accordance with the present disclosure may be advanced along an arterial pathway to the superior and inferior pancreaticoduodenal arteries and branches thereof, the dorsal pancreatic artery, and the splenic artery. The catheter tip, equipped with one or more sensing elements, each in accordance with the present disclosure, is advanced into each of the arteries in sequence. Once placed within a corresponding artery, baseline readings of neural traffic are taken around the wall of the artery. Nerve traffic may be characterized as "normal", "abnormal", "hyperactive", "underactive", etc. according to population acquired data, previously acquired data, etc. The nerve types nearest to each of the sensors may be identified directly from the baseline traffic as being somatosensory, sympathetic, parasympathetic in nature, or the like. Such identification may be made based upon the character of the signals, the temporal changes in the signals with breathing, heart rate, or reflex response to a stimulus, the direction of neural traffic (afferent or efferent) along the artery wall, the action potential characteristics of the signals, etc. If identification or traffic characterization cannot be completed based upon the baseline recordings, a stress test may be performed on the pancreas, an associated organ, coupled neuroendocrine circuit, or the subject on the whole in accordance with the present disclosure.

In one non-limiting example of a neuro-specific stress test, a bolus of a somatosensory neuro agonist (e.g., low dose capsaicin) is injected into the artery and the neural traffic is monitored during the associated stress response. The monitored changes in neural traffic associated with the capsaicin stress test may be associated with somatosensory receptor activity in the region of the pancreas served by the associated artery.

Relating to the modulation of insulin production related neuroendocrine circuit, the neural traffic may be monitored in the associated artery during an associated stress test. In such a stress test, a bolus of glucose may be administered to the subject, and neural traffic may be monitored during the responding insulin regulating reflex reaction. Such changes in neural traffic may be used to identify neural pathways associated with the insulin regulating neuroendocrine circuit in the subject, as well as identify the location of those nerves with respect to the positioning of one or more of the sensors on the catheter situated in the associated artery.

Relating to the alteration of pancreatic juice secretion in the pancreas, the neural traffic may be monitored in the associated artery during a sympathetic nervous system or parasympathetic altering stress test (e.g., via administration of a sympathetic/parasympathetic agonist/antagonist, vagal stimulation, breath hold, tilt test, etc.). Such neural traffic may be used to identify the vagal nerves and the location of the vagal nerves with respect to the positioning of one or more of the sensors on the catheter situated in the associated artery. Vagal nerve traffic to the pancreas influences the production, secretion, and composition of the pancreatic juices. In the lead-up to a pancreas resection surgery (e.g., so as to remove a pancreatic tumor), the vagal nerve pathway may be modulated or remodeled as described herein to reduce the amount or alter the composition of the pancreatic juices.

Upon identification of the nerve types and traffic characteristics, a decision may be made as to whether or not to treat, pace, modulate, ablate, etc. the nerves (e.g., selectively, collectively, etc.). If the decision is made to treat the nerves, one or more nerve treating elements in the catheter (e.g., energy or chemical delivery elements, RF ablation elements, neuroselective ablative agent delivery, general neural ablative agent delivery, placement of a neuromodulating interface, etc.) may be activated so as to complete the treatment procedure. Upon completion, the catheter may be moved to one or more of the other arteries, removed from the body of the subject, etc.

Example 3

The following, non-limiting example, is directed to treatment of pancreatic cancer in a human subject. A catheter in accordance with the present disclosure may be advanced along an arterial pathway to the superior and inferior pancreaticoduodenal arteries and branches thereof, the dorsal pancreatic artery, and the splenic artery. The catheter tip, equipped with one or more sensing elements, each in accordance with the present disclosure, is advanced into each of the arteries in sequence. Once placed within a corresponding artery, baseline readings of neural traffic are taken around the wall of the artery. Once the presence, nerve types, function, and/or local neural activity levels are confirmed, an ablation procedure may be completed with the catheter to perform one or more of the following functions: 1. disconnect and/or block the central nervous system (CNS) from the sympathetic receptors in the pancreas; 2. disconnect pain sensory receptors in the pancreas and/or surrounding organs from the CNS; and 3. disconnect and/or block the CNS from the parasympathetic receptors in the pancreas. Without being limited to one given theory, the ablation of the different nerve types contribute to the following roles in hindering the cancer progression and/or improving patient outcomes: 1. decreasing sympathetically mediated neurotransmitter release in the pancreas, decreases tumor growth rates; 2. disconnection of afferent nerves reduces pain associated with tumor growth; and 3. disconnection of vagal nerves down regulated parasympathetically mediated neurotransmitter release in the pancreas, altering pancreatic juice composition and secretion. Furthermore, physically blocking the neural pathways (e.g., such as with post procedural scar tissue, via disruption of the nerve channels through the tissues, etc.), may physically hinder the metastatic progression of the cancer along those channels and out into surrounding tissues.

In the associated or subsequent arteries, upon placement of the catheter tip in the vicinity of the target nerves, the catheter may be used to treat the nerves in accordance with the present disclosure. Sensors on the catheter tip may be used to confirm completion of the procedure and then the catheter may be advanced to another associated artery, or removed from the subject.

The procedure may be used to decrease growth rate of the cancerous tumor, decrease cancer related pain, alter pancreatic juice formation, composition, and/or secretion rate, decrease neural signaling in the vicinity of the microenvironment of the tumor, and/or block off metastatic pathways for the cancer cells.

Example 4

The following, non-limiting example, is directed to treatment of pancreatic cancer in a human subject. A catheter in accordance with the present disclosure may be advanced along an arterial pathway to the superior and inferior pancreaticoduodenal arteries and branches thereof, the dorsal pancreatic artery, and the splenic artery. The catheter tip may be equipped with one or more electrode elements and/or drug delivery elements for treating target nerves in the vicinity of the associated artery.

Upon placement in the vicinity of the target nerves, the catheter may be used to treat the nerves in accordance with the present disclosure. Upon completion of the procedure, the catheter may be advanced to another associated artery, or removed from the subject.

The procedure may be used to decrease growth rate of the cancerous tumor, decrease cancer related pain, alter pancreatic juice formation, composition, and/or secretion rate, and/or block off metastatic pathways for the cancer cells.

Example 5

The following, non-limiting example, is directed to treatment of femur bone cancer in a human subject. A catheter in accordance with the present disclosure may be advanced along an arterial pathway to a nutrient artery and or a branch thereof serving the femur bone so as to interface with and/or to treat nerves innervating a spongy bone, a periosteal space, a joint, an epiphyseal space, a metaphyseal space, or the like. The catheter tip, equipped with one or more sensing elements, each in accordance with the present disclosure is positioned within the nutrient artery such that the sensing elements are coupled to the local nerves surrounding the artery. Once placed within a corresponding artery, baseline readings of neural traffic are taken around the wall of the artery. The nerve types, presence, and/or function are confirmed and an ablation procedure, stimulation procedure, or selective neuro-remodeling procedure is completed with the catheter to perform one or more of the following functions: 1. disconnect and/or block the CNS from the sympathetic receptors in the bone; 2. disconnect pain sensory receptors in the bone and/or surrounding organs from the CNS; and 3. disconnect the parasympathetic receptors in the bone from the CNS. Without being limited to one given theory, the ablation of the different nerve types contribute to the following roles in hindering the cancer progression and/or improving patient outcomes: 1. decreasing sympathetically mediated neurotransmitter release in the bone, decreases tumor growth rates, increases bone growth and decreases bone resorption; 2. disconnection of afferent nerves reduces pain associated with tumor growth in the bone; and 3. blocking of parasympathetic nerves cuts off metastatic pathways for the tumor cells to migrate into different regions of the body. One or more of the procedures may be completed depending on the goal of the procedure. Physically blocking the neural pathways (e.g., such as with post procedural scar tissue, via disruption of the nerve channels through the tissues, etc.), may physically hinder the metastatic progression of the cancer along those channels and out into surrounding tissues.

Upon placement in the vicinity of the target nerves, the catheter may be used to treat the nerves in accordance with the present disclosure. Sensors on the catheter tip may be used to confirm completion of the procedure and then the catheter may be advanced to another associated artery, or removed from the subject.

The procedure may be used to decrease growth rate of the cancerous tumor, decrease cancer related pain, alter bone growth and resorption rates, and/or block off metastatic pathways for the cancer cells to escape into surrounding tissues.

Example 6

The following, non-limiting example, is directed to treatment of femur cancer and/or associated cancer pain in a human subject. A catheter in accordance with the present disclosure may be advanced along an arterial pathway to a nutrient artery and or a branch thereof serving the femur bone. The catheter tip may be equipped with one or more electrode elements and/or drug delivery elements for treating nerves in the vicinity of the associated artery.

Upon placement in the vicinity of the target nerves, the catheter may be used to treat the nerves in accordance with the present disclosure. Upon completion of the procedure, the catheter may be advanced to another associated artery, or removed from the subject.

The procedure may be used to decrease growth rate of the cancerous tumor, decrease cancer related pain, alter bone growth and resorption rates, and/or block off metastatic pathways for the cancer cells.

Example 7

The following, non-limiting example, is directed to bone reinforcement to treat and/or prevent development of osteoporosis in a human subject. A catheter in accordance with the present disclosure may be advanced along an arterial pathway to a nutrient artery and or a branch thereof serving the femur bone. The catheter tip, equipped with one or more sensing elements, each in accordance with the present disclosure, is positioned within the nutrient artery such that the sensing elements are coupled to the local nerves surrounding the artery. Once placed within a corresponding artery, baseline readings of neural traffic are taken around the wall of the artery. The nerve types, presence, and/or function are confirmed and an ablation procedure, stimulation procedure, or selective neuro-modulation procedure is completed with the catheter, or alternatively using the catheter to guide placement of a neuromodulation electrode, etc. to perform one or more of the following functions: 1. disconnect and/or block the CNS from the sympathetic receptors in the bone (e.g., down regulate local sympathetic nerve activity); 2. disconnect pain sensory receptors in the bone and/or surrounding organs from the CNS; and 3. stimulate the parasympathetic receptors in the bone (e.g., up regulate local parasympathetic nerve activity). Without being limited to one given theory, the ablation and/or stimulation of the different nerve types contribute to the following roles in altering the bone density in the femur, slowing/reversing the progression of osteoporosis in the subject, and/or improving patient outcomes: 1. decreasing sympathetically mediated neurotransmitter release in the bone, increases bone growth and decreases bone resorption rates; 2. disconnection of afferent nerves reduces pain associated with bone remodeling processes in the femur bone; and 3. stimulation or increases in activity associated with parasympathetic nerves up regulates parasympathetically mediated neurotransmitter release in the bone, increasing bone growth and decreasing bone resorption. One or more of the procedures outlined above may be completed depending on the goal of the procedure. Physically blocking the neural pathways (e.g., such as with post procedural scar tissue, via disruption of the nerve channels through the tissues, etc.), may physically hinder the re-innervation of the nerves along those channels, thus slowing the re-innervation process and improving the durability of the procedure.

Example 8

The following, non-limiting example, is directed to bone reinforcement to treat and/or prevent development of osteoporosis in a human subject or to the treatment of bone cancer in a human subject. A focused energy or chemical delivery element is guided to the nutrient artery of the target bone (e.g., femur bone). In one, non-limiting example, the energy delivery is provided by a focused high frequency ultrasound (HIFU) delivery system. The focused energy is delivered to the region surrounding the nutrient artery and/or the perivascular region of the bone. A thermal increase in the target tissues is used to ablate the nerves within the target tissues. In another, non-limiting example, a sympathetic nerve selective neurotoxin (e.g., 6-hydroxydopamine, ω-conotoxin GVIA, bungarotoxin, etc.), or generally acting neurotoxin (e.g., ethanol, phenol, etc.), is directed to the tissues surrounding the nutrient artery or perivascular space of the target bone (e.g., a femur). Such delivery of energy or chemical may be guided by one or more imaging techniques (e.g., ultrasound, CT, MRI, etc.). The energy or chemical delivery is used to perform one or more of the following functions: 1. disconnect and/or block the CNS from the sympathetic receptors in the bone (e.g., down regulate local sympathetic nerve activity); 2. disconnect pain sensory receptors in the bone and/or surrounding organs from the CNS; and 3. preserve parasympathetic innervation in the bone (e.g., such as via application of a neuro-selective toxin). Without being limited to one given theory, the ablation and/or selective preservation of the different nerve types contribute to the following roles in altering the bone density in the femur, slowing/reversing the progression of osteoporosis in the subject, and/or improving patient outcomes: 1. decreasing sympathetically mediated neurotransmitter release in the bone, increases bone growth and decreases bone resorption rates; 2. disconnection of afferent nerves reduces pain associated with bone remodeling processes in the femur bone; and 3. maintains levels of activity associated with parasympathetic nerves up regulates parasympathetically mediated neurotransmitter release in the bone, increasing bone growth and decreasing bone resorption. One or more of the procedures outlined above may be completed depending on the goal of the procedure. Physically blocking the neural pathways (e.g., such as with post procedural scar tissue, via disruption of the nerve channels through the tissues, etc.), may physically hinder the re-innervation of the nerves along those channels, thus slowing the re-innervation process and improving the durability of the procedure.

Example 9

The following, non-limiting example, is directed to treatment of prostate cancer or benign prostate hyperplasia in a human subject. A catheter in accordance with the present disclosure may be advanced along an arterial pathway to a prostatic artery and or a branch thereof serving the prostate. The catheter tip, equipped with one or more sensing elements, each in accordance with the present disclosure is positioned within the prostatic artery such that the sensing elements are coupled to the local nerves surrounding the artery. Once placed within a corresponding artery, baseline readings of neural traffic are taken around the wall of the artery. The nerve types, presence, and/or function are confirmed and an ablation procedure, stimulation procedure, or selective neuro-remodeling procedure is completed with the catheter to perform one or more of the following functions: 1. disconnect and/or block the CNS from the sympathetic receptors in the prostate; 2. disconnect pain sensory receptors in the prostate and/or surrounding organs from the CNS; and 3. disconnect the parasympathetic receptors in the prostate from the CNS. Without being limited to one given theory, the ablation of the different nerve types contribute to the following roles in hindering the cancer progression and/or improving patient outcomes: 1. decreasing sympathetically mediated neurotransmitter release in the prostate decreases tumor growth rates and slows or reverses prostate hyperplasia; 2. disconnection of afferent nerves reduces pain associated with tumor growth in the prostate; and 3. blocking of parasympathetic nerves cuts off metastatic pathways for the tumor cells to migrate into different regions of the body. One or more of the procedures may be completed depending on the goal of the procedure. Physically blocking the neural pathways (e.g., such as with post procedural scar tissue, via disruption of the nerve channels through the tissues, etc.), may physically hinder the metastatic progression of the cancer along those channels and out into surrounding tissues.

The baseline readings or readings made during one or more stress tests in accordance with the present disclosure, may be used to ensure that treatment is targeting the correct nerves, and not prone to causing collateral damage to surrounding structures. In one non-limiting example, a local electrical stimulus is provided to the surrounding nerves via the catheter tip (e.g., via a collection of the sensing elements, via dedicated stimulation/ablation electrodes, etc.) as part of an identification, or functional assessment step of the procedure. During stimulation, hemodynamics and/or feelings of subject sensation in the penis are determined, if penile sensation or response is detected, the catheter may be advanced to a new site, an alternative branch of the prostatic artery, so as to ensure that the treatment does specifically targets nerves coupled to the prostate or a cancerous tumor associated therewith.

Upon placement in the vicinity of the target nerves, the catheter may be used to treat the nerves in accordance with the present disclosure. Sensors on the catheter tip may be used to confirm completion of the procedure and then the catheter may be advanced to another associated artery, or removed from the subject.

The procedure may be used to decrease growth rate of the cancerous tumor, decrease cancer related pain, alter prostate growth rates, slow, halt, or reverse prostate hyperplasia, and/or block off metastatic pathways for the cancer cells to escape into surrounding tissues.

Example 10

The following, non-limiting example, is directed to a method for using a system in accordance with the present disclosure to identify and assess the functionality of one or more nerves in the vicinity of an artery serving a target organ in a human subject. A catheter in accordance with the present disclosure may be advanced along an arterial pathway to the artery or a branch thereof serving the target organ. The catheter tip, equipped with one or more sensing elements, each in accordance with the present disclosure is positioned within the artery such that the sensing elements are coupled to the local nerves surrounding the artery. Once placed within a corresponding artery, baseline readings of neural traffic are taken around the wall of the artery. The nerve types, presence, and/or function are confirmed during baseline testing or during application of a stress test in accordance with the present disclosure. In one non-limiting example of such a stress test, one or more boluses of a neurotransmitter, hormone, a medication, or the like is released into the artery from the sensing tip of the catheter. The corresponding neural traffic is recorded during the stress test and the identity, location, functionality, sensitivity of the neural traffic to the bolus, or the like is analyzed to select one or more targets for treatment, to assess the subject for a treatment option, etc. Depending on the results of the analysis, an ablation procedure, stimulation procedure, or selective neuro-remodeling procedure may be completed with the catheter in accordance with the present disclosure, or the catheter is moved to an alternative test site, or removed from the subject. Such a configuration may be advantageous for assessing organ, neuroendocrine, function or sensitivity to one or more aspects of the stress test, to identify nerves in the vicinity of the catheter for possible treatment thereof, etc.

After identification of the target nerves, a procedure may be preferentially directed at the target nerves while minimizing collateral damage or unwanted effects associated with treating the wrong nerve structures. In one non-limiting example, the stress test may be used to identify the regions with high levels of sympathetic nerves and the regions with high levels of parasympathetic nerves. Depending on the goal of the therapy (e.g., sympathectomy while preserving the parasympathetic innervation, etc.), the therapy may be directed towards the target nerves.

Example 11

The following, non-limiting example, is directed to a method for using a system in accordance with the present disclosure to treat one or more target nerves in the vicinity of an artery serving a target organ in a human subject. A catheter in accordance with the present disclosure may be advanced along an arterial pathway to the artery or a branch thereof serving the target organ. The catheter tip, equipped with one or more sensing elements and therapeutic elements, each in accordance with the present disclosure is positioned within the artery such that the sensing elements are coupled to the local nerves surrounding the artery. Once placed within a corresponding artery, baseline readings of neural traffic are taken around the wall of the artery. The nerve types, presence, and/or function are confirmed during baseline testing or during application of a stress test in accordance with the present disclosure. Depending on the results of the analysis, an ablation procedure, stimulation procedure, or selective neuro-remodeling procedure may be completed with the catheter in accordance with the present disclosure, or the catheter may be moved to an alternative test site, or removed from the subject. The sensing elements may be configured to monitor the associated neural traffic before, during, and/or after the procedure so as to assess when the procedure has been completed (e.g., when a target nerve has been functionally disabled, when a non-target nerve is starting to be affected by the therapy, etc.). Such a configuration may be advantageous for performing such procedures with a high degree of confidence related to the completion thereof, and to the minimizing of collateral damage associated therewith.

Example 12

The following, non-limiting example, is directed to a method for using a system in accordance with the present disclosure to assess and/or treat one or more target nerves in the vicinity of an artery serving a target organ in a human subject. A catheter in accordance with the present disclosure may be advanced along an arterial pathway to the artery or a branch thereof serving the target organ. The catheter tip, equipped with one or more sensing elements, therapeutic elements, and/or substance delivery elements, each in accordance with the present disclosure is positioned within the artery such that the sensing elements are coupled to the local nerves surrounding the artery. In aspects, the catheter may include a therapeutic element configured so as to deliver a therapeutic agent into or through the wall of the artery (e.g., so as to treat the target nerves), and a substance delivery element arranged such that a bolus of a substance may be delivered into the lumen of the artery (e.g., so as to stress test a downstream organ, treat receptors in the organ associated with the artery, etc.). Once placed within a corresponding artery, baseline readings of neural traffic are taken around the wall of the artery. The nerve types, presence, and/or function are confirmed during baseline testing or during application of a stress test in accordance with the present disclosure (e.g., such as via delivery of a substance into the artery via the substance delivery element, etc.). Depending on the results of the analysis, an ablation procedure, stimulation procedure, or selective neuro-remodeling procedure may be completed with the catheter in accordance with the present disclosure, or the catheter may be moved to an alternative test site, or removed from the subject. The sensing elements may be configured to monitor the associated neural traffic before, during, and/or after the procedure so as to assess when the procedure has been completed (e.g., when a target nerve has been functionally disabled, when a non-target nerve is starting to be affected by the therapy, etc.). Such a configuration may be advantageous for performing such procedures with a high degree of confidence related to the completion thereof, and to the minimizing of collateral damage associated therewith.

Example 13

The following, non-limiting example, is directed to treatment of cancer (e.g., pancreatic cancer), internal pain or neural mediated hyperplasia in organs (e.g., benign prostatic hyperplasia). Pancreatic carcinoma cells (Mia PaCa2) were injected into the head of the pancreas of 10 athymic nude mice (subjects). A bolus of ethanol (50-75 uL) was administered to the celiac ganglion and surrounding nerves of five of the mice (i.e., the EtOH ablation group). The remaining five subjects constitute the untreated control group.

Figure 11A:
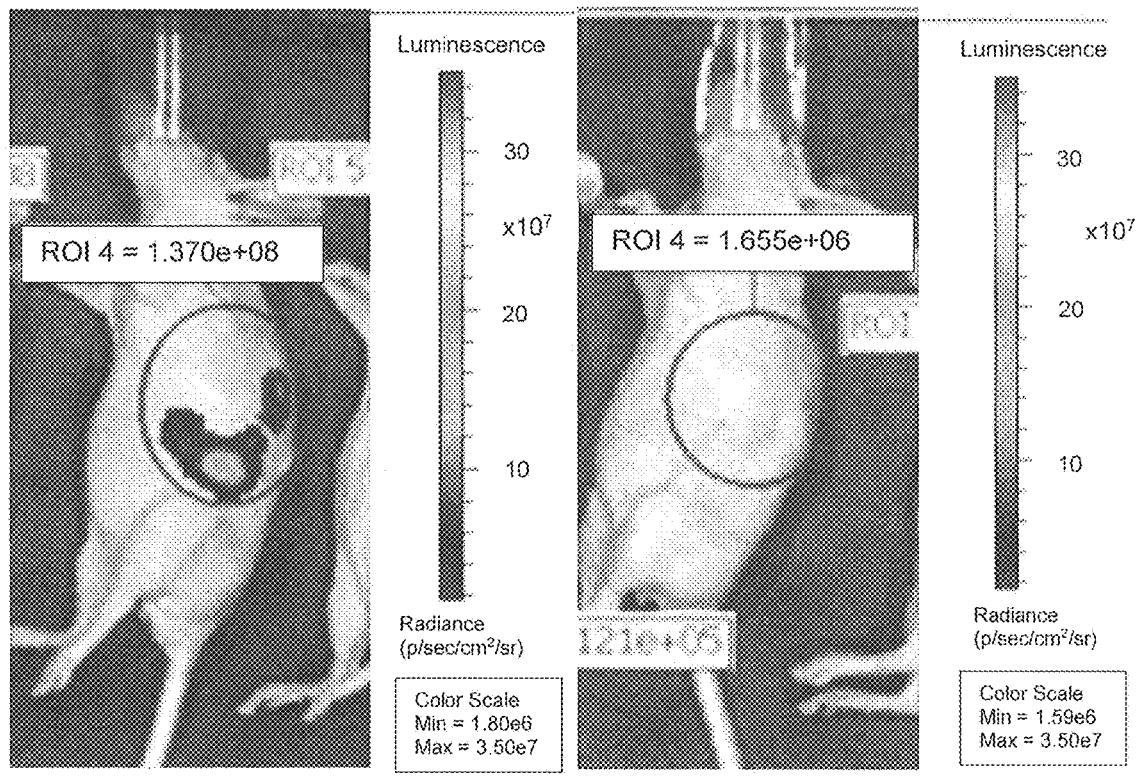
FIG. 11a shows exemplary IVIS images taken with the same settings illustrating median tumor bioluminescence at 3 weeks post procedure in the control group (left) and the EtOH group (right) in accordance with the present disclosure.
Figure 11B:
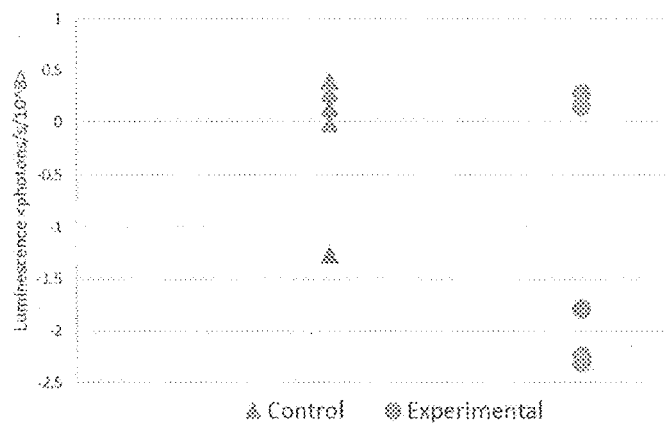
FIG. 11b shows exemplary logarithms of the IVIS measured bioluminescence levels at 3 weeks post procedure corresponding to the control group (triangles) and the EtOH group (circles) in accordance with the present disclosure.

The mice were tracked for 7 weeks post procedure. Tumor growth rates in all subjects were monitored via bioluminescent imaging with an in vivo imaging system, i.e., IVIS Spectrum (Xenogen), twice weekly during the experiment. IVIS images from the median subject in each group at 3 weeks post procedure are shown in FIG. 11a. In FIG. 11a, the treatment arm appears to show a substantially decreased tumor growth rate compared with the control arm (nearly a 100× difference in bioluminescence between the median responders). A logarithmic comparison between groups of the tumor luminescence for each subject at 3 weeks is shown in FIG. 11b. Overall, the mean tumor size in the experimental group is half of that of the control group (1-sided, alpha=0.05, n=5, p=0.11). In addition, the median tumor size at 3 weeks is less than 1% of the control group median tumor size. As shown in FIG. 11b, a subset of the experimental group did not respond to treatment, as complete neural ablation was likely not achieved in this sub group due to the exceptionally small and delicate nature of the murine target arteries.

Figure 11C:
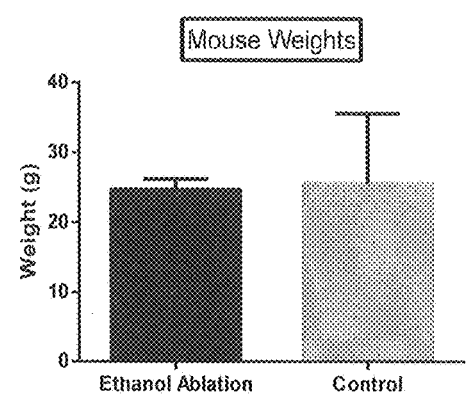
FIG. 11c shows a graph illustrating the mass difference between control group and EtOH group at 7 weeks in accordance with the present disclosure.

The experiment was terminated at 7 weeks. FIG. 11c illustrates that there was no overall size difference between subjects in the groups at 7 weeks. Thus, giving at least initial indication that the procedure is safe.

The metastases per group were assessed during necropsy. The results are shown in Tables 1 and 2 below. As shown, even with the non-responder sub-group, the incidence of metastases were considerably lower in the EtOH-treated group than in the untreated control group. Tables 1 and 2 show that the overall rate of metastases to nearby sites including local invasion, the stomach, and the liver were less in the EtOH-treated group than in the untreated control group. The two groups had the same incidence of metastases traveling to the spleen. Note that the nerves running from the pancreas to the spleen were not treated during this experiment, but the procedure disclosed herein may be applied to such nerves in large animals and humans so as to treat this pathway separately or in combination with the treatment of other anatomical sites in the vicinity of the target organ. Results demonstrate that overall, there was less tumor mass in subjects with ablated peri-pancreatic nerves than in subjects of the control group, fewer metastases in the ablated group, and similar overall body weights between the ablated group and the control group.

TABLE 1

Occurrence of metastases by subject

| Mouse # | Control Group | EtOH Ablation Group |
|---|---|---|
| 1 | Local invasion, spleen | spleen |
| 2 | Local invasion | Local invasion, spleen |
| 3 | Local invasion, spleen | none |
| 4 | Local invasion, spleen, liver | Local invasion, spleen |
| 5 | Local invasion, spleen, liver, stomach | spleen |

TABLE 2

Occurrence of metastases by group

| Metastasis Site | Control Group | EtOH ablation Group |
|---|---|---|
| Local invasion | 5/5 | 2/5 |
| Spleen | 4/5 | 4/5 |
| Liver | 2/5 | 0/5 |
| Stomach | 1/5 | 0/5 |

Embodiments of the invention safely and effectively monitor and quantify sympathetic nerve activity from the porcine renal artery lumen, organ parenchyma, and renal adventitia, with a clinically meaningful approach. Moreover, embodiments of the invention demonstrate that physiologic signals can be monitored and used as feedback to indicate completion of an ablation or neuromodulation procedure. Still further, embodiments of the invention show that tumor growth and metastases may be slowed by peri-pancreatic autonomic nerve ablation in an established and validated murine model of pancreatic cancer.

Embodiments of the invention locate (via sensing) and safely ablate pancreatic afferent/efferent neural control traffic to treat cancer, for example, but not limited to, pancreatic cancer. In humans, the sensing-ablation techniques disclosed herein may enhance quality and quantity of life by at least the following mechanisms: relieve cancer pain safely, simply, and rapidly in patients suffering this fatal disease; improve blood glucose control resulting from tumor-induced beta cell destruction; and improve survival through limiting inflammation and metastases pathways.

Embodiments of the invention can be applied to any cancer, internal pain, or organ hyperplasia treatments. The methodologies and systems described herein may be applied to all solid cancers and in particular, perineural invading cancers. While the focus of illustrative embodiments described herein is not on ablating cancerous tissue, the methodologies and systems described herein may be applied thereto.

Embodiments of the invention may be used to block or slow cancer progression by: 1) reducing neurotransmitter release in the tumor microenvironment that drives tumor growth (e.g., adrenaline); 2) disconnecting the microenvironment receptors from the CNS (to treat the cancer pain); and 3) blocking off the nerve pathways, which the cancer cells migrate along during metastasis. Embodiments of the invention may be used to treat any neurally mediated hyperplasia in organs, for example, but not limited to, benign prostatic hyperplasia (BPH). The methodologies and systems described herein may also be used for blocking internal organ pain, for example, but not limited to, in treating pancreatitis and general abdominal pain.

Notwithstanding the appended claims, the disclosure set forth herein is also defined by the following clauses:

1. A system for treating a cancerous tumor, altering an organ function, and/or altering neural traffic in a microenvironment coupled to a target organ within a body, comprising:

a catheter or guidewire dimensioned for insertion into a lumen with a wall, the lumen in fluid communication with the target organ and/or the tumor; and the catheter or guidewire comprising a distal tip configured to interface with the wall of the lumen, the distal tip configured to deliver energy and/or a substance to one or more nerves coupled to the target organ, and/or the wall of the lumen.

2. The system in accordance with clause 1, wherein the distal tip comprises a balloon, a basket, a deployable helix, a deployable microneedle, or a combination thereof for interfacing with the wall.

3. The system in accordance with clause 1 or 2, wherein the energy is thermal energy, RF current, MW current, ultrasound, radiation, cryotherapy, or combinations thereof.

4. The system in accordance with any one of clauses 1-3, wherein the substance is a medicament, a denervating agent, an sympathetic nerve specific denervating agent, a parasympathetic nerve specific denervating agent, a neuroblocking agent, a highly specific neuroblocking agent, or a combination thereof.

5. The system in accordance with clause 4, wherein the substance is ethanol, phenol, botulinum toxin, a derivative, or a combination thereof.

6. The system in accordance with any one of clauses 1-5, comprising one or more sensing elements coupled with the distal tip, each sensing element configured to interface with and/or monitor electrophysiological activity from one or more of the nerves.

7. The system in accordance with any preceding clause, comprising a substance eluting element coupled to the distal tip, configured to deliver a substance, a medicament, a denervating substance, or combination thereof into the target organ, into a perivascular site surrounding the wall of the lumen, into the adventitia of the lumen, into a microenvironment of the tumor, into the lumen, or a combination thereof.

8. The system in accordance with any preceding clause, wherein the energy and/or substance is configured to interrupt, block, and/or augment neural traffic along one or more nerves upon delivery from the distal tip.

9. The system in accordance with any preceding clause, comprising a balloon coupled with the distal tip, the balloon coupled to a fluid source so as to be expand-ably deployed during a procedure so as to interface with the walls of lumen upon placement of the distal tip therein.

10. The system in accordance with clause 9, wherein the balloon comprises one or more energy delivery elements, and/or sensing elements to interface with the wall of the lumen and/or the nerves.

11. The system in accordance with any one of clauses 6-10, wherein the system is configured to direct energy through the energy delivery elements based upon the information collected by the sensing elements.

12. The system in accordance with any one of clauses 6-11, wherein the sensing elements are configured to monitor and/or determine the signals relating to regions of abnormal electrophysiological activity, determine the direction of nerve traffic along nerves in the vicinity of the lumen, sympathetic neural activity in the vicinity of the lumen, determine the type of nerves situated near the sensing element, determine the effectiveness of the energy and/or substance delivery, determining the response of nerve traffic to a stress test performed on the body or the organ, or combinations thereof.

13. The system in accordance with any preceding clause wherein the system is configured to direct the energy delivery into one or more regions of the lumen wall, through the lumen wall, into the adventitia, into the target organ, adjacent to the lumen, into a microenvironment of the tumor, or combinations thereof.

14. The system in accordance with any one of clauses 6-13, comprising a stress testing element, configured to apply a local and/or systemic stress to the body, one or more of the sensing elements configured to monitor the response of the nerves to the stress.

15. The system in accordance with any one of clauses 1-14, wherein the distal tip has a characteristic diameter of less than 1 mm, less than 0.75 mm, less than 0.5 mm, or less than 0.3 mm so as to access the lumen near to or within a site within the target organ.

16. Use of a system in accordance with any one of clauses 6-15 to diagnose a disease state, determine a function of the wall, and/or determine a type of tissues adjacent to the lumen based upon the data obtained by the one or more sensing elements.

17. Use of a system in accordance with any one of clauses 1-15 to reduce, and/or prevent communication of pain signals originating within a tumor microenvironment or associated organ from traveling along the nerve.

18. Use of a system in accordance with any one of clauses 1-15 to treat and/or slow the progression of a cancerous tumor.

19. Use of a system in accordance with any one of clauses 1-15 to treat cancer of the prostate, pancreas, breast, cervix, ovaries, bladder, bone, or combinations thereof.

20. Use of a system in accordance with any one of clauses 1-15 to slow, to reverse, and/or to prevent perineural invasion of a cancerous tumor into a surrounding neural microenvironment.

21. Use of a system in accordance with any one of clauses 1-15 to interrupt, decrease, and/or stop neural communication to/from a cancerous tumor and/or the microenvironment surrounding the tumor to a remote site within a body.

22. Use of a system in accordance with any one of clauses 1-15 to modulate, affect, slow, or halt tumorigenesis of a cancerous tissue site within a body.

23. A method for treating a cancerous tumor, altering an organ function, and/or altering neural traffic in a microenvironment coupled to the tumor or a target organ within a body comprising:

accessing a wall of a lumen in the vicinity of the tumor or organ; and delivering energy and/or a substance to at least a portion of the wall of the lumen, through at least a portion of the wall of the lumen, to a nerve coupled with the tumor, and/or into the tissues surrounding the tumor or organ.

24. The method in accordance with clause 23 comprising, collecting physiologic data from the tumor, from a nerve coupled to the tumor, and/or within the vicinity of the tumor and/or a perivasculature of the lumen.

25. The method in accordance with clause 24 comprising, directing the energy and/or substance based upon the collected physiologic data.

26. The method in accordance with clause 25 comprising, collecting further physiologic data after the delivery of the energy and/or the substance to determine if the delivery affected the microenvironment around the tumor, the nerve coupled to the tumor, and/or the perivasculature of the lumen.

27. The method in accordance with any one of clauses 23-25, comprising applying a stress test to the subject during the collecting of physiologic data.

28. The method in accordance with clause 27, wherein the stress test comprises a valsalva maneuver, a tilt table test, elevating one or more legs, transient siting to standing exercises, execute a change in posture, move from a prone position to a sitting or standing position, a breath hold technique, or combinations thereof.

29. The method in accordance with clause 28, wherein the stress test comprises injecting a vasodilator, a vasoconstrictor, a neuroblocker, a neurostimulant, a diuretic, insulin, glucose, beta-adrenergic receptor antagonist, angiotensin-11 converting enzyme inhibitor, calcium channel blocker, an HMG-CoA reductase inhibitor, digoxin, an anticoagulant, a diuretic, a beta blocker, an ACE inhibitor, a steroid, or combination thereof to the organ and/or subject and monitoring the local response thereto.

30. The method in accordance with clause 29, wherein the injection is directed into the lumen, the adventitia surrounding the lumen, into the tumor, and/or into an organ coupled thereto.

31. The method in accordance with one of clauses 29-30, wherein the step of injection is provided by a system in accordance with any one of clauses 1-15.

32. The method in accordance with any one of clauses 23-29, wherein one or more steps is performed with a system in accordance with any one of clauses 1-15.

33. The method in accordance with any one of clauses 23-32, wherein the target organ is a bone.

34. The method in accordance with clause 33, wherein the energy and/or substance delivery is performed into a vessel, a periosteal space, a foramen, and/or a medullary cavity of the bone, or a combination thereof.

35. The method in accordance with one of clauses 33 or 34, wherein the bone is a long bone and the lumen is a nutrient, epiphyseal, or metaphyseal artery, vein or forma.

36. A method for treating a cancerous tumor within a body comprising, neuromodulating electrophysiological activity of one or more nerves coupled to the cancerous tumor and/or a microenvironment surrounding the tumor.

37. The method for treating a cancerous tumor in accordance with clause 36, wherein the step of neuromodulating comprises stimulating, and/or ablating the nerves.

38. The method for treating a cancerous tumor in accordance with one of clauses 36 or 37, comprising monitoring the electrophysiological activity before, during, and/or after the step of neuromodulating.

39. The method for treating a cancerous tumor in accordance with clause 38, comprising determining the effectiveness of the step of neuromodulating based upon the monitoring.

40. The method for treating a cancerous tumor in accordance with one of clauses 38 or 39, comprising determining the type and/or location for the step of neuromodulating based upon the monitoring.

41. The method for treating a cancerous tumor in accordance with any one of clauses 36-40 wherein one or more steps are provided by a system in accordance with any one of clauses 1-15.

42. Use of a method in accordance with any one of clauses 23-35 or any one of clauses 36-41 to treat pancreatic cancer, prostate cancer, breast cancer, liver cancer, cervical cancer, ovarian cancer, bladder cancer, bone cancer, or combinations thereof.

43. A method for treating a cancerous tumor, altering an organ function, and/or altering neural traffic in a microenvironment coupled to the tumor or a target organ within a body comprising:
accessing a wall of a lumen in the vicinity of the tumor or organ;
monitoring baseline neural traffic in the vicinity of the lumen to identify one or more target nerves; and
delivering energy and/or a substance to at least a portion of the wall of the lumen, through at least a portion of the wall of the lumen, to the target nerves coupled with the tumor, and/or into the tissues surrounding the tumor or organ.

44. The method in accordance with clause 43, wherein the step of monitoring comprises collecting physiologic data from the tumor, from a nerve coupled to the tumor, and/or within the vicinity of the tumor and/or a perivasculature of the lumen.

45. The method in accordance with clause 43 or 44, comprising generating a metric based upon the monitoring and/or physiologic data, the metric relating to identification of the target nerve types, characterization of the nerve traffic, determining the direction of target nerve traffic, locating nerve types in the vicinity of the lumen, or a combination thereof.

46. The method in accordance with clause 44 or 45 comprising, directing the energy and/or substance based upon the collected physiologic data and/or the metric.

47. The method in accordance with any one of clauses 43-46 comprising, collecting further physiologic data and/or metrics after the delivery of the energy and/or the substance to determine if the delivery affected the neural traffic, the nerve function, the microenvironment around the tumor, the function of a target nerve coupled to the tumor, and/or the perivasculature of the lumen.

48. The method in accordance with any one of clauses 43-47, comprising applying a stress test to the subject during the collecting of physiologic data or neural monitoring.

49. The method in accordance with clause 48, wherein the stress test comprises a Valsalva maneuver, a tilt table test, elevating one or more legs, transient siting to standing exercises, execute a change in posture, move from a prone position to a sitting or standing position, a breath hold technique, or combinations thereof.

50. The method in accordance with clause 48, wherein the stress test comprises injecting a vasodilator, a vasoconstrictor, a neuroblocker, a neurostimulant, a diuretic, insulin, glucose, beta-adrenergic receptor antagonist, angiotensin-11 converting enzyme inhibitor, calcium channel blocker, an HMG-CoA reductase inhibitor, digoxin, an anticoagulant, a diuretic, a beta blocker, an ACE inhibitor, a steroid, or combination thereof to the organ and/or subject and monitoring the local response thereto.

51. A system for treating a cancerous tumor, altering an organ function, and/or altering neural traffic in a microenvironment coupled to a target organ within a body, comprising:
a catheter or guidewire dimensioned for insertion into a lumen with a wall, the lumen in fluid communication with the target organ and/or the tumor;
the catheter or guidewire comprising a distal tip configured to interface with the wall of the lumen, the distal tip configured to deliver energy and/or a substance to one or more nerves coupled to the target organ, and/or the wall of the lumen; and
the distal tip comprising one or more sensing elements, the sensing elements configured to interface with the nerves and monitor nerve traffic therefrom.

52. The system in accordance with clause 51, wherein the system is configured such that the delivery of the energy and/or the substance is directed based on the monitored nerve traffic.

53. The system in accordance with clause 51 or 52, comprising a processor, coupled with the sensing elements, the processor configured to identify, locate, and/or assess the functionality of one or more of the nerves based upon the monitored nerve traffic.

54. The system in accordance with any one of clauses 52-53, wherein the processor is configured to modulate the effect of the delivery of the energy and/or the substance on the nerves based on the monitored nerve traffic.

55. The system in accordance with any one of clauses 52-54, wherein the processor is configured to determine when to stop the delivery of the energy and/or the substance based on the monitored nerve traffic.

56. The system in accordance with any one of clauses 51-55, wherein the distal tip comprises a balloon, a basket, a deployable helix, a deployable microneedle, or a combination thereof for interfacing with the wall.

57. The system in accordance with any one of clauses 51-56, wherein the energy is thermal energy, RF current, MW current, ultrasound, radiation, cryotherapy, or combinations thereof.

58. The system in accordance with any one of clauses 51-56, wherein the substance is a medicament, a denervating agent, an sympathetic nerve specific denervating agent, a parasympathetic nerve specific denervating agent, a neuroblocking agent, a highly specific neuroblocking agent, or a combination thereof.

59. The system in accordance with clause 58, wherein the substance is ethanol, phenol, botulinum toxin, a derivative, or a combination thereof.

60. The system in accordance with any one of clauses 51-59, wherein one or more of the sensing elements is configured to interface with and/or monitor electrophysiological activity from one or more of the nerves.

61. The system in accordance with any one of clauses 51-60, comprising a substance eluting element coupled to the distal tip, configured to deliver a substance, a medicament, a denervating substance, or combination thereof into the target organ, into a perivascular site surrounding the wall of the lumen, into the adventitia of the lumen, into a microenvironment of the tumor, into the lumen, or a combination thereof.

62. The system in accordance with any one of clauses 51-61, wherein the energy and/or substance is configured to interrupt, block, and/or augment neural traffic along one or more nerves upon delivery from the distal tip.

63. The system in accordance with any one of clauses 51-62, comprising a balloon coupled with the distal tip, the balloon coupled to a fluid source so as to be expand-ably deployed during a procedure so as to interface with the walls of lumen upon placement of the distal tip therein.

64. The system in accordance with clause 63, wherein the balloon comprises one or more energy delivery elements, and/or sensing elements to interface with the wall of the lumen and/or the nerves.

65. The system in accordance with any one of clauses 51-64, wherein the system is configured to direct energy through the energy delivery elements based upon the information collected by the sensing elements.

66. The system in accordance with any one of clauses 51-65, wherein the sensing elements are configured to monitor and/or determine the signals relating to regions of abnormal electrophysiological activity, determine the direction of nerve traffic along nerves in the vicinity of the lumen, sympathetic neural activity in the vicinity of the lumen, determine the type of nerves situated near the sensing element, determine the effectiveness of the energy and/or substance delivery, determining the response of nerve traffic to a stress test performed on the body or the organ, or combinations thereof.

67. The system in accordance with any one of clauses 51-66, wherein the system is configured to direct the energy delivery into one or more regions of the lumen wall, through the lumen wall, into the adventitia, into the target organ, adjacent to the lumen, into a microenvironment of the tumor, or combinations thereof.

68. The system in accordance with any one of clauses 51-67, comprising a stress testing element, configured to apply a local and/or systemic stress to the body, one or more of the sensing elements configured to monitor the response of the nerves to the stress.

69. The system in accordance with any one of clauses 51-68, wherein the distal tip has a characteristic diameter of less than 1 mm, less than 0.75 mm, less than 0.5 mm, or less than 0.3 mm so as to access the lumen near to the target organ and/or near a site within the target organ.

It will be appreciated that additional advantages and modifications will readily occur to those skilled in the art. Therefore, the disclosures presented herein and broader aspects thereof, are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A medical system, comprising:
    a microsurgical tool defining a longitudinal axis, the microsurgical tool configured for percutaneous introduction through a body lumen defined by a lumen wall and having a distal tip segment positionable with respect to a target neural structure, the distal tip segment comprising first, second and third discrete zones longitudinally spaced with respect to the longitudinal axis and each other;
    wherein the first zone comprises at least a first component;
    wherein the second zone comprises at least a second component;
    wherein the third zone is disposed between the first and second zones, the third zone comprising at least a third component;
    wherein the first component and the second component each comprise a same one of: one or more physiological sensors; and one or more stimulatory elements;
    wherein the third component comprises the other one of: one or more physiological sensors; and one or more stimulatory elements;
    wherein the one or more physiological sensors are configured to emit one or more signals representative of physiological data of the target neural structure;
    wherein the one or more stimulatory elements are configured to apply stimulation to the target neural structure, the one or more stimulatory elements comprising at least one of one or more energy delivery elements and one or more substance delivery elements;
    a controller to control operation of each of the first, second and third zones based on the physiological data obtained by the one or more physiological sensors, the controller configured:
        to determine a condition of the target neural structure at least one of before, during and subsequent to application of stimulation to the target neural structure by the one or more stimulatory elements; and
        to control operation of the stimulatory element and coordinate positioning of the distal tip segment relative to the target neural structure, based on the determined condition of the target neural structure.

2. The medical system of claim 1, wherein the one or more stimulatory elements comprise the one or more energy delivery elements, the one or more energy delivery elements being configured to deliver energy adjacent the target neural structure, the energy being at least one of thermal energy, radio frequency current, microwave current, ultrasound, HIFU (high intensity focused ultrasound), radiation, and cryotherapy.

3. The medical system of claim 1, wherein the one or more stimulatory elements comprise the one or more substance delivery elements, the one or more substance delivery elements being configured to deliver a substance adjacent the target neural structure, the substance being at least one of a medicament, a denervating agent, a sympathetic nerve specific denervating agent, a parasympathetic nerve specific denervating agent, a neuroblocking agent, and a highly specific neuroblocking agent.

4. The medical system of claim 3, wherein at least one of the one or more substance delivery elements comprises a microneedle.

5. The medical system of claim 1, wherein the first and second zones are each a sensing zone comprising the one or more physiological sensors, and the third zone is a stimulating zone comprising the one or more stimulatory elements.

6. The medical system of claim 5, wherein the third zone is configured to be biased toward the lumen wall such that the one or more stimulatory elements interface with the lumen wall.

7. The medical system of claim 6, further comprising a delivery sheath disposed about at least the distal tip segment of the microsurgical tool, the delivery sheath configured for longitudinal movement relative to the microsurgical tool to expose the first, second and third zones.

8. The medical system of claim 1, wherein the distal tip segment comprises a balloon, a basket, a deployable helix, a deployable microneedle, or a combination thereof.

9. The medical system of claim 1, further comprising:
    a stress testing element, the stress testing element being configured to apply at least one of a local and a systemic stress to the lumen wall; and one or more sensing elements configured to monitor a response of the target neural structure to the applied stress.

10. The medical system of claim 1, wherein the controller is configured to selectively adjust positioning of at least the distal tip segment of the microsurgical tool relative to a tumor based on the determined condition of the target neural structure.

11. A medical system, comprising:
a microsurgical tool defining a longitudinal axis, the microsurgical tool configured for percutaneous introduction through a body lumen defined by a lumen wall and having a distal tip segment positionable with respect to a target neural structure, the distal tip segment comprising at least two zones, a first one of the at least two zones comprising one or more physiological sensors configured to emit a signal representative of physiological data of the target neural structure and a second of the at least two zones comprising one or more stimulatory elements configured to apply stimulation to the target neural structure, the first zone and the second zone longitudinally spaced with respect to each other along the distal tip segment relative to the longitudinal axis, the one or more stimulatory elements of the second zone comprising at least one of an energy delivery element and a substance delivery element; and
a controller to control operation of each of the at least two zones based on the physiological data obtained by the one or more physiological sensors, the controller configured:
to determine a condition of the neural structure at least one of before, during and subsequent to application of stimulation to the neural structure by the one or more stimulatory elements; and
to control operation of the one or more stimulatory elements based on the determined condition of the neural structure;
wherein the distal tip segment comprises one or more strain measuring elements configured to measure a diameter of the body lumen.

12. A medical system, comprising:
a microsurgical tool defining a longitudinal axis, the microsurgical tool configured for percutaneous introduction through a body lumen defined by a lumen wall and having a distal tip segment positionable with respect to a target neural structure, the distal tip segment comprising:
first and second zones longitudinally spaced with respect to each other along the distal tip segment relative to the longitudinal axis, each of the first and second zones comprising one or more physiological sensors configured to emit one or more signals representative of physiological data of the target neural structure; and
a third zone disposed between the first and second zones, the third zone comprising one or more electrodes configured to apply stimulation to the target neural structure, the third zone being deployable such that the one or more electrodes interface with the lumen wall;
a controller to control operation of at least the third zone based on the physiological data obtained by the one or more physiological sensors of the first and second zones, the controller configured:
to determine a condition of the target neural structure at least one of before, during and subsequent to application of stimulation to the target neural structure by the one or more electrodes of the third zone; and
to continually control operation of the one or more electrodes of the third zone based on the determined condition of the target neural structure; and
an array of microcircuits arranged along a predetermined length of the distal tip segment, the array of microcircuits coupling the one or more physiological sensors and the one or more electrodes with the controller, the array of microcircuits providing signal conditioning of the one or more signals representative of the physiological data of the target neural structure emitted by the one or more physiological sensors; and
one or more strengthening members coupled with the array of microcircuits.

13. The medical system of claim 12, wherein the third zone is configured to be biased toward the lumen wall such that the one or more electrodes interface with the lumen wall.

14. The medical system of claim 12, wherein the third zone is incorporated within a deployable segment of the distal tip segment, the deployable segment comprising one of a balloon, a basket, a helix, a microneedle, or a combination thereof.

15. The medical system of claim 14, further comprising a delivery sheath disposed about at least the deployable segment of the distal tip segment, the delivery sheath configured for longitudinal movement relative to the distal tip segment to expose the deployable segment.

16. The medical system of claim 12, wherein the distal tip segment comprises one or more strain measuring elements configured to measure a diameter of the body lumen.

17. The medical system of claim 12, wherein the distal tip segment further comprises one or more substance delivery elements, the one or more substance delivery elements configured to deliver a substance adjacent the target neural structure, the substance being at least one of a medicament, a denervating agent, a sympathetic nerve specific denervating agent, a parasympathetic nerve specific denervating agent, a neuroblocking agent, and a highly specific neuroblocking agent.

18. The medical system of claim 12, wherein individual microcircuits in the array of microcircuits are arranged in a single file linear pattern along the predetermined length of the distal tip segment.

19. The medical system of claim 12, wherein the one or more strengthening members allow at least one of compression, tension and torque transfer along the predetermined length of the distal tip segment.

20. The medical system of claim 12, wherein the array of microcircuits are coupled to the one or more physiological sensors and the one or more sensors utilizing an ultra-high density interconnect technology.

* * * * *